US006730512B2

(12) United States Patent
Chang

(10) Patent No.: US 6,730,512 B2
(45) Date of Patent: May 4, 2004

(54) COMBINATION IMMUNOGENE THERAPY

(75) Inventor: Lung-Ji Chang, Gainesville, FL (US)

(73) Assignee: Amdl, Inc., Tustin, CA (US)

( * ) Notice: Subject to any disclaimer, the term of this patent is extended or adjusted under 35 U.S.C. 154(b) by 260 days.

(21) Appl. No.: 09/826,025

(22) Filed: Apr. 4, 2001

(65) Prior Publication Data

US 2002/0162123 A1 Oct. 31, 2002

Related U.S. Application Data

(63) Continuation of application No. 08/838,702, filed on Apr. 9, 1997, now abandoned.

(51) Int. Cl.⁷ .................. C12N 15/00; C12N 15/09; C12N 15/63; C12N 15/70; C12N 15/74
(52) U.S. Cl. ............................................. 435/320.1
(58) Field of Search ...................... 435/320.1

(56) References Cited

U.S. PATENT DOCUMENTS

| | | |
|---|---|---|
| 5,637,483 A | 6/1997 | Dranoff et al. |
| 5,681,562 A | 10/1997 | Sobol et al. |
| 5,738,852 A | 4/1998 | Robinson et al. |
| 5,986,170 A | 11/1999 | Subjeck |

FOREIGN PATENT DOCUMENTS

| | | |
|---|---|---|
| WO | 9310219 | 11/1992 |
| WO | 9611279 | 10/1995 |
| WO | 9640238 | 6/1996 |
| WO | 9732987 | 3/1997 |

OTHER PUBLICATIONS

Agatsuma, T. et al. (1996) "Protection of hu–PBL–SCID/Beige Mice From HIV–1 Infection by a Modified Oligonucleotide, RKS–1443" *Antiviral Research* 30(1):A35, XP002073900 (abstract 58).

Zhang, C. et al. (1996) "Protective Immunity to HIV–1 in SCID/Beige Mice Reconstituted with Peripheral Blood Lymphocytes of Exposed but Uninfected Individuals" *Proc. Natl. Acad. Sci. USA* 93:14720–14725.

Lubin, I. et al. (1991) "Engraftment and Development of Human T and B Cells in Mice After Bone Marrow Transplantation" *Science* 252(5004):427–431.

Kilchherr, E. et al. (1993) "Regulation of Human IgE Inhu–PBL–SCID Mice" *Cellular Immunology* 151:241–256.

Mosier, D. et al. (1988) "Transfer of a Functional Human Immune System to Mice with Severe Combined Immunodeficiency" *Nature* 335:256–259.

Mosier, D. et al. (1992) "CD4 T Cells in HIV–1 Infected HU–PBL–SCID Mice" *International Congress of Immunology Abstracts*, Aug. 23–28, Budapest, Hungary, ** abbstract only.

Duchosal, M.A. et al. (1992) "Immunization of hu–PBL–SCID Mice and the Rescue of Human Monoclonal Fab Fragments Through Combinatorial Libraries" *Nature* 355:258–262.

Huppes, W. et al. (1992) "Human to Mouse GVHD: A Model for HIV Studies" *International Congress of Immunology Abstracts*. Aug. 23–28, Budapest, Hungary.

(List continued on next page.)

*Primary Examiner*—Anne-Marie Falk
(74) *Attorney, Agent, or Firm*—Louis C. Cullman

(57) ABSTRACT

The present invention provides to immunogene therapy protocols for the treatment of tumors. In particular, the present invention provides combinations of immune-modulating proteins that induce systemic immunity against tumors. In addition, the present invention provides humanized animal models suitable for the evaluation of anti-human tumor immunity and permit the identification of combinations of immune-modulating genes which when delivered to human tumor cells induce an effective anti-tumor response, including a systemic anti-tumor response.

8 Claims, 9 Drawing Sheets-

OTHER PUBLICATIONS

Segall, H. et al. (1996) "Generation to Primary Antigen–Specific Human Cytotoxic T Lymphocytes in Human/Mouse Radiation Chimera" *Blood* 88(2):721–730.

Greenwood, J.D. (1993) "Xenogenic PBL–SCID Mice: Their Potential and Current Limitations" *Laboratory Animal Science* 43(2):151–155.

Cayeux, S. et al. (1996) "Coexpression of Interleukin–4 and B7.1 in Murine Tumor Cells Leads to Improved Tumor Rejection and Vaccine Effect Compared to Single Gene Transfectants and a Classical Adjuvant" *Human Gene Therapy* 7(4):525–529.

Hodge, J.W. et al. (1994) "Induction of Antitumor Immunity by Recombinant Vaccinia Viruses Expressing B7–1 or B7–2 Costimulatory Molecules" *Cancer Research* 54(1):5552–5555.

Bueler, H. et al. (1996) "Induction of Antigen–Specific Tumor Immunity by Genetic and Cellular Vaccines Against MAGE: Enhanced Tumor Protection by Coexpression of Granulocyte–Macrophage Colony–Stimulating Factor and B7–1" *Molecular Medicine* 2(5):545–555.

Liu, Y. et al. (1992) "Costimulation of T–Cell Growth" *Current Opinion in Immunology* 4:265–270.

Linsley, P.S. et al. (1993) "The role of the CD28 Receptor During T Cell Responses to Antigen" *Annu. Rev. Immunol.* 11:191–212.

Boon, T. et al. (1994) "Tumor Antigens Recognized by T Lymphocytes" *Annu. Rev. Immunol.* 12:337–365.

Garrido, F. et al. (1993) "Natural History of HLA Expression During Tumour Development" *Immunology Today* 14(10):491–499.

Gerlach, J.H. et al. (1996) "Multidrug Resistance" *Cancer Surveys* 5(1):25–46.

Allison, J.P. (1994) "CD28–B7 Interactions in T–Cell Activation" *Current Opinion in Immunology* 6:414–419.

Schwartz, R.H. (1992) "Costimulation of T Lymphocytes: The Role of CD28, CTLA–4, and B7/BB1 in Interleukin–2 Production and Immunotherapy" *Cell* 71:1065–1068.

Cromme, F.V. et al. (1994) "Loss of Transporter Protein, Encoded by the TAP–1 Gene, is Highly Correlated With Loss of HLA Expression in Cervical Carcinomas" *J. Exp. Med.* 179:335–340.

Frei, U. et al. (1993) "Malignancies Under Cyclosporine After Kidney Transplantation: Analysis of a 10–Year Period" *Transplantation Proceedings* 25(1):1394–1396.

Calabresi, P. and Chabner B.A. In: Goodman and Gilman, The Pharmacological Basis of Therapeutics (Pergamon Press, $8^{th}$ Edition) pp. 1209–1216.

Restifo, N.P. et al. (1993) "Identification of Human Cancers Deficient in Antigen Processing" *J. Exp. Med.* 177:265–272.

Houghton, A.N. (1994) "Cancer Antigens: Immune Recognition of Self and Altered Self" *J. Exp. Med.* 180:1–4.

Chong, H. et al. (1996) "Expression of Co–Stimulatory Molecules by Tumor Cells Decreases Tumorigenicity but May Also Reduce Systemic Antitumor Immunity" *Human Gene Therapy* 7:1771–1779.

Alegre et al. (1994) "Severe Combined Immunodeficient Mice Engrafted with Human Splenocytes Have Functional Human T Cells and Reject Human Allografts" *J. Immunol.* 153:2738–2749.

McBride et al. (1995) "Human Immunodeficiency Virus Infection of Xenografted SCID–beige Mice" *J. Med. Virology* 47:130–138.

COMBINATION IMMUNOGENE THERAPY

CROSS-REFERENCE TO RELATED APPLICATION

This application is a continuation of U.S. application Ser. No. 08/838,702, filed Apr. 9, 1997, now abandoned.

FIELD OF THE INVENTION

The present invention relates to immunotherapy for the treatment of tumors. In particular the present invention provides combinations of immune-modulating proteins that induce systemic immunity against tumors and provides humanized animal models for immunogene therapy.

BACKGROUND OF THE INVENTION

Conventional treatment of cancer typically involves the use of chemotherapeutic agents. The father of chemotherapy, Paul Ehrlich, imagined the perfect chemotherapeutic as a "magic bullet;" such a compound would kill invading organisms without harming the host. This target specificity is sought in all types of chemotherapeutics, including anticancer agents.

However, specificity has been the major problem with conventional anticancer agents. In the case of anticancer agents, the drug needs to distinguish between host cells that are cancerous and host cells that are not cancerous. The vast majority of anticancer drugs are indiscriminate at this level. Typically anticancer agents have negative hematological affects (e.g., cessation of mitosis and disintegration of formed elements in marrow and lymphoid tissues) and immunosuppressive action as well as a severe impact on epithelial tissues (e.g., intestinal mucosa), reproductive tissues and the nervous system [Calabresi and Chabner, In: Goodman and Gilman, *The Pharmacological Basis of Therapeutics* (Pergamon Press, 8th Edition) pp. 1209–1216].

Success with chemotherapeutics as anticancer agents has also been hampered by the phenomenon of multiple drug resistance, resistance to a wide range of structurally unrelated cytotoxic anticancer compounds [Gerlach et al. (1986) Cancer Surveys 5:25]. In addition, certain cancers are non-responsive to known chemotherapeutics agents and patients with these cancers invariably die within a short period following diagnosis (e.g., glioblastoma multiforme, recurrent metastatic melanoma, breast, lung and pancreatic cancers).

To address the drawbacks of chemotherapy for the treatment of cancer, immune system-based therapies or cancer immunotherapies have been developed. The goal of cancer immunotherapy is to harness the patient's own immune system to recognize and attack tumors. The recognition and rejection of tumor cells requires the participation of T lymphocytes (T cells).

T cells play a crucial role in a number of immune responses including the recognition of foreign antigens, destruction of virally infected cells and providing help to B cells to permit the production of antibodies that neutralize foreign antigens. In order for a T cell to recognize its target antigen, the antigen must be presented to the T cell by an antigen-presenting cell (APC) such as dendritic cells, macrophages, Langerhans cells and B cells. The APC presents the target antigen as part of a complex containing immune molecules termed major histocompatibility complex (MHC) in mice and human leukocyte antigens (HLA) in humans. Two classes of MHC molecules are known: MHC class I molecules which are expressed on all nucleated cells and MHC class II molecules which are expressed only on APCs. Class I molecules present endogenous protein fragments (not recognized as foreign) and viral antigens (recognized as foreign) while class II molecules present protein fragments derived from proteins that entered the cell by endocytosis or phagocytosis (i.e., proteins which are mainly derived from infectious agents such as parasites and bacteria).

T cells recognize MHC-antigen complexes on APCs via their T cell receptor (TCR)/CD3 complex; the TCR complex together with the CD4 or CD8 coreceptors bind to MHC class II or I, respectively. Occupancy of the TCR alone is not sufficient to active the T cell to respond; activation also requires antigen-independent signals provided by the engagement of costimulatory molecules present on the surface of the T cell with their cognate ligands present on the surface of the APC. The costimulatory proteins serve to stabilize the interaction of the T cell with the APC and to transduce costimulatory signals that lead to the secretion of cytokines, proliferation of the T cell and induction of the T cell's effector function. Engagement of the TCR in the absence of costimulation results in anergy (i.e., nonresponsiveness) of the T cell [Schwartz (1992) Cell 71:1065; Liu and Linsley (1992) Curr. Opin. Immunol. 4:265; Allison (1994) Curr. Opin. Immunol. 6:414 and Linsley and Ledbetter (1993) Annu. Rev. Immunol. 11:191]. In addition to the requirement for costimulatory signals, T cells require growth factors (i.e., cytokines such as interleukin-2) in order to cause proliferation of antigen-reactive T cells.

Several cell surface proteins have been identified as potential costimulatory molecules including LFA-3, ICAM-1 and members of the CD28/CTLA-4 family. The CD28/CTLA-4 family of proteins, present on the surface of T cell, has been shown to be an important costimulator required for interleukin-2 (IL-2) driven proliferation of T cells. The ligands for the CD28/CTLA-4 proteins are members of the B7 family (e.g., B7-1, B7-2 and B7-3).

Cancer immunotherapy aims to induce tumor-specific T cell response that will be effective in the rejection of tumors. The notion that the immune system is naturally involved in identifying and suppressing tumors is supported by the fact that immunocompromised patients have an increased incidence of tumors [Frei et al. (1993) Transplant. Proc. 25:1394]. However, given the incidence of cancer, even in seemingly immunologically normal individuals, it is clear that the immune system fails to recognize and destroy all tumor cells. Indeed animal studies have shown that the majority of tumors fail to provoke an immune response even when these tumors express potentially recognizable tumor-specific antigens [Boon et al. (1994) Annu. Rev. Immunol. 12:337 and Houghton (1994) J. Exp. Med. 180:1]. Several reasons for the lack of immunogenicity of tumor cells have been proposed including failure to express MHC class I molecules, downregulation of transporters for antigen processing and the lack of costimulatory molecules on tumor cells [Garrido et al. (1993) Immunol. Today 14:491; Restifo et al. 91993) J. Exp. Med. 177:265; Cromme et al. (1994) J. Exp. Med. 179:335; Chong et al. (1996) Human Gene Ther. 7:1771].

In order to provide effective cancer immunotherapy, the art needs means to increase the immunogenicity of human tumors as well as animal models predictive of human anti-tumor immune responses.

SUMMARY

The present invention provides novel humanized animal models that permit the identification of immune-modulating genes and combinations thereof useful for the treatment of human tumors. In addition, the present invention provides methods of treating subjects having a tumor with one or more immune-modulating genes and provides tumor cell vaccines comprising tumor cells modified to express immune-modulating genes.

Accordingly, the present invention provides an imniunodeficient mouse comprising human T lymphocytes expressing the CD45 antigen wherein at least 5% of the human T lymphocytes expressing the CD45 antigen represent immature naive T lymphocytes. The invention is not limited by the nature of the immunodeficient mouse strain employed. In a preferred embodiment, the immunodeficient mouse is a SCID/beige mouse.

In another preferred embodiment, the immunodeficient mouse comprising human T lymphocytes further comprising human tumor cells. The invention is not limited by the nature of the human tumor cells employed. The human tumor cells may be established tumor cells, primary tumors cells or tumor cells (established or primary) modified to express one or more immune-modulating genes, genes encoding cell cycle regulators and genes encoding inducers of apoptosis.

In another embodiment, the present invention provides a SCID/beige mouse comprising human immune cells. The invention is not limited by the nature of the human immune cells, these cells may be human PBLs, splenocytes, cells isolated from lymph nodes and/or peritoneal lavage. In a preferred embodiment, the SCID/beige mouse comprising human immune cells further comprising human tumor cells. The invention is not limited by the nature of the human tumor cells employed. The human tumor cells may be established tumor cells, primary tumors cells or tumor cells (established or primary) modified to express one or more immune-modulating genes, genes encoding cell cycle regulators and genes encoding inducers of apoptosis. In a preferred embodiment, the tumor cells are derived from central nervous system cells, most preferably glioblastoma cells. In another preferred embodiment, the tumor cells are malignant melanoma cells.

The present invention further provides a method comprising: a) providing: i) a SCID/beige mouse; ii) human tumor cells; iii) human peripheral blood lymphocytes; b) introducing a first dose of the tumor cells into said mouse; c) reconstituting the mouse containing said tumor cells with the lymphocytes; and d) monitoring the reconstituted mouse for the growth of the tumor cells. The invention is not limited by the nature of the human tumor cells employed. The human tumor cells may be established tumor cells, primary tumors cells or tumor cells (established or primary) modified to express one or more immune-modulating genes, genes encoding cell cycle regulators and genes encoding inducers of apoptosis. In a preferred embodiment, the tumor cells are derived from central nervous system cells, most preferably glioblastoma cells. In another preferred embodiment, the tumor cells are malignant melanoma cells.

In a preferred embodiment, the method further comprises identifying at least one immune modulating gene (or gene encoding a cell cycle regulator or inducer of apoptosis) whose expression prevents the growth of the introduced tumor cells in the reconstituted mouse. In another preferred embodiment, the method comprises, following the reconstitution, the additional step of vaccinating the reconstituted mouse with a second dose of tumor cells. In a preferred embodiment, the first dose of tumor cells comprises unmodified tumor cells and the second dose of tumor cells comprises irradiated tumor cells. In a particularly preferred embodiment, the irradiated tumor cells express at least one immune-modulating gene (or gene encoding a cell cycle regulator or inducer of apoptosis).

In one embodiment of the methods of the present invention, the tumor cells and the lymphocytes come from the same donor. In another embodiment, the tumor cells and the lymphocytes come from different donors.

The present invention further provides a method comprising: a) providing: i) a SCID/beige mouse; ii) irradiated and unirradiated human tumor cells; iii) human peripheral blood lymphocytes; b) reconstituting said mouse with the lymphocytes; c) vaccinating the mouse with the irradiated tumor cells; d) introducing the unirradiated tumor cells into the vaccinated mouse; and e) monitoring the vaccinated mouse for the growth of the unirradiated tumor cells. The invention is not limited by the nature of the irradiated tumor cells. The irradiated tumor cells may be established tumor cells, primary tumors cells or tumor cells (established or primary) modified to express one or more immune-modulating genes, genes encoding cell cycle regulators and genes encoding inducers of apoptosis. In a preferred embodiment, the irradiated and modified tumor cells are derived from central nervous system cells, most preferably glioblastoma cells. In another preferred embodiment, the irradiated and modified tumor cells are malignant melanoma cells.

In a preferred embodiment, the method further comprises identifying at least one immune modulating gene (or gene encoding a cell cycle regulator or inducer of apoptosis) whose expression prevents the growth of said unirradiated tumor cells in said vaccinated mouse.

The present invention also provides a tumor cell vaccine comprising a tumor cell expressing B7-2 and at least one additional immune modulator or a cell cycle regulator or inducer of apoptosis. The vaccines of the present invention are not limited by the nature of the immune modulator or a cell cycle regulator or inducer of apoptosis employed. In a preferred embodiment, the additional immune modulator is a cytokine. The invention is not limited by the nature of the cytokine employed. In a preferred embodiment, the cytokine is selected from the group consisting of interleukin 2, interleukin 4, interleukin 6, interleukin 7, interleukin 12, granulocyte-macrophage colony stimulating factor, granulocyte colony stimulating factor, interferon-gamma, tumor necrosis factor-alpha.

The present invention provides a method of treating a tumor comprising: a) providing: i) a subject having a tumor of the central nervous system; ii) an expression vector encoding the human B7-2 protein and at least one additional immune modulator or a cell cycle regulator or inducer of apoptosis; b) transferring the expression vector into the tumor under conditions such that the B7-2 protein and the immune-modulator (and/or a cell cycle regulator or inducer of apoptosis) are expressed by at least a portion of the tumor. In a preferred embodiment, the method further comprises, prior to transfer of the expression vector, the step of removing at least a portion of the tumor from the subject and following the transfer of said expression vector, irradiating the tumor cells expressing the B7-2 protein and the immune-modulator (and/or a cell cycle regulator or inducer of apoptosis) and introducing the irradiated tumor cells back into the subject to create an immunized subject. In another embodiment, the method further comprises introducing at least one additional dose of irradiated tumor cells expressing the B7-2 protein and the immune-modulator (and/or a cell cycle regulator or inducer of apoptosis) into the immunized subject.

For FIGS. 2A–2D, the histograms on the left represent D54MG cells stained with isotype matched control antibodies while the histograms on the right represent staining with monoclonal anti-human B7-2 antibodies.

Figure 2A:
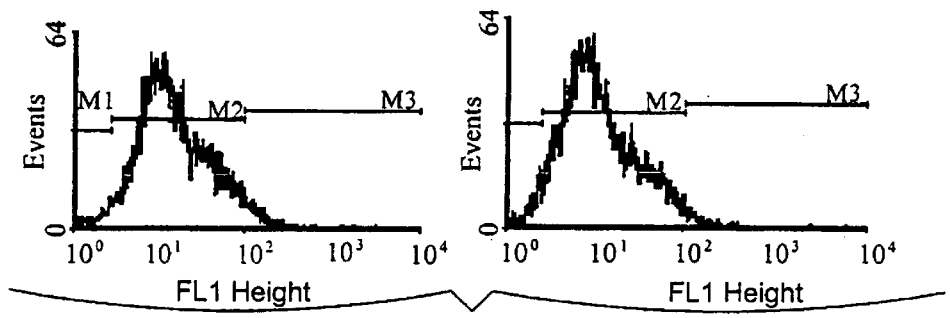
FIGS. 2A–E provide flow cytometry histograms for wild type D54MG cells (2A), B7-2-transduced D54MG cells (2B), GM-C SF-transduced D54MG cells (2C), B7-2 and GM-CSF-transduced D54MG cells (2D), and GFP-transduced D54MG cells (2E).
Figure 2B:
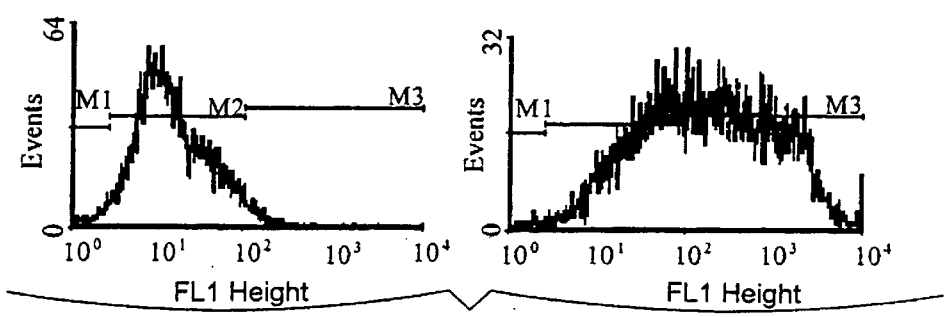
Figure 2C:
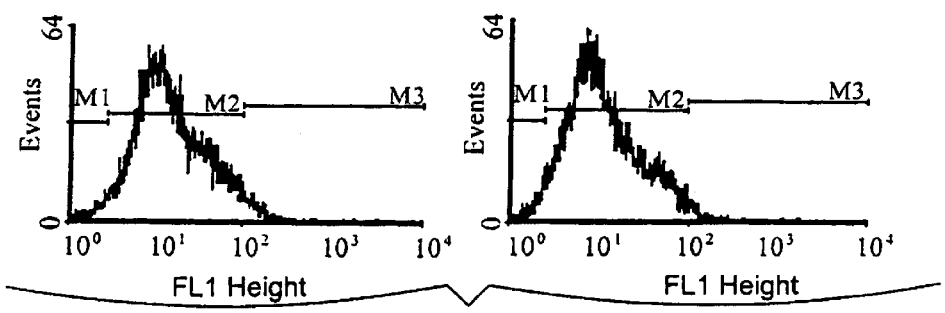
Figure 2D:
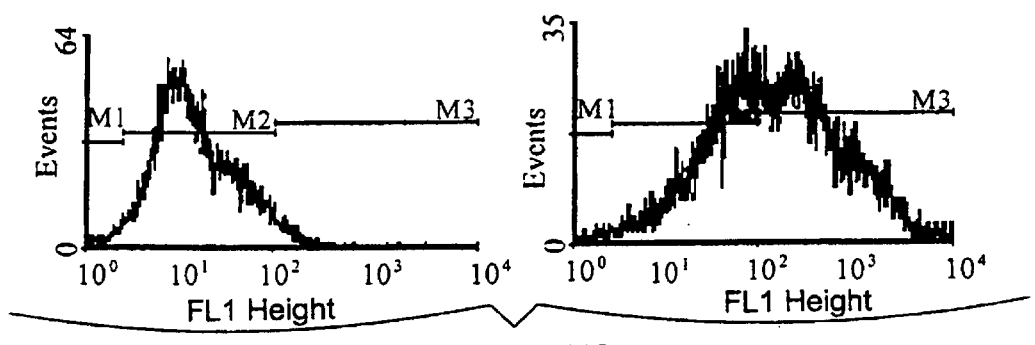
Figure 2E:
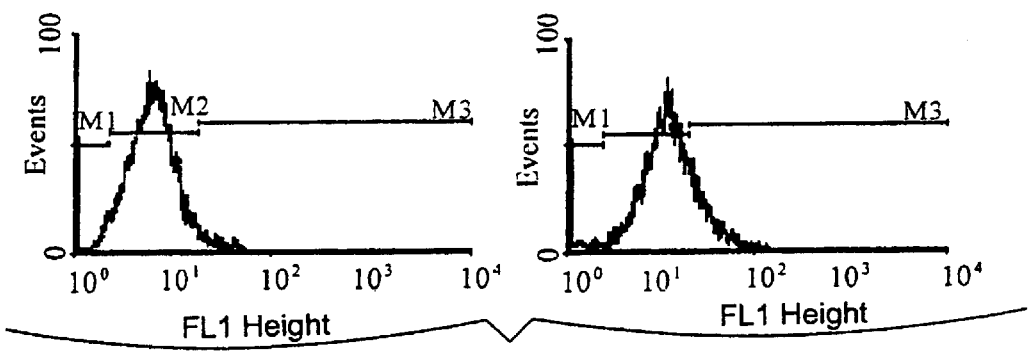

For FIG. 2E, the histogram on the left represents unstained wild type D54MG cells while the histogram on the right represents unstained GFP-transduced D54MG.

Figure 3A:
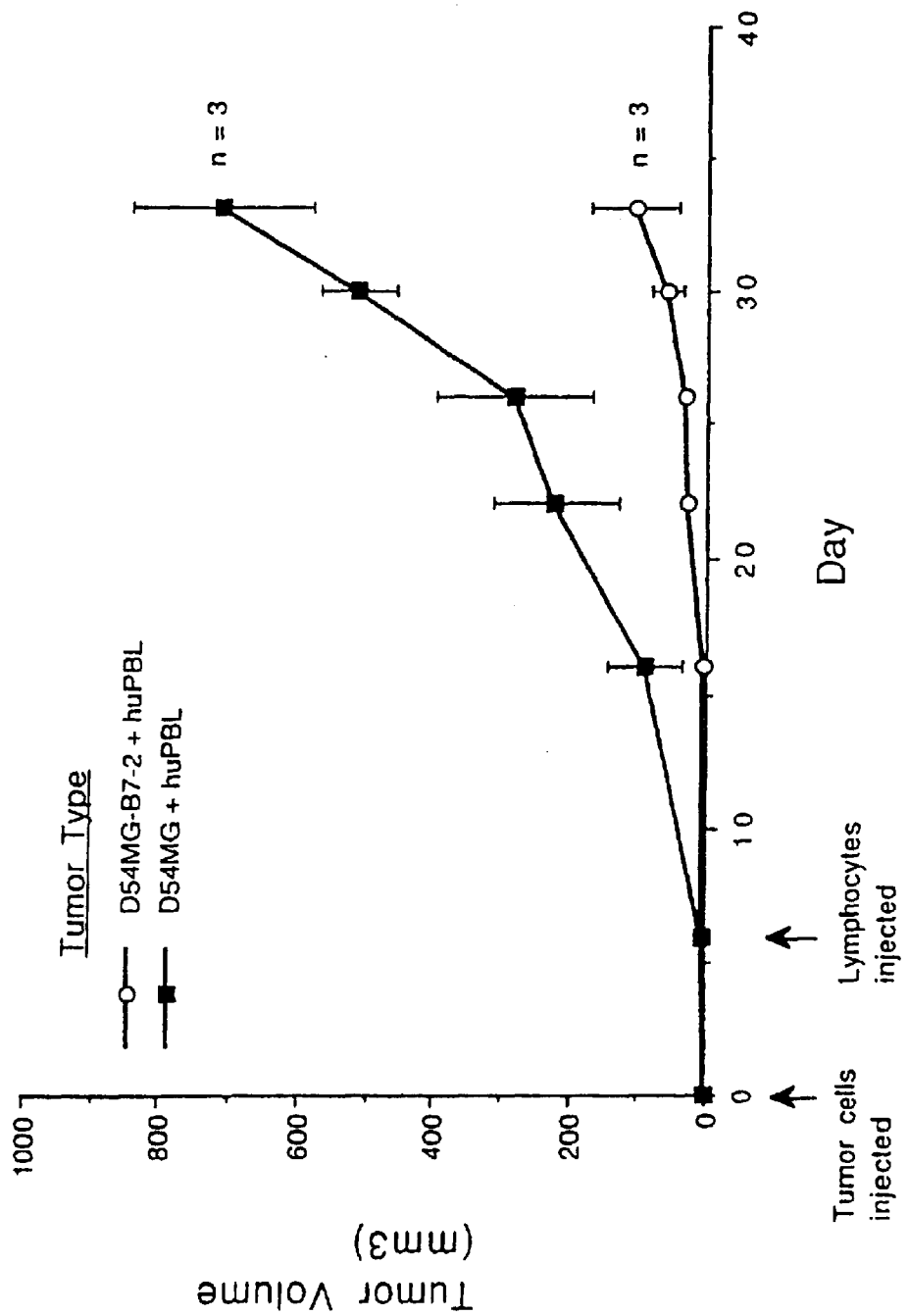
Figure 3B:
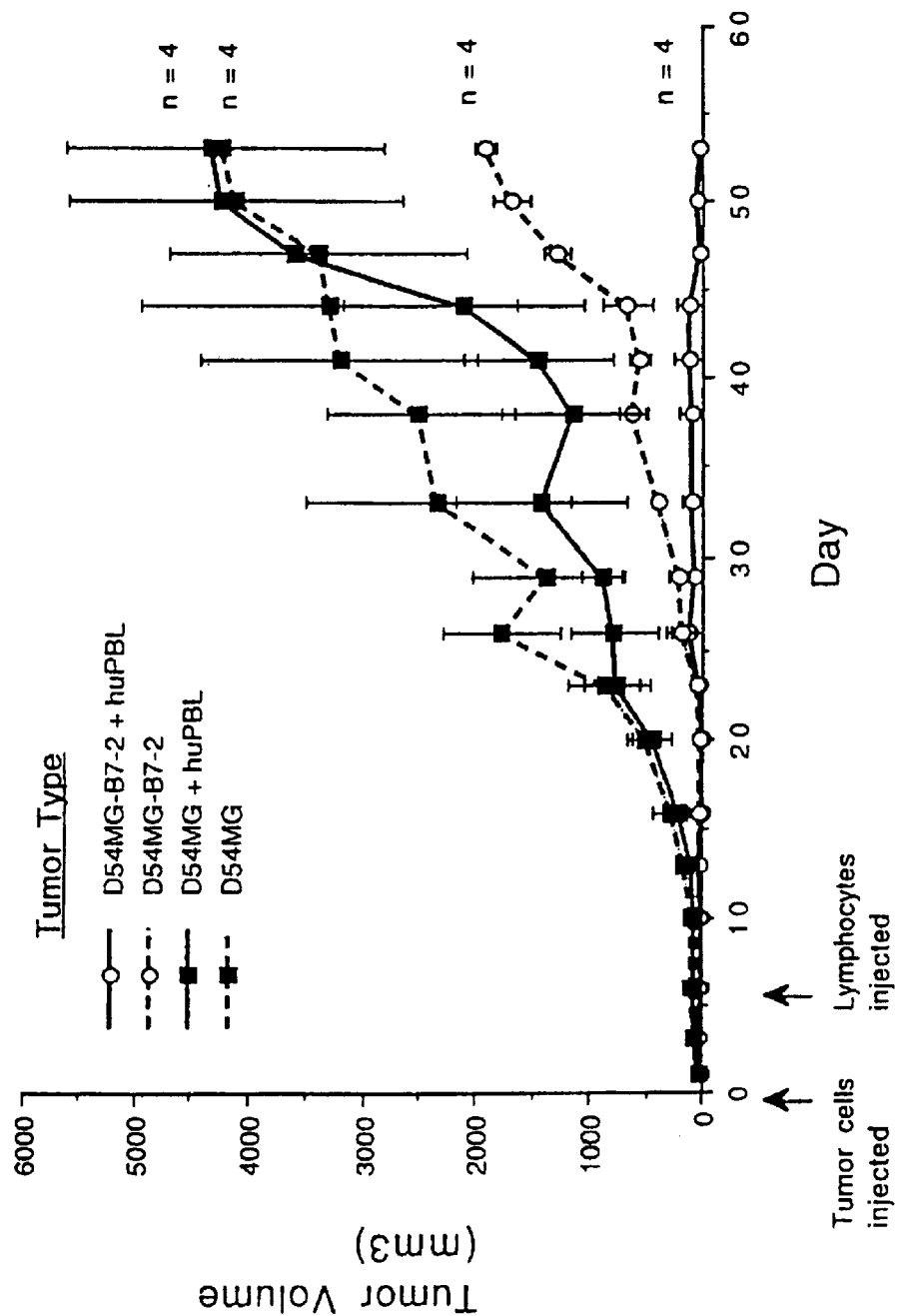

FIGS. 3A and 3B show the inhibition of growth of B7-2-transduced D54MG cells compared to unmodified D54MG cells in Hu-PBL-SCID/bg mice. In FIG. 3A, all mice were reconstituted with PBLs while in FIG. 3B half the mice from both groups were left unreconstituted.

Figure 4A:
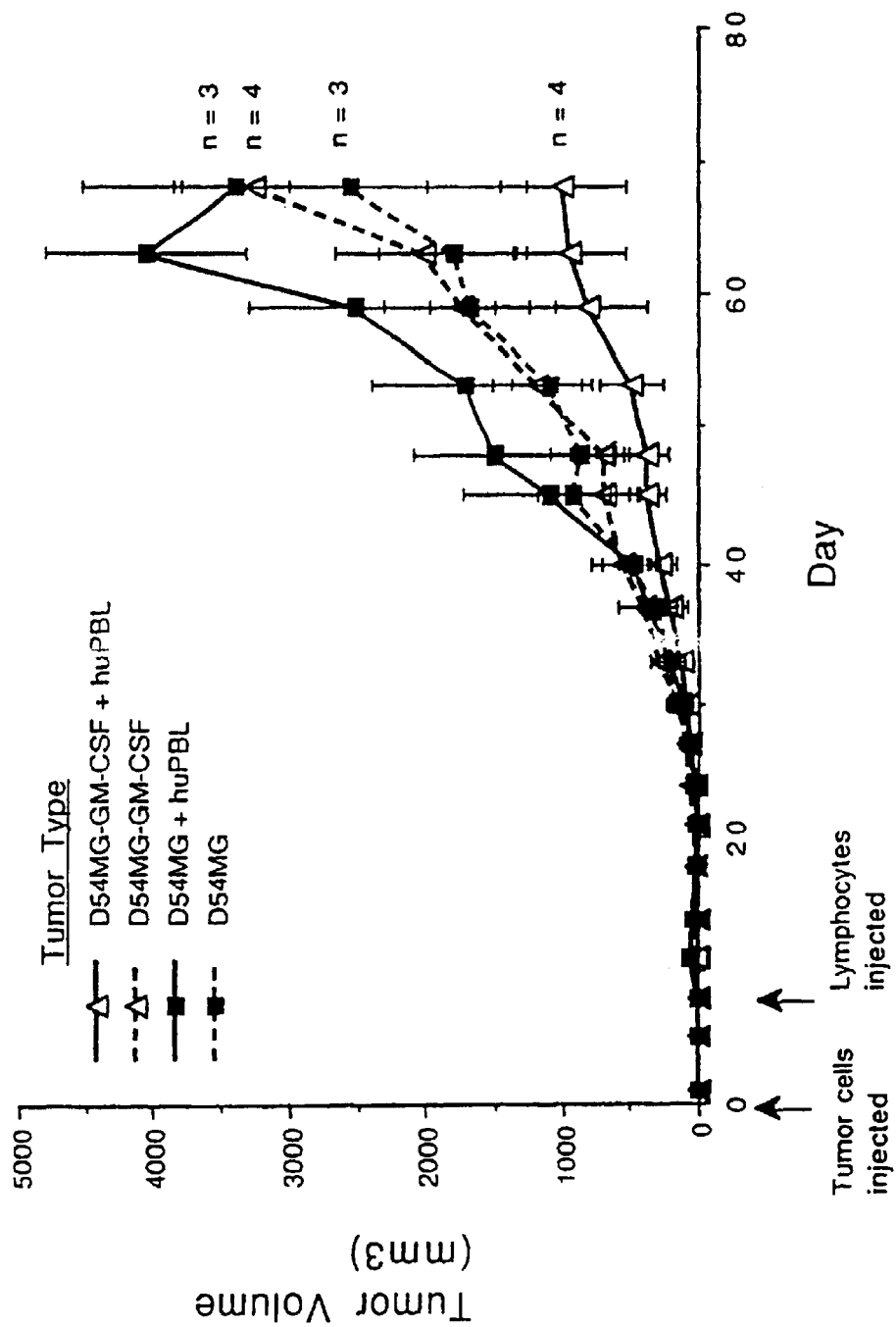
Figure 4B:
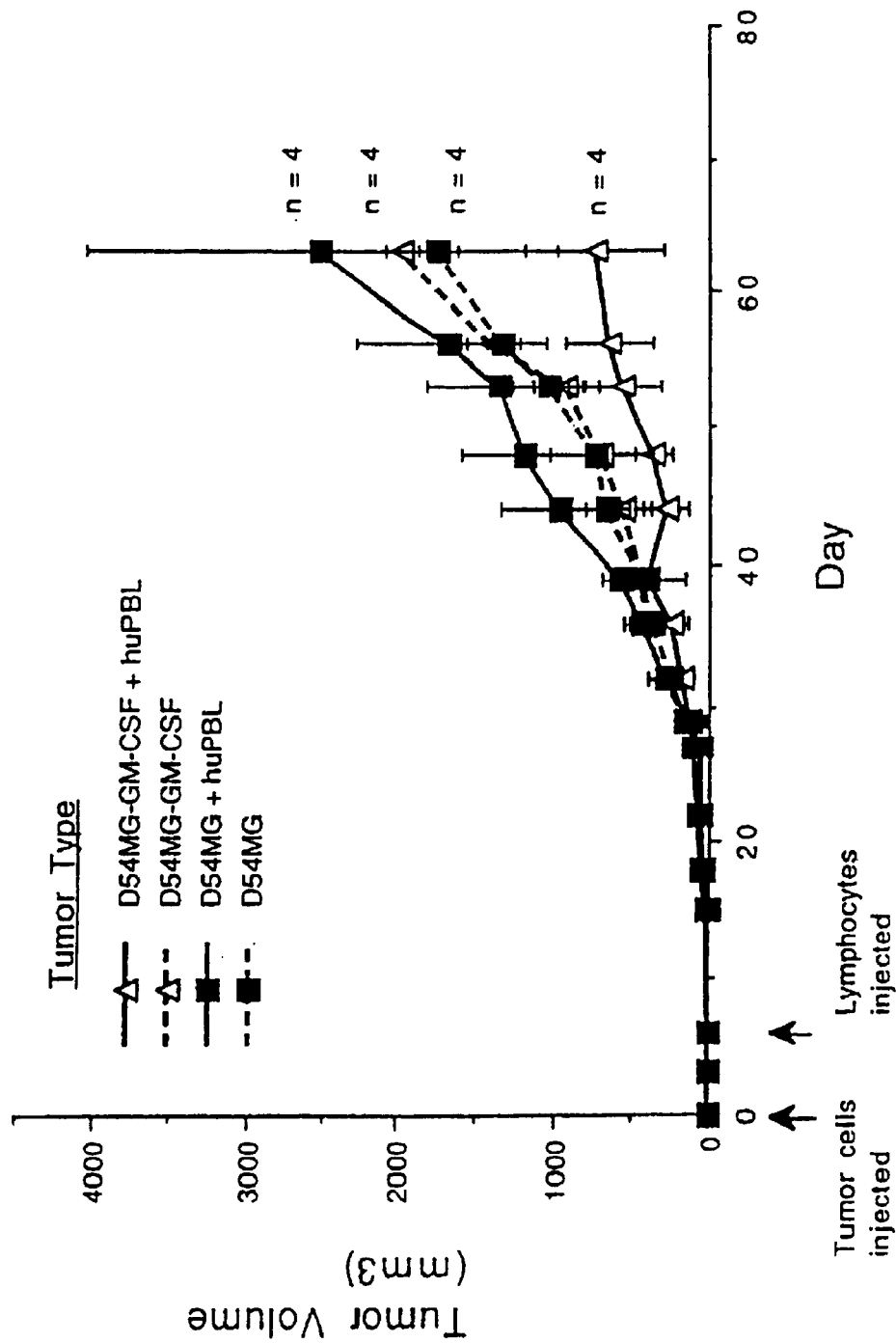

FIGS. 4A and 4B show the inhibition of growth of GM-CSF-transduced D54MG cells compared to unmodified D54MG cells in Hu-PBL-SCID/bg mice. FIGS. 4A and 4B represent data from two separate experiments.

Figure 5A:
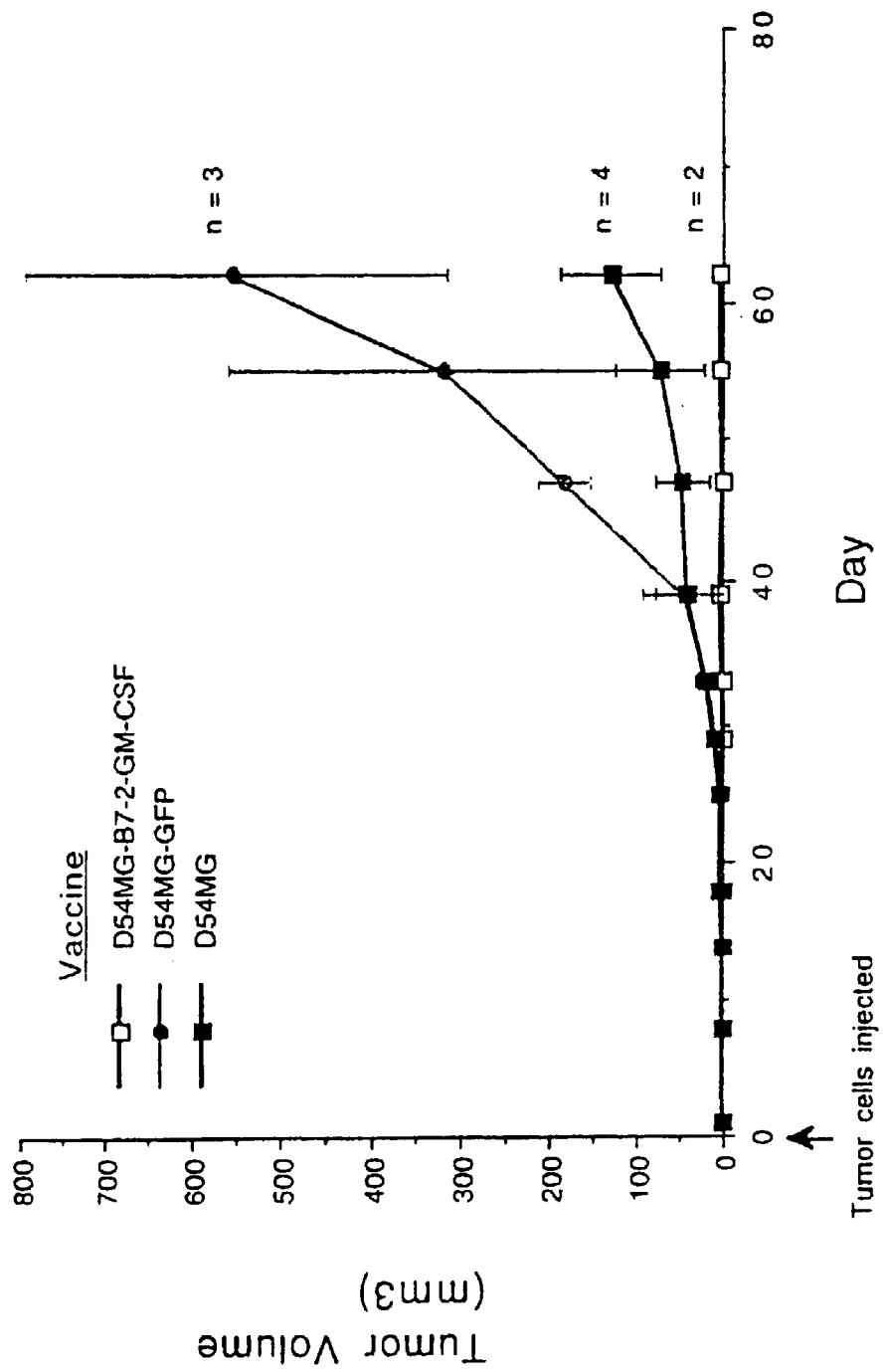
Figure 5B:
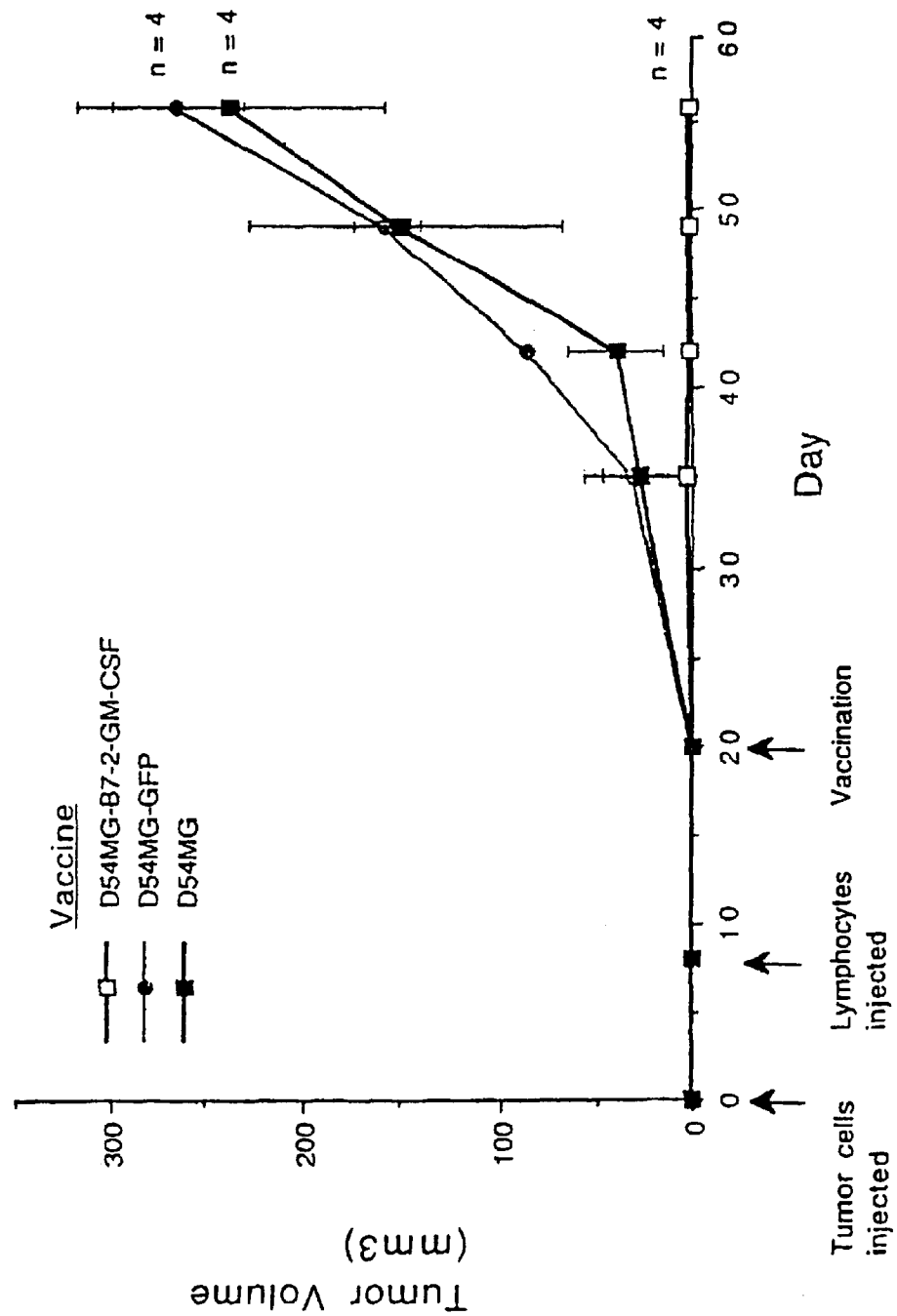

FIGS. 5A and 5B show the inhibition of unmodified D54MG cell challenges in Hu-PBL-SCID/nod mice (5A) and Hu-PBL-SCID/bg mice (5B) vaccinated with irradiated D54MG-B7-2/GM-CSF cells.

DEFINITIONS

To facilitate understanding of the invention, a number of terms are defined below.

As used herein, "immunodeficient mouse" refers to a mouse or mouse strain which is deficient in immune system function, including at least a deficiency in function or presence of mature B and T lymphocytes. Examples of immunodeficient mouse strains include, but are not limited to the C.B-17-SCID-nod, C.B-17scid/scid and C.B-17-SCID-beige strains. Particularly preferred immunodeficient mice have a severe combined immunodeficiency characterized by a lack of mature T, B and natural killer (NK) lymphocytes (e.g., the C.B-17-SCID-beige mouse strain). As used herein, "human T lymphocytes" refers to T lymphocytes of human origin. When present in a mouse reconstituted with human blood cells, the human T lymphocytes may be obtained from a variety of sources in the reconstituted mouse including blood (i.e., peripheral blood lymphocytes or PBLs), lymph nodes, spleen, peritoneal lavage, etc.

Human T lymphocytes are identified by the presence of certain markers or cell surface proteins including CD3, CD4, CD8, T cell antigen receptor (TCR) and CD45. The presence of these markers on a lymphocyte may be determined by standard immunocytological means such as incubation (or staining) of a cell suspension containing lymphocytes with antibodies specific for these markers; the antibodies may be directly labelled (e.g. with a fluorophore such as fluorescein, phycoerythrin, Texas Red, etc.) or the presence of the antibody bound to the surface of a lymphocyte may be detected using a secondary antibody (i.e., an antibody directed at the first antibody or a component thereof) that is labelled. The stained lymphocytes may then be analyzed using a fluorescence microscope or a FACS (fluorescence-activated cell sorter) analysis. "Mature human T lymphocytes" express either CD4 or CD8, CD3 and a TCR. "Imma-ture human T lymphocytes" express both CD4 and CD8 (i.e., they are CD4+8+); these cells are also referred to as progenitor T cells. "Immature naive human T lymphocytes" are immature T lymphocytes that have not been activated (i.e., they have not engaged antigen specific for their TCR or been stimulated by a nonspecific mitogen) and are said to be naive. "Immature naive T lymphocytes" includes CD4+8+T cells as well as CD45RA+T cells.

A mouse comprising CD45+T lymphocytes wherein at least 5% of the human CD45+T cells represent immature naive T lymphocytes is a mouse in which 5% or more of the CD45+T cells are either CD4+8+ or CD45RA+ or the sum of the % of CD45+T cells that are CD4+8+ and CD45RA+ is at least 5%.

CD45 proteins are found on the surface all hematopoietic cells, except for erythrocytes [The Leukocyte Antigen Facts Book, Barclay et al. (1993), Academic Press, London, UK, pp. 202–204]. Different isoforms of CD45 are found on different lymphoid cell types; CD45RO is found on activated and memory T cells, whereas CD45RA is found on naive T cells.

The term "SCID/beige mouse" refers to the C.B-17-SCID-beige mouse strain. The terms SCID/beige, SCID-beige and SCID/bg are used interchangeably herein.

The term "human tumor cells" refers to tumor cells of human origin; a tumor cell is a neoplastic or cancerous cell. Tumor cells may be "established tumor cells," i.e., those which can be maintained indefinitely in tissue culture or may be "primary tumor cells," i.e., tumor cells freshly isolated or explanted from a patient. The term "primary tumor cells" encompasses primary tumor cells maintained in tissue culture for less than or equal to 5 passages.

The term "human immune cell" refers to cells of the immune system (e.g., T, B and NK lymphocytes, antigen presenting cells) that are of human origin.

The term "human peripheral blood lymphocytes" refers to nucleated, non-erythroid cells derived from the blood of a human. The terms peripheral blood lymphocytes (PBLs) and peripheral blood mononuclear cells (PBMCs) are used herein interchangeably.

The term "central nervous system cells" refers to cells derived from the central nervous system (i.e., cells derived from the brain and spinal cord).

A mouse "reconstituted with human peripheral blood lymphocytes" is a mouse in which human PBLs have been introduced (e.g., by intraperitoneal injection) and persist for a period of at least 4 weeks.

An "immune-modulating gene" is a gene encoding a protein that modulates the immune response. Examples of immune-modulating genes include but are not limited to cytokines, costimulatory molecule and chemotactins. The product of an immune-modulating gene is said to be an "immune modulator." A "cytokine" is a hormone-like protein, typically of low molecular weight, that regulates the intensity and duration of the immune response and is involved in cell to cell communication. Examples of cytokines include but are not limited to the interleukins (e.g., interleukin 2, interleukin 4, interleukin 6, interleukin 7, interleukin 12), granulocyte-macrophage colony stimulating factor, granulocyte colony stimulating factor, interferon-gamma (IFN-γ) and tumor necrosis factor-alpha (TNF-α).

The term "cell cycle regulator" refers to any protein whose activity modulates progression of the cell cycle. Particularly preferred cell cycle regulators are those that block cell cycle progression. Examples include but are not limited to the HIV vpr gene product, p21, inhibitors of mammalian cyclins, etc.

The term "inducer of apoptosis" refers to any protein whose activity induces apoptosis in a cell. Inducers of apoptosis include but are not limited to apoptin (the product of the chicken anemia virus VP3 gene), BAX, BAD, a BCL-X derivative and the HIV vpr gene product.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

Transcriptional control signals in eucaryotes comprise "promoter" and "enhancer" elements. Promoters and enhancers consist of short arrays of DNA sequences that interact specifically with cellular proteins involved in transcription [Maniatis, et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss, et al., Trends Biochem. Sci., 11:287 (1986) and Maniatis, et al., supra (1987)]. For example, the SV40 early gene enhancer is very active in a wide variety of cell types from many mammalian species and has been widely used for the expression of proteins in mammalian cells [Dijkema, et al., EMBO J. 4:761 (1985)]. Two other examples of promoter/enhancer elements active in a broad range of mammalian cell types are those from the human elongation factor 11a gene [Uetsuki et al., J. Biol. Chem., 264:5791 (1989); Kim et al., Gene 91:217 (1990); and Mizushima and Nagata, Nuc. Acids. Res., 18:5322 (1990)] and the long terminal repeats of the Rous sarcoma virus [Gorman et al., Proc. Natl. Acad. Sci. USA 79:6777 (1982)] and the human cytomegalovirus [Boshart et al., Cell 41:521 (1985)].

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site [Sambrook et al., Molecular Cloning: A Laboratory Manual, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient potyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation [Sambrook, supra, at 16.6–16.7]. This 237 bp fragment is contained within a 671 bp BamHI/PstI restriction fragment.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with TK cell lines, the carbamoyl-phosphate synthetase-aspartate transcarbamoylase-dihydroorotase (CAD) gene which is used in conjunction with CAD-deficient cells and the mammalian hypoxanthine-guanine phosphoribosyl transferase (hprt) gene which is used in conjunction with HPRT$^-$ cell lines. A review of the use of selectable markers in mammalian cell lines is provided in Sambrook et al., supra at pp. 16.9–16.15. It is noted that some selectable markers can be amplified and therefore can be used as amplifiable markers (e.g., the CAD gene).

DESCRIPTION OF THE INVENTION

The present invention provides humanized animal models suitable for the evaluation of anti-human tumor immunity. These animal models permit the identification of combinations of immune-modulating genes (IMGs) which when delivered to human tumor cells induce an effective anti-tumor response, including a systemic anti-tumor response. The Description of the Invention is divided into the following sections: I. Immunogene Therapy; II. Existing Animal Models For Immunogene Therapy; Ill. The Hu-SCID/beige Model For Immunotherapy; and IV. Combination Immunogene Therapy.

I. Immunogene Therapy

Immunogene therapy involves the introduction of genes encoding proteins that regulate or modulate the immune response and particularly those that are involved with the activation of T cells. As discussed above, the majority of tumors are not immunogenic, i.e., they fail to provoke an immune response. Several reasons for the lack of immunogenicity of tumor cells have been proposed including the lack of cell surface molecules on the tumor cell that are required to transduce costimulatory signals that are required in order for T cells to secrete cytokines, proliferate, induce effector function and prevent anergy. As most tumor cells are not derived from professional APCs which normally present antigen and provide costimulatory signals to T cells, it is not surprising that the majority of tumor cells fail to induce a tumor-specific response even when the tumor cell bears a tumor-specific antigen.

In an attempt to increase the immunogenicity of tumor cells, genes encoding co-stimulatory proteins and/or cytokines have been introduced into tumor cells. The modified tumor cells are then examined for their ability to induce an anti-tumor response (in vivo or in vitro). As discussed below, these experiments have been carried out in animal models (e.g., in mice and rats) and the results have been conflicting leading some in the field to question the utility of existing animal models for the development of immunogene therapy protocols aimed at the treatment of humans.

II. Existing Animal Models for Immunogene Therapy

The majority of the existing animal models for immunogene therapy involve the use of immunocompetent syngeneic animals (e.g., mice and rats) and established tumor cell lines. Typically, one immunogene (e.g., mouse L-2) is introduced into an established mouse tumor cell line, the tumor cells are selected in culture to identify cells expressing the transferred immunogene and the modified tumor cells are injected into recipient mice and the mice are examined for the presence of tumors. In some experiment, the mice receive irradiated modified tumor cells as a vaccine followed by a challenge with unmodified tumor cells (vaccination/challenge experiment). In some cases, the expression of certain immunogenes has been shown to increase the immunogenicity of the tumor cell (i.e., to reduce the tumorigenicity of the tumor cell). An experimentally induced animal tumor is said to be immunogenic if the tumor is rejected following transplantation into syngeneic animals previously immunized or vaccinated with irradiated cells of the same tumor. Nonimmunogenic tumors are not rejected under these conditions.

Overall the results of these syngeneic animal experiments have been conflicting. For example, the expression of the costimulatory molecule B7-1 in the mouse melanoma cell line B-16 was found to lead to the rejection of B7-1 expressing B-16 cells in syngeneic mice in one study [Wu et al (1995) J. Exp. Med. 182:1415] while in another study B7-1-expressing B-16 cells were found to be tumorigenic [Chen et al. (1994) J. Exp. Med. 179:523]. In the case where B7-1 expression was found to increase the immunogenicity of B-16 cells, the authors reported that animals that rejected the modified B-16 cells did not develop an enhanced systemic immunity against unmodified or wild type B-16 cells [Wu et al., supra]. In another study, the expression of B7-1 or B-72 in mouse colorectal tumor or melanoma cells was found to confer a local anti-tumor response in immunocompetent mice [Chong et al. (1996) Human Gene Ther. 7:1771]. However, no systemic immunity was conferred by vaccination of mice with B7-1 or B7-2 expressing colorectal tumor cells and the expression of B7-1 or B7-2 in the melanoma cells was found to reduce the systemic immunity conferred by the B7-expressing cells relative to that conferred by vaccination with wild type melanoma cells even when the B7-expressing cells also expressed interferon-y (Chong et al., supra).

It has been reported that the rejection of B7-1 expressing tumor cell lines is limited to highly immunogenic cell lines as B7-1 expression in poorly immunogenic fibrosarcomas (e.g., MAC101, MCA102 and Ag104) and the B-16 melanoma cell line does not reduce the tumorigenicity of these lines. As discussed above, expression of B7-1 in the B-16 melanoma cell line was found by one group to reduce the tumorigenicity of these cells (Wu et al., supra). This discrepancy may be explained by differences in the level of B7-1 expression achieved by different groups. However, tumor cells expressing only B7-1 have been found to be ineffective in inducing the rejection of established tumors.

The failure of B7-1 alone to induce the rejection of established tumors was postulated to be due to the induction of a state of anergy in potentially reactive T cells. Therefore, combinations of B7-1 and cytokines were tested to see if this state of anergy could be overcome. Combinations of costimulatory molecules and various growth factors or cytokines has proven to be more effective than the use of either category of molecules alone. For example, the expression of B7-1 in the mouse NC adenocarcinoma cell line was found to have no effect on the tumorigenicity of these cells in immunocompetent syngeneic mice [Gäken et al. (1997) Human Gene Ther. 8:477]. However, the expression of both B7-1 and IL-2 in the NC adenocarcinoma cell line substantially reduced the tumorigenicity of these cells in mice.

While existing animal models have demonstrated that in general a combination of costimulatory molecules and a cytokine and/or a chemokine is preferable to the use of any one of these groups alone, the data from different groups using combinations of these molecules is conflicting. For example, Dilloo et al. reported that mice immunized with A20 B cell lymphoma cells mixed with IL-2 and the chemokine lymphotactin developed a potent anti-tumor response while mice immunized with B cell lymphoma cells mixed with GM-CSF developed a much reduced anti-tumor response [Dilloo et al. (1996) Nature Med. 2:1090]. On the other hand Levitsky et al., reported that vaccination of mice with GM-CSF-expressing A20 B lymphoma cells lead to a complete rejection of pre-established A20 tumors while vaccination with either 11-2-expressing or B7-1-expressing A20 cells did not [Levitsky et a. (1996) J. Imunol. 156:3858]. This apparent conflict lead Dilloo and Brenner to remark that "it [is] difficult to be confident that current murine models can be used to pick the "best" cytokine for a particular human tumor." [Nature Med. (1997) 3:126]. Clearly the art needs improved models for determining which cytokines, costimulatory molecules and/or chemotactins, or which combination thereof is best suited for the treatment of particular human tumors.

III. The Hu-PBL-SCID/Beige Model for Immunotherapy

The present invention provides novel humanized animal models for human immunogene therapy. As discussed above, most preclinical immunogene therapy studies have employed murine genes and murine tumor models. The applicability of such models to humans systems is unclear. Therefore, a humanized mouse model utilizing human tumor cells (either established cell lines or primary tumor cells), human immunogenes and human lymphocytes was developed and is provided herein.

The C.B-17 SCID/beige (SCID/bg) mouse, an immunocompromised mouse, was employed for the humanized mouse model as this strain of mice lacks T cell, B cell and natural killer (NK) cell function [Froidevaux and Loor (1991) J. Immunol. Methods 137:275]. As shown herein, the SCID/bg mouse supports the growth of a variety of established human tumor cell lines as well as primary human tumor cells. SCID/bg mice were efficiently reconstituted with human peripheral blood lymphocytes (PBLs) with CD45+human cells constituting up to 60% of the splenocytes and 2–7% of the peripheral blood mononuclear cells in the reconstituted mice.

Importantly, the peripheral blood of the Hu-PBL-SCID/bg mice were found to contain high numbers of immature or progenitor T cells (i.e., CD4+8+ cells and CD45RA+ cells). These results are in contrast to the results obtained by reconstitution of C.B-17scid/scid mice (Hu-PBL-SCID). In human PBL-reconstituted C.B-17 scid/scid mice, most human lymphocytes exhibit activated cell phenotypes (HLA-DR+ and CD25+ or CD69+) soon after reconstitution, and almost all (>99%) human T cells exhibit mature memory phenotypes (CD45RO+) in a state of reversible anergy [Rizza et al. (1996) J. Virol. 70:7958; Tarry-Lehmann and Saxon (1992) J. Exp. Med. 175:503; Tarry-Lehmann et al. (1995) Immunol. Today 16:529]. Therefore, the lack of sufficient numbers of immature naive T cells after reconstitution renders the Hu-PBL-SCID model unsuitable for the evaluation of anti-tumor immunity. In contrast, the Hu-PBL-SCID/bg mice show evident levels of CD45RA+ and CD4+8+ cells 4–6 weeks after reconstitution. Thus, the Hu-PBL-SCID/bg mice of the present invention provide a suitable model for the evaluation of anti-tumor immunity.

The use of the Hu-PBL-SCID/bg mice as a model for human immunogene therapy is illustrated herein for the identification of a combination of immune-modulating genes (IMGs) effective in the treatment of human glioblastoma inultiforme. Glioblastoma multiforme is the most common primary central nervous system neoplasm in humans. Despite improvements in diagnosis and treatment of glioblastoma multiforme, mean survival from time of diagnosis remains less than one year [Chang et al. (1983) Cancer 52:997; McDonald and Rosenblum (1994) In: *Principles of Neurosurgery*, Regachary and Wilkins, eds., Wolfe Publishing, Toronto, pp. 26.21–26.32].

Although glioblastomas in situ are normally infiltrated to varying degrees by lymphocytes [Kuppner et al. (1989) J. Neurosurgery 71:211; Black et al. (1992) J. Neurosurgery 77:120], evidence indicates these lymphocytes are unactivated. This may be in part due to secretion of immunosuppressive factors such as prostaglandin $E_2$, transforming growth factor $\beta_2$, and interleukin-10, all of which inhibit lymphocyte activation [Fontana et al. (1982) J. Immunol. 129:2413; Siepl et al (1988) Eur. J. Immunol. 18:593; Kuppner et al., supra; Sawamura et al. (1990) J. Neuro-Oncol. 9:125; Nitta et al. (1994) Brain Res. 649:122; Huettner et al. (1995) Am. J. Pathol. 146:317]. Immunogene therapy strategies were designed to overcome such local immunosuppression by promoting tumor antigen presentation and/or anti-tumor lymphocyte activation.

As discussed above, most preclinical immunogene therapy studies have used rodent genes and rodent tumor models. However, the applicability of such models to human systems is unclear. This is particularly true for glioblastoma models utilizing rodent tumors (rat 9L-glioma and C6-glioma) which have sarcomatous features that are significantly different from human glioblastoma multiforme [Benda et al. (1968) Science 161:370; Barker et al. (1973) Cancer Res. 33:976; Day and Bigner (1973) Cancer Res. 33:2362]. Therefore, the present invention provides a novel humanized mouse model utilizing a human glioblastoma cell line, human immunogenes and human lymphocytes.

Using retroviral vectors, genes encoding human GM-CSF and/or B7-2 were efficiently transferred in vitro into a human glioblastoma cell line. Thereafter, the effect of GM-CSF and/or B7-2 expression on glioblastoma growth in vivo was examined in a human tumor/human PBL/severe combined immunodeficiency mouse (hu-PBL-SCID) model. Human glioblastoma cells (with or without therapeutic gene transfer) and human PBLs were grafted into SCID/bg or SCID/nod mice and the effect on tumor growth locally and at distant sites was observed. SCID/bg and SCID/nod mice accept human tumor and lymphocyte grafts without rejection as they lack mature T, B, and NK lymphocytes.

As shown herein, inhibition of GM-CSF and B7-2-transduced tumors was seen in human lymphocyte-reconstituted SCID/bg mice demonstrating that expression of these genes by glioblastoma cells overcomes local immunosuppression and results in a significant antitumor immune response. Furthermore, inhibition of wild type challenge growth in mice vaccinated with irradiated tumor cells transduced with B7-2 and GM-CSF demonstrated that expression of these genes by glioblastoma cells induced a systemic immune response that inhibits tumor growth at distant sites. These results provide the first in vivo demonstration of human GM-CSF immunogene therapy in a human glioblastoma model.

The human glioblastoma-Hu-PBL-SCID/bg model employed herein represents an allogeneic system that comprises an established human glioblastoma cell line and lymphocytes from unrelated donors. This model has more similarities to autologous systems than may be immediately apparent. Unlike the classical immune-mediated rejection seen in allogeneic organ transplantation, this system is free of graft-origin "passenger lymphocytes." These lymphocytes are important in initiating allogeneic organ rejection responses by presenting antigen to host lymphocytes in the context of allogeneic Class II Major Histocompatibility Complex (MHC) [Larsen et al. (1990) Annals Surgery 212:308; Chandler and Passaro (1993) Archives Surg. 128:279; Moller (1995) Transplantation Proc. 27:24]. The D54MG glioblastoma cell line employed in this model expresses only Class I MHC and not Class II MHC in vitro. Therefore, the only Class II MHC molecules available for tumor antigen presentation in this model are those present on engrafted human PBLs. In other words, this model glioblastoma system is allogeneic for Class I MHC but autologous for Class II MHC.

As described herein, the human tumor/Hu-PBL-SCID/bg model can be used as an autologous model system comprising human tumor cells and PBLs from the same patient. Such an autologous model is preferred to an allogeneic model system; however, for certain rapidly progressing tumors it may be difficult to obtain PBLs from the same patient once the patient's tumor has been established in the Hu-PBL-SCID mice. In these cases, an allogeneic model, using PBLs from a donor unrelated to the tumor donor is employed.

The human tumor/Hu-PBL-SCID/bg model of the present invention provides a simple and powerful method to analyze human lymphocyte responses to human tumors in vivo and thus provides a means to determine which combination of IMGs are best suited for the treatment of specific tumors.

IV. Combination Immunogene Therapy

The human tumor/Hu-PBL-SCID/bg model of the present invention provides a simple and powerful method to determine which combination of IMGs or IMGs and/or cell cycle regulators, inducers of apoptosis and tumor suppressor genes (e.g., the wild type p53 gene) are best suited for the treatment of specific tumors.

Many immunomodulatory genes are potentially useful and more than one may be necessary for overcoming tumor immunosuppression. These include genes encoding cytokines, major histocompatibility complex molecules, and T cell costimulatory molecules [Dranoff et al. (1993) Proc. Natl. Acad. Sci. USA 90:3539; Gajewski et al. (1995) J. Immunol. 154:5637]. An ideal tumor vaccine should coexpress a combination of immunostimulatory genes from distinct immunomodulatory pathways (e.g., costimulators, cytokines, and chemoattractive adjuvants) and may also express cell cycle regulators, inducers of apoptosis and tumor suppressor genes.

In the illustrative example provided herein, a combination of the therapeutic cytokine granulocyte-macrophage colony stimulating factor (GM-CSF) and the T cell costimulatory molecule B7-2 was employed to increase the immunogenicity of a human glioblastoma cell line.

GM-CSF stimulates growth and differentiation of granulocytes, monocytes/macrophages, microglia, and other antigen presenting cells. It has recently come into widespread clinical use as a treatment of neutropenia due to its hematopoietic effects [Lieshcke and Burgess (1992) N. Engl. J. Med. 327:28; Aglietta et al. (1994) Seminars Oncol. 21:5; Engelhard and Brittinger (1994) Seminars Oncol. 21:1]. The importance of this cytokine in tumor immunogene therapy was recently demonstrated by Dranoff, et al. who showed that vaccination with irradiated GM-CSF-transduced tumor cells produced specific and marked growth inhibition of wild type tumor challenges in mouse models of adenocarcinoma and melanoma [Dranoff et al., supra]. Of 10 cytokine genes tested, GM-CSF resulted in the greatest tumor growth inhibition in this mouse model.

B7-2 is one of a family (B7-1, B7-2, and B7-3) of lymphocyte cell surface molecules that have recently been identified as costimulatory molecules necessary for T-cell activation in conjunction with antigen presentation in the context of a major histocompatibility complex molecule. The absence of costimulatory molecules on tumor cells may contribute to their failure to be detected and eliminated by the immune system [Galea-Lauri et al. (1996) Cancer Gene Ther. 3:202]. The specific roles of the various costimulatory molecules are yet to be clearly defined. It has been suggested that B7-1 expression promotes differentiation of intermediate $T_H$ cell precursors into $T_H1$ effector cells (cellular immune responses) while B7-2 expression leads to $T_H2$ differentiation (humoral immune responses) [Kawamura and Furue (1995) Eur. J. Immunol. 25:1913; Thompson (1995) Cell 71:979]. However, both B7-1 and B7-2 have been shown to promote cell mediated immune responses in animal models [Hodge et al. (1994) Cancer Res. 54:5552; Lanier et al. (1995) J. Immunol. 154:97; Plumas et al. (1995) Eur. J. Immunol. 25:3332]. More recently, the effectiveness of B7-1 expression in promoting tumor rejection has been questioned (Wu et al., supra). Furthermore, T cells must receive costimulatory signals from APCs within the first 12 hours of T cell receptor stimulation for maximal interleukin-2 production [Mondino and Jenkins (1994) J. Leuckocyte Biol. 55:805]. Therefore, the rapid induction of B7-2 (not B7-1) on APC's after antigen stimulation suggests that B7-2 is the preferable costimulatory molecule to promote antitumor cell-mediated immune responses (Galea-Lauri et al., supra).

Other IMGs to be examined for their effectiveness in treating human tumors in the novel animal models of the present invention include, but are not limited to, APO-1 (Fas), APO-1 ligand (FasL) [Hahne et al. (1996) Science 274:1363; Seino et al. (1997) Nature Med. 3:165; Strand et al. (1996) Nature Med. 2:1361], IL-12A and IL-12B, IL-2, IL-4, IL-6, IL-7, IL-10, GM-CSF, G-CSF, IFN-γ, CD40 and TNF-α. In addition, genes encoding cell cycle regulators or inducers of apoptosis may be employed in combination with IMGs for the modification of tumor cells. Expression vectors, including retroviral vectors, containing one or more IMG (and/or cell cycle regulators or inducers of apoptosis) are constructed as described herein. When more than one IMG (or genes encoding cell cycle regulators or inducers of apoptosis) is to be contained on the same construct, each IMG is preferably separated from the other(s) using an IRES as described herein. A particularly preferred IRES is the poliovirus IRES.

Once an effective combination of IMGs has been identified for a particular human tumor, those IMGs are delivered to a patient's tumor cells in vivo or in vitro followed by a return of the modified tumor cells (typically the modified cells will be irradiated prior to introduction) to the patient. As described more fully in the examples below, a variety of means may be employed for the delivery of IMGs to human tumor cells (e.g., biolistic transformation of tumor cells in situ, cationic liposomes, retroviral infection, etc.).

a. Combination Immunogene Therapy for Glioblastoma Using B7-2 and GM-CSF

As shown in the examples below, the human tumor/Hu-PBL-SCID/bg model of the present invention was employed to determine that tumor growth was markedly inhibited when these animals were vaccinated with glioblastoma cells transduced with genes encoding the T cell costimulatory molecule B7-2 and the proinflammatory cytokine GM-CSF.

Treatment of patients having glioblastoma multiforme tumors is conducted as follows. One to three grams of tumor are harvested when patients originally present and undergo surgery. The tissue is harvested and treated as described in Ex. 11. Tumor cells are grown until sufficient numbers are present to allow retroviral gene transfer and selection.

The primary tumor cells are transfected with pLSNBG9 (encodes both B7-2 and GM-CSF) and selected by growth in the presence of G418 as described below. Briefly, virus stock is thawed from −80° C. at 37° C. Polybrene is added to the thawed virus solution at a final concentration of 4 μg/ml. Culture medium is added to the virus solution to bring the final volume to 1.5 ml. Logarithmic growth phase tumor cells in T25 flasks are incubated in the virus supernatant at 37° C., 5% $CO_2$ for 3 hours. The same volume of medium containing polybrene but lacking virus is used as a control. After 3 hours, a further 3 ml of culture medium is added to each flask and the cells are incubated overnight. Medium is changed the next morning. Twenty-four hours after retroviral transduction, 200 μg/ml (final concentration) of the neomycin analog G418 is added to the culture medium. Medium is changed every 2 to 3 days until complete selection has taken place (i.e., all cells in the control flask are dead). After selection, cells are cultured in growth medium containing reduced concentrations of G418 (100 μg/ml) and are allowed to grow to confluence.

Transduced tumor cells are split into a new T25 culture flask at a density of 1×10⁶ cells. The amount of GM-CSF secreted into the culture medium is determined by ELISA (Quantikine, R&D Systems) 24 hr later. B7-2 expression is evaluated by flow cytometry using a monoclonal antibody specific for the human B70 antigen (i.e., B7-2). Aliquots of transduced cells to be used as vaccines are tested for the presence of bacteria, fungi, mycoplasma, HIV, Hepatitis B and Hepatitis C and replication-competent retrovirus (using the standard S+L− assay; Bassin et al. (1971) Nature 229:564).

Tumor cells that have been transduced with GM-CSF and B7-2 genes, selected and expanded are cyropreserved for future use. Briefly, cells are aliquoted in small volumes into cryopreservation tubes at 1×10⁶ cells/tube. Total volume is made up to 0.5 ml with a mixture of DMEM/F 12, FCS and DMSO to make a final concentration of 10% FCS and 20% DMSO. Cells are placed in an insulated styrofoam rack and placed at −80° C. for 24 hr, then placed in liquid nitrogen for long term storage. When cells are needed, they are thawed from liquid nitrogen at 37° C., washed twice in fresh medium and plated.

Transduced tumor cells are irradiated prior to their reinjection into patients to render the cells replication incompetent. Cells are irradiated with 20,000 Rad in a $^{60}$Cobalt machine.

Patients are given three subcutaneous injections in total. Each vaccination comprises 2×10⁶ irradiated autologous tumor cells modified to express B7-2 and GM-CSF. Injections are given on alternating lumbar flank regions which are marked immediately above the injection site with India ink to allow accurate localization later in the event that a local reaction is not apparent. Patients receive 0.1 ml of vaccine injected SC at each site using a 1 ml syringe fitted with a 23 gauge needle. All vaccinations are prepared by resuspension of cells in sterile Ringer's lactate solution. Patients having recurrent glioblastomas, the first injection is given on the first or second post-operative day. For patients with treatment resistant melanomas (discussed below), the timing of the first injection is not as critical as these patients are not undergoing any further surgical resection of their tumors. All patients receive a second and third vaccination 14 and 28 days, respectively after the first vaccination.

With the exception of the first vaccination in patients with recurrent glioblastomas (who are likely post-operative inpatients at the time), all subjects are treated as outpatients. Vital signs are monitored prior to immunization and every half hour for 3 hours after the SC injections. Patients are examined every hour for 3 hours for inflammation at the injection site and for evidence of rash, wheezing or edema. Provided there are no contraindications, subjects are discharged 3 hours after treatment. Should significant reactions occur, the patient is hospitalized for constant monitoring.

Patients are assessed in the clinic 3 days after vaccination and are evaluated weekly for 8 weeks and thereafter monthly for 4 months, every 3 months for 1 year and yearly thereafter. Blood samples are obtained for standard blood chemistries and histology at each visit. In addition, blood id drawn one week after each vaccination for replication-competent retrovirus assays.

Patients are observed for any toxicities. Patients' immunologic reaction to immunogene therapy is monitored locally and systemically. Local immune response is monitored by symptoms and signs of delayed type hypersensitivity (DTH) responses at the vaccination sites. In addition, punch biopsies are performed at injection sites 2 weeks after each vaccination (i.e., days 14, 28 and 42). These biopsies are compared to a biopsy taken from normal lumbar flank skin on day 1 (prior to initiation of therapy). Biopsies undergo standard pathologic examination for evidence of tumor cells and inflammation. In addition, immunohistochemical staining for CD45, CD4, CD8 and NK cell markers is performed.

Systemic immune responses are measured using two separate assays. Blood samples (20 ml each) are obtained on days 0, 7, 21, 35 and 49. These samples are used to isolate peripheral blood mononuclear cells (PBMC or PBLs) by centrifugation on a density (Hystopaque) gradient. The PBMC are then stimulated in vitro by co-incubation for 5 days with irradiated (20,000 Rad) autologous tumor cells. The stimulated PBMC are then used in the following two assays. First, a standard $^{51}$Chromium release cytotoxic T lymphocyte (CTL) assay is performed vs. autologous tumor cells. Second, an ELISPOT assay for interferon-γ production after exposure to autologous tumor cells is performed [Zhang et al. (1996) Proc. Natl. Acad. Sci. USA 93:14720]. The $^{51}$ Chromium release CTL assay is a standard assay for cell mediated immunity. This assay gives direct information concerning the ability of stimulated PBMC to kill tumor cells; however it has a relatively low sensitivity. To overcome this, the much more sensitive ELISPOT assay for interferon-γ production is also used. The ELISPOT assay determines the concentration of PBMC present that produce interferon-γ in response to exposure to autologous tumor cells. Since interferon-γ production is closely associated with $T_H1$ (cell mediated) immune responses, the number of PBMC producing interferon-γ in response to exposure to autologous tumor provides a measure of cell mediated immunity.

The clinical status of patients is followed by history, physical and laboratory parameters. In addition, appropriate diagnostic imaging tests (e.g., MRI scans with and without gadolinium enhancement) are obtained at 8 and 24 weeks, every 3 months for the following year, and yearly thereafter.

b. Combination Immunogene Therapy for Malignant Melanoma Using B7-2 and GM-CSF

Malignant melanoma is rapidly rising in North America. In contrast to other forms of skin cancers which are usually curable with surgery, malignant melanoma is often fatal due to its aggressive nature and tendency of early spread to distant organs. The treatment of primary melanoma is surgical while chemotherapy is indicated in patients with metastatic disease. Unfortunately, clinical response to chemotherapy is approximately 25% and 5 year survival is approximately 5%.

Treatment of patients having malignant melanoma is conducted using tumor cells modified to express B7-2 and GM-CSF as described above. Tumor cells are harvested from patients when patients originally present and undergo surgery and the cells are treated as described in Ex. 11.

Combinations of other IMGs (and/or genes encoding cell cycle regulators or inducers of apoptosis) shown to be effective at reducing tumorigenicity and or at inducing local or systemic immunity in the human tumor/Hu-PBL-SCID/bg model of the present invention are employed to treat human tumors, including glioblastoma and malignant melanoma.

In addition to the method of treatment described above wherein the patient's tumor cells are transduced with retroviruses encoding immune-modulators (e.g., B7-2 and GM-CSF) (and/or cell cycle regulators or inducers of apoptosis) and the tumor cells are selected in culture prior to reintroduction into the patient, the patient's tumor cells may be modified by introduction of DNA encoding the desired gene(s) (e.g., plasmid DNA transferred by biolistics or other physical means, recombinant adenoviruses, liposomes, direct injection of naked DNA). The cells are then allowed to express the transduced genes for a few days (or less), irradiated and used to immunize the patient. Subsequent boost immunizations may employ retrovirally transduced and selected tumor cells. The use of plasmid DNA (delivered by liposomes, biolistics, adenovirus vectors or as naked DNA) to modify tumor cells is preferred to the use of recombinant retroviruses in those cases where the patient's tumor cells take a lengthy period to grow in cell culture as retroviral transduction and selection takes a period of several weeks and for certain tumors (e.g., glioblastomas) it is desirable to vaccinate the patient with modified tumor cells within a few days (e.g., ~3) of the initial surgery. Vaccination within ~3 days of tumor debulking may permit the capture of the "alarm signal" required for costimulator activation on APC's and enhancement of activated macrophage and T cell traffic across the blood-brain barrier [Fuchs and Matzinger (1992) Science 258:1156 and Matzinger (1994) Annu. Rev. Immunol. 12:991].

Experimental

The following examples serve to illustrate certain preferred embodiments and aspects of the present invention and are not to be construed as limiting the scope thereof.

In the experimental disclosure which follows, the following abbreviations apply: M (molar); mM (millimolar); µM (micromolar); mol (moles); mmol (millimoles); µmol (micromoles); nmol (nanomoles); g (gravity); gm (grams); mg (milligrams); µg (micrograms); pg (picograms); L (liters); ml (milliliters); µl (microliters); cm (centimeters); mm (millimeters); µm (micrometers); nm (nanometers); hr (hour); min (minute); msec (millisecond); ° C. (degrees Centigrade); AMP (adenosine 5'-monophosphate); cDNA (copy or complimentary DNA); DTT (dithiotheritol); ddH$_2$O (double distilled water); dNTP (deoxyribonucleotide triphosphate); rNTP (ribonucleotide triphosphate); ddNTP (dideoxyribonucleotide triphosphate); bp (base pair); kb (kilo base pair); TLC (thin layer chromatography); tRNA (transfer RNA); nt (nucleotide); VRC (vanadyl ribonucleoside complex); RNase (ribonuclease); DNase (deoxyribonuclease); poly A (polyriboadenylic acid); PBS (phosphate buffered saline); OD (optical density); HEPES (N-[2-Hydroxyethyl]piperazine-N-[2-ethanesulfonic acid]); HBS (HEPES buffered saline); SDS (sodium dodecyl sulfate); Tris-HCl (tris[Hydroxymethyl]aminomethane-hydrochloride); rpm (revolutions per minute); ligation buffer (50 mM Tris-HCl, 10 mM MgCl$_2$, 10 mM dithiothreitol, 25 µg/ml bovine serum albumin, and 26 µM NAD+, and pH 7.8); EGTA (ethylene glycol-bis(β-aminoethyl ether) N, N, N', N'-tetraacetic acid); EDTA (ethylenediaminetetracetic acid); ELISA (enzyme linked immunosorbant assay); LB (Luria-Bertani broth: 10 g tryptone, 5 g yeast extract, and 10 g NaCl per liter, pH adjusted to 7.5 with 1N NaOH); superbroth (12 g tryptone, 24 g yeast extract, 5 g glycerol, 3.8 g KH$_2$PO$_4$ and 12.5 g, K$_2$HPO$_4$ per liter); DME or DMEM (Dulbecco's modified Eagle's medium); ABI (Applied Biosystems Inc., Foster City, Calif.); ATCC (American Type Culture Collection, Rockville, MY); Beckman (Beckman Instruments Inc., Fullerton Calif.); Becton Dickinson (Becton Dickinson, San Jose, Calif.); BM (Boehringer Mannheim Biochemicals, Indianapolis, Ind.); Bio-101 (Bio-101, Vista, Calif.); BioRad (BioRad, Richmond, Calif.); Brinkmann (Brinkmann Instruments Inc. Wesbury, N.Y.); BRL, Gibco BRL and Life Technologies (Bethesda Research Laboratories, Life Technologies Inc., Gaithersburg, Md.); Caltag (Caltag Laboratories Inc., South San Francisco, Calif.); CRI (Collaborative Research Inc. Bedford, Mass.); Eppendorf (Eppendorf, Eppendorf North America, Inc., Madison, Wis.); Falcon (Becton Dickenson Labware, Lincoln Park, N.J.); Invitrogen (Invitrogen, San Diego, Calif.); New Brunswick (New Brunswick Scientific Co. Inc., Edison, N.J.); NEB or New England Biolabs (New England BioLabs Inc., Beverly, Mass.); Novagen (Novagen, Inc., Madision, Wis.); Pharmigen (PharMingen, San Deigo, Calif.); Pharmacia (Phanmacia LKB Gaithersburg, Md.); Promega (Promega Corporation, Madison, Wis.); R & D Systems (R & D Systems Inc., Minneapolis, Minn.); Sigma (Sigma Chemical Co., St. Louis, Mo.); and Stratagene (Stratagene Cloning Systems, La Jolla, Calif.).

Unless otherwise indicated, all restriction enzymes were obtained from New England Biolabs and used according to the manufacturers directions. Unless otherwise indicated, synthetic oligonucleotides were synthesized using an ABI DNA synthesizer, Model No. 391.

EXAMPLE 1

Figure 1:
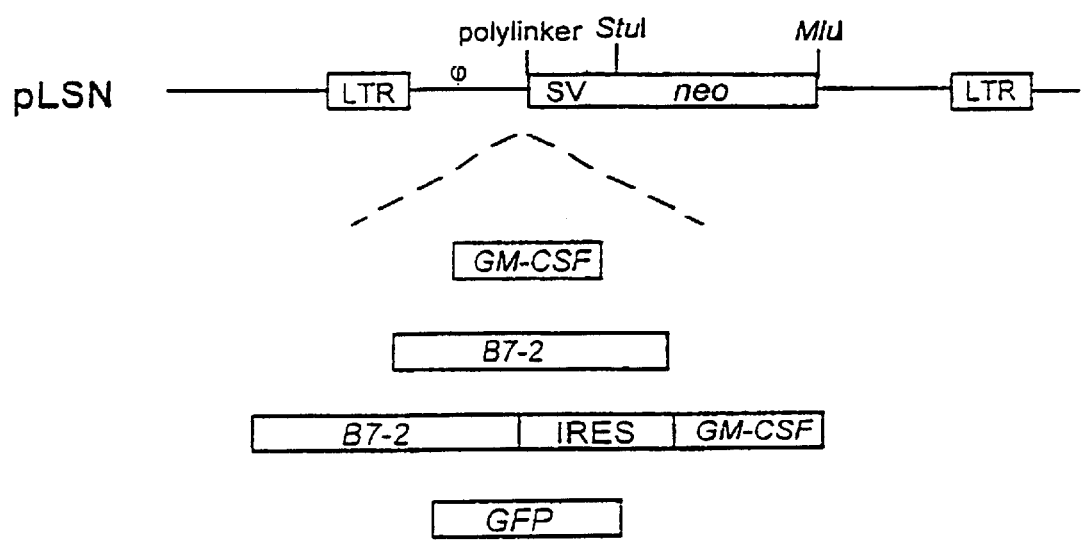
FIG. 1 provides a schematic showing the pLSN, pLSNB70, pLSNGM 1, pLSN-BG9 and pLSN-GFP retroviral constructs.

Construction Of Mono- And Bi-Cistronic Retroviral Vectors And Packaging Of Recombinant Virus Retroviral gene therapy vectors were constructed that contained the genes for GM-CSF, B7-2, GM-CSF and B7-2, or GFP gene as shown schematically in FIG. 1. FIG. 1 provides a schematic showing the map of the parental vector (pLSN), pLSNB70 (encodes human B7-2), pLSNGM1 (encodes human GM-CSF), pLSN-BG9 (encodes both B7-2 and GM-CSF) and pLSN-GFP (encodes GFP).

All genes were cloned into the polylinker region of the MLV-based pLSN plasmid [Robinson et al (1995) Gene Therapy 2:269 and co-pending Application Ser. No. 08/336, 132]. Therapeutic genes were inserted into pLSN such that their expression was under the control of the retroviral LTR (long terminal repeat) whereas a neomycin-resistance gene was under the control of an internal SV40 promotor. The vectors lacked the gag, pol, or env genes necessary for retroviral packaging in order to render them replication incompetent. These structural proteins were provided in trans by the retroviral packaging cell line PA317 [ATCC CRL 9078; Markowitz et al. (1988) J. Virol. 62:1120] or PG13 [ATCC CRL 10686; Miller et al. (1991) J. Virol. 65:2220]. For the bi-cistronic vector containing GM-CSF and B7-2 genes, the two genes were interposed with an internal ribosome entry site (IRES) derived from the Encephalomyocarditis Virus (EMCV) genome (pCITE-1, Novagen).

a) Construction of pLSN pLSN is a derivation of pLNL6, a retroviral vector approved for clinical use in the United States of America. To construct pLSN an intermediate vector, pLLL, was first constructed. pLLL was constructed using pLNL6 (SEQ ID NO: 1) as a starting point. pLNL6 contains the MoMuLV promoter in the 3' LTR and the murine sarcoma virus (MSV) promoter in the 5' LTR. For ease in subsequent cloning steps, the few cloning sites and the internal SV-neo gene present in pLNL6 were removed and replaced with a synthetic polylinker to generate pLLL.

To construct pLLL, pLNL6 was digested with ClaI and BclI and the vector fragment was gel purified using GeneClean (Bio-101) according to the manufacturer's instructions. A double-stranded insert containing the polylinker site was constructed using the following two oligonucleotides: 5'-GATCTAAGCTTGCGGCCG CAGATCTCGAGCCATGGATCCTAGGCCTGATCACG CGTCGACTCGCGAT-3' (SEQ ID NO:2) and 5'-CGATCGCGAGTCGACGCGTGATCAGGCCTAGG ATCCATGGCTCGAGATCTGCGGCCGCAAGCTTA-3' (SEQ ID NO:3). These oligonucleotides were annealed, kinased and ligated to the gel purified pLNL6 vector fragment and the ligation mixture was used to transform competent DH5a cells (BRL). Proper construction of pLLL was confirmed by restriction enzyme digestion of plasmid DNA prepared from ampicillin-resistance bacterial colonies as well as by DNA sequencing near the site of insertion of the polylinker.

To generate a vector containing a selectable marker which allows for the isolation of cells which have incorporated the vector DNA, pLSN was created. pLSN contains the neo gene under the transcriptional control of the SV40 enhancer/promoter. To create pLSN, a BamHI/StuI fragment containing SV40 enhancer/promoter was isolated from pLNSX [Miller, A. D. and Rosman, G. J. (1989) BioTechniques 7:980]. pLNSX and pLLL were digested with BamHI and StuI and the digestion products were gel purified. A small fragment of approximately 350 bp which contained the SV40 promoter from pLNSX was cloned into the pLLL vector. The final product, designated pLLL/SV40, was confirmed by restriction enzyme digestion using BamHI and ClaI.

In order to insert a better translation initiation codon at the beginning of the neo gene, the neo gene was isolated from pLNSX using PCR. Pfu polymerase (Stratagene) was used to amplify the gene. This amplification was conducted in 5 µl of 10× Pfu reaction buffer, 0.5 µl of dNTP (15 mM), 0.5 mM of each of the following primers: 5'-AAGCTTGATCACCACCATGATTGAACAAGATGG-3' (SEQ ID NO:4) and 5'-CCGGATCCGTCGACCCCAG AGTCCCGCTCAGAAG-3' (SEQ ID NO:5), 0.5 µl of pLNSX (0.01 µg) and 38 µl of ddH$_2$O. These primers contain the modified translation initiation control sequence (—CCACCATG—), as this modification was found to greatly increase the strength of the neo gene in tissue culture cells [Kozak, M. (1986) Cell 44:283].

The mixture was heated at 95° C. for 5 min and 1 µl of Pfu polymerase was added. This reaction mixture was cycled through 30 cycles at 94° C. for 1 min, 55° C. for 1 min, and 72° C. for 3 min. After amplification, the DNA comprising the neo gene was gel purified and ligated with the BclI-digested pLLL/SV40 vector to create pLSN. Confirmation of proper construction was made by restriction enzyme digestion as well as DNA sequencing.

b) Cloning of the Human B7-2 and GM-CSF cDNAs

GM-CSF and B7-2 cDNAs were amplified from normal human lymphocyte RNA by RT-PCR as follows. In each case, the oligonucleotides used for PCR amplification comprised an optimized eukaryotic initiation sequence. For amplification of the GM-CSF cDNA, the following primer pair was used: 5' primer: 5'-CCCGGG AAGCTT CCACCATGTGGCTGCAGAGCCTG-3' (SEQ ID NO:6) and 3' primer: 5'-AATGGATCCTATCACTCCTGG ACTGGCTC-3' (SEQ ID NO:7). The sequence of the human GM-CSF cDNA is available in GenBank accession no. M11220 and in SEQ ID NO:8. For amplification of the B7-2 cDNA, the following primer pair was used: 5' primer: 5'-TGTGGATCCACCATGGGACTGAGTAACATT-3' (SEQ ID NO:9) and 3' primer: 5'-TTTGGATCCTTA AAAACATGTATCACTTTTGTCGC-3' (SEQ ID NO:10). The sequence of the human B7-2 cDNA is available in GenBank accession no. U04343 and in SEQ ID NO:11. RT-PCR was carried out using an RT-PCR kit (BRL and Promega) according to the manufacturer's instructions.

The PCR amplified B7-2 gene was cloned directly (i.e., blunt-end ligation) into HincII digested pT7T318U (Pharmacia) to generate pT7T318U-B7-2. The PCR amplified GM-CSF gene was digested with HindIII and BamHI and cloned into HindII and BamHI digested pBluescript KS(-) (Stratagene) to generate pBS-GM-CSF. Proper amplification and cloning of the B7-2 and GM-CSF open reading frames was confirmed by partial DNA sequencing and by restriction enzyme digestion.

c) Construction of Retroviral Vectors Containing B7-2, GM-CSF and GFP Genes

The B7-2 and GM-CSF cDNAs were subcloned into the retroviral vector pLSN to generate pLSNB70 and pLSNGM1, respectively. To generate pLSNB70, pT7T318U-B7-2 was digested with BamHI and the B7-2 fragment was gel purified and cloned into BglII-digested pLSN. To generate pLSNGM1, pBS-GM-CSF was digested with HindIII and BamHI and the GM-CSF fragment was gel purified and cloned into HindIII- and BamHI-digested pLSN.

In addition, cDNA for the reporter gene green fluorescent protein (GFP) was also inserted into the retroviral vector pLSN to generate pLSN-GFP. The GFP gene was PCR amplified using Pfu polymerase (Stratagene) from pGFP (Clontech) using the following primer pair: 5' primer: 5'-AAAAGCTTGGATCCACCATGAGTAAA GGA-3' (SEQ ID NO:12) and 3' primer: 5'-AATCTAG ATTAC-TATTTGTATAGTT CATCC-3' (SEQ ID NO: 13). The PCR amplified GFP gene was cloned directly into EcoRV-digested pBluescript KS(-) to generate pBS-GFP#1. pBS-GFP#1 was digested with NotI and XhoI and the GFP fragment was gel purified and inserted into NotI- and XhoI-digested pLSN to generate pLSN-GFP.

Each of the resulting vectors contained a neomycin resistance gene driven by an internal SV40 promoter.

d) Construction of a Bi-Cistronic Retroviral Vector Encoding B7-2 and GM-CSF

A bi-cistronic retroviral vector, pLSN-BG9, containing the B7-2 and GM-C SF genes separated by an IRES was constructed as follows. The following three DNA fragments were gel purified: the EMCV IRES from XhoI- and HindIII-digested pGEM-IRES8 (described below); the GM-CSF gene from HindIII- and BamHI-digested PCR product (section b); and the B7-2 gene from NotI- and XhoI-digested pLSNB70. The three purified fragments were mixed together and ligated into NotI- and BamHI-digested pLSN to generate pLSN-BG9. pGEM-IRES8 was constructed by isolating the EMCV IRES fragment from EcoRI- and MscI-digested pCITE-1 (Novagen) and inserting this fragment into EcoRI- and SmaI-digested pGEM-7Zf+ (Promega).

e) Generation of Recombinant Retrovirus

Retroviral plasmid DNA was transfected into the packaging cell line PA317 [Miller, A. D. and Buttimore, C. (1986) Mol. Cell. Biol. 6:2895 and Miller, A. D. (1990) Hum. Gene Ther. 1:5] by lipofection as described (Robinson et al., supra). Briefly, PA317 cells were transfected with pLSNGM1, pLSNB70, pLSN-BG9, or pLSN-GFP using lipofectamine (Gibco/BRL). Lipofection was carried out according to the manufacturer's protocol.

PA317 cells were grown in DMEM containing 10% FBS and penicillin and streptomycin in an atmosphere containing 10% $CO_2$ at 37° C. Twenty hours prior to lipofection, PA317 cells were placed into a T25 flask (Falcon) at 50% confluency (approximately $1\times10^6$ cells/flask). To transfect the cells, DNA (4 μg) was added to 300 μl serum-free DMEM lacking antibiotics in a microcentrifuge tube (Eppendorf), and mixed gently. In a 15 ml polycarbonate tube (Falcon), 300 μl serum-free DMEM and 12 μl of lipofectamine were mixed gently. The two solutions were combined by adding the DNA-containing solution dropwise into the lipofectamine tube, and the mixture was incubated at RT for 45 min. Following this incubation, 2 ml of serum-free DMEM was added and mixed gently. The cells were washed with serum-free DMEM and the DNA/lipofectamine mixture was gently added to the cells. The cells were incubated at 37° C. in a 10% $CO_2$ incubator for 5 hr. After the 5 hr incubation, 2.5 ml of DMEM containing 20% FBS and antibiotics was added to the T25 flask and the cells were incubated overnight. Twenty hours after the 5 hr incubation, the medium was replaced with fresh DMEM containing 20% FBS and antibiotics. For vector titration, the medium was changed at 24 hr after the medium was replaced with fresh DMEM and virus was harvested 24 hr later. When cells were to be cloned (i.e., for the production of stable producer cell lines), the transfected PA317 cells were split at a 1:10 ratio into selective medium (i.e., DMEM containing 500 μg/ml G418 and 10% FBS).

Replication incompetent virus was harvested from supernatant of the transfected PA317 cultures 48 hrs after transfection of the PA317 cells and immediately frozen at −80° C. for later use.

EXAMPLE 2

Expression of B7-2 and GM-CSF in the Human Glioblastoma Cell Line D54MG

Viral particles containing recombinant retroviral genomes encoding either GM-CSF, B7-2, B7-2/GM-CSF or GFP were used to transduce the human glioblastoma cell line D54MG.

a) Growth Of D54MG in Tissue Culture

The human glioblastoma cell line D54MG [obtained from Dr. D. Bigner, Duke University, Durham, NC; Bigner et al. (1981) J. Neuropathol. Exp. Neurol. 40:201] was cultured in Dulbucco's Modified Eagle's Media (DMEM) with 10% fetal bovine serum (Gibco), 0.2 units/ml penicillin-streptomycin solution (Sigma), and 0.2 mM glutamate at 37° C. in a humidified atmosphere containing 5% $Co_2$.

b) Retroviral Transduction

Frozen virus stock was thawed at 37° C. Polybrene was added to the thawed virus solution at a final concentration of 4 μg/ml. Culture media was added to the virus solution to bring the final volume to 1.5 ml. D54MG cells in logarithmic growth phase in T25 flasks (approximately $1\times10^6$ cells) were incubated in the virus supernatant at 37° C., 5% $CO_2$ for 3 hours. The same volume of media and polybrene without virus was used as control. After 3 hours, a further 3 ml of culture media was added to each flask and they were incubated overnight. Media was changed the next morning.

c) Selection of Transduced Cells

Twenty-four hours after retroviral transduction, 500 μg/ml of the neomycin analog G418 was added to the culture media. Media was changed every two to three days until complete selection had taken place (i.e., all cells in the control flasks were dead). After selection, the cells were cultured in growth media containing reduced concentrations of G418 (250 μg/ml) and allowed to grow to confluence.

d) Analysis of B7-2 Expression by Flow Cytometry

Transduced D54MG cells at approximately 70% confluence were harvested by scraping after room temperature incubation for 15 minutes in 0.02% EDTA in Phosphate-Buffered Saline (PBS). In aliquots of 106 cells per 200 μl of immunofluorescence (IF) buffer (2% fetal calf serum, 0.02% sodium azide in PBS), samples were incubated on ice for 1 hour with 1 μg of RPE-conjugated monoclonal anti-human B7-2 antibody (Ancell) or 1 μg of RPE-conjugated isotype-control murine IgG, antibody (Pharmingen). Cells were washed four times in IF buffer, and fixed in 1% formalin in PBS. Samples were then read on a cytometer (B-D Flow Cytometer) using standard techniques.

e) Analysis of GM-CSF Expression by ELISA

Transduced D54MG cells at approximately 70% confluence in T75 flasks were incubated in fresh media for 24 hours. After this period of incubation, media was harvested and centrifuged briefly to remove cells and debris. The cell number per flask was determined. GM-CSF levels in the harvested media was tested using a commercially available kit (Quantikine, R & D Systems) as per the manufacturer's instructions. The level of GM-CSF was converted to pg/$10^6$ cells/24 hours based on the cell number in the flasks from which the media originated.

f) Expression of B7-2 and GM-CSF in D54MG Cells

Flow cytometry studies showed that B7-2 was expressed on the surface of B7-2- and B7-2/GM-CSF-transduced D54MG cells but not on wild type or GM-CSF-transduced cells (1-2 orders of magnitude fluorescence shift compared to isotype controls). Flow cytometry of GFP-transduced D54MG cells without staining revealed mildly increased autofluorescence compared to wild type D54MG. Representative flow cytometry histograms are shown in FIGS. 2A–E.

FIGS. 2A–E provide flow cytometry histograms for: wild type D54MG (2A), B7-2-transduced D54MG (2B), GM-CSF-transduced D54MG (2C), B7-2 and GM-CSF-transduced D54MG (2D), and GFP-transduced D54MG (2E). For FIGS. 2A–2D, the histograms on the left represent D54MG cells stained with isotype matched control antibodies while the histograms on the right represent staining with monoclonal anti-human B7-2 antibodies. For FIG. 2E, the histogram on the left represents unstained wild type D54MG cells while the histogram on the right represents unstained GFP-transduced D54MG.

GM-CSF production was significant for GM-CSF-transduced (30 ng/$10^6$ cells/day) and B7-2/GM-CSF-transduced (5 ng/$10^6$ cells/day) cells but not for wild type or B7-2-transduced cells. Gene expression in the transduced D54MG cells is summarized in Table 1.

TABLE 1

Therapeutic Gene Expression In Vitro In Wild Type And Transduced D54MG By ELISA (GM-CSF) Or Flow Cytometry (B7-2)

| Cell Line | Vector (Genes Transferred) | GM-CSF Production (ng/$10^6$Cells/Day) | B7-2 Expression (Orders Of Magnitude Fluorescence Shift) |
|---|---|---|---|
| D54MG | None | 0.0 | 0 |
| D54MG | pLSNB70 (B7-2) | 0.0 | 2 |
| D54MG | pLSNGM1 (GM-CSF) | 30.0 | 0 |
| D54MG | pLSNBG9 (B7-2 and GM-CSF) | 5.0 | 1 |

The above results demonstrate that therapeutic gene expression in the D54MG human glioblastoma cell line was high after in vitro transduction with the pLSN-based retroviral vectors. Levels of GM-CSF production were comparable to those reported in other retrovirally transduced tumor cell lines [Dranoff et al (1993) Proc. Natl. Acad. Sci. USA 90:3539 and Jaffee et al. (1993) Cancer Res. 53:2221]. Quantification of B7-2 expression is difficult using flow cytometry as expression is essentially a binary system (either present or absent on the cell surface). However, B7-2 molecules were clearly present on the surface of D54MG cells transduced with retroviral vectors containing the B7-2 gene and absent on wild type or GM-CSF-transduced cells. These results demonstrate that the above-described retroviral vectors provide simple, reliable tools for transferring GM-CSF and/or B7-2 genes into human glioblastoma cells in vitro.

EXAMPLE 3

Tumor Growth Efficiency and Human PBL Reconstitution in SCID/Beige and SCID/nod Mice This example describes the reconstitution of SCID/nod and SCID/beige mice with human PBL and the engraftment of human tumor cells in these mouse strains.

a) Animals and Human PBL Reconstitution

For most experiments, four to five week old female C.B-17-SCID-beige mice were purchased from Taconic (Germantown, N.Y.). For the first vaccination/challenge experiment, four to five week old female SCID/nod mice were obtained from Dr. L. Pilarski (Cross Cancer Institute, University of Alberta, Edmonton, Alberta). The mice were maintained in filtered cages in a virus free environment and received cotrimoxazole in their drinking water twice per week.

Hu-PBL-SCID mouse reconstitution was carried out as previously described [Zhang et al. (1996) Proc. Natl. Acad. Sci. USA 93:14720]. Briefly, each mouse was intraperitoneally (IP) injected with $2-3 \times 10^7$ PBLs resuspended in 0.5 ml of Hanks' balanced salt solution. A near 100% success rate in reconstitution of SCID/bg mice was obtained when fresh PBLs were used. Five days to three weeks after reconstitution, mice were bled from the tail and the human Ig level was assessed by enzyme-linked immunosorbent assay (ELISA) using a monoclonal rabbit anti-human IgG/IgM antibody (Jackson Labs) and control human IgG (Sigma).

Preliminary results indicated that SCID/nod mice were not as reliably reconstituted with human peripheral blood lymphocytes as were SCID/bg mice. Unlike SCID/bg mice, reconstitution of SCID/nod mice with human PBLs appeared to vary both from PBL donor to PBL donor and from mouse to mouse. Furthermore, many hu-PBL-SCID/nod mice developed a disease characterized by cachexia, alopecia, and facial edema 3 to 6 weeks after reconstitution. This was not seen in unreconstituted SCID/nod mice or in SCID/bg mice with or without reconstitution. The etiology was unclear, though the possibilities of Graft vs. Host Disease and diabetes melitis were considered. Because of these difficulties, reconstituted SCID/bg mice are preferred for tumor growth and vaccination/challenge experiments.

b) Subcutaneous Tumor Growth Experiments

Five to seven week old SCID/bg mice were injected subcutaneously (SC) on the right flank with $2 \times 10^6$ retrovirally-transduced and selected D54MG cells. Control mice were injected SC on the right flank with wild type D54MG cells. Six days post injection, mice were reconstituted via IP injection as described above with $2 \times 10^7$ human peripheral blood lymphocytes isolated on a Histopaque gradient (Sigma) from the buffy coat layer of whole blood from healthy donors. Reconstitution was monitored by examination of sera (tail bleeds) for the presence of human Ig by ELISA. In all but one experiment, half of the mice from each group (transduced and untransduced) were left unreconstituted as controls. Tumor size was measured in three directions by calipers every 3 to 5 days. Comparison was made between transduced and untransduced tumor cells and between reconstituted and unreconstituted mice.

c) Statistical Analysis

Comparison between tumor sizes in different groups was performed using standard one-way analysis of variance (ANOVA).

d) Tumor Growth and Human PBL Reconstitution in SCID/Beige and SCID/Nod Mice

As described below, SCID/bg mice receiving human PBL via IP injection supported the growth of a human melanoma cell line with nearly 100% success and these animals demonstrated significant levels of human lymphocytes by flow cytometric analysis in spleen and peripheral blood 38 days post reconstitution. This example shows that both SCID/nod and SCID/bg mice supported the growth of wild type D54MG cells (human glioblastoma) subcutaneously with 100% efficiency (35/35) regardless of human lymphocyte reconstitution. D54MG tumors transduced with B7-2, GM-CSF, or both B7-2 and GM-CSF also grew with 100% efficiency in unreconstituted SCID/bg mice (4/4, 8/8, and 4/4 respectively). Growth of D54MG tumors transduced with B7-2 and GM-CSF was inhibited in human lymphocyte-reconstituted mice as detailed below.

Reconstitution with human PBLs was monitored by ELISA for the presence of human Ig using sera collected from the tail of the reconstituted mice. All SCID/bg mice receiving human PBLs (46/46) had significant levels (>100 μg/ml) of human Ig in serum within 14 days of reconstitution. However, 3 of 12 SCID/nod mice that received human PBLs failed to demonstrate human Ig on serial testing and were excluded from the study. Subsequent studies with SCID/nod mice revealed that the success of human PBL reconstitution also varied significantly from PBL donor to PBL donor. For these reasons, SCID/bg mice (not SCID/nod) were preferred for tumor growth and vaccination/challenge experiments.

EXAMPLE 4

Growth Suppression of B7-2 and GM-CSF-Transduced

D54MG But Not Wild Type D54MG In Hu-PBL-SCID/bg Mice In two separate experiments, growth of D54MG transduced with B7-2 in human PBL reconstituted SCID/bg mice was markedly inhibited compared to untransduced and/or unreconstituted controls. These results are summarized in FIGS. 3A and 3B.

For the results shown in FIG. 3, all mice received $2 \times 10^6$ tumor cells (either D54MG or D54MG-B7-2) subcutaneously on the right flank on Day 0. Mice were injected IP with $2 \times 10^7$ human PBL six days after tumor cell injection. Reconstitution was confirmed by detection of serum human Ig levels >100 μg/ml. In the first experiment (3A), all mice were reconstituted with human PBLs. In FIG. 3A, tumor volume (mm³) is plotted over time (days) for mice receiving untransduced D54MG cells (open circles; "D54MG") and D54MG cells transduced with pLSNB70 (solid squares; "D54MG-B7-2"). In the second experiment (3B), half the mice from both groups (D54MG and D54MG-B7-2) were left unreconstituted (hatched lines). In FIG. 3B, tumor volume (mm³) is plotted over time (days) for mice receiving untransduced D54MG cells (solid squares) and D54MG cells transduced with pLSNB70 (open triangles). In FIG. 3, arrows are used to indicate the times at which the tumor cells and lymphocytes were injected.

A standard test for statistical significance in subcutaneous tumor growth models is comparison of tumor volumes by ANOVA at a point approximately two-thirds along the growth curve [Gallagher et al. (1993) Tumor Immunology: A Practical Approach, IRL Press, Oxford, UK]. By this criteria, the mean tumor volume for B7-2-transduced tumors in human lymphocyte-reconstituted mice was significantly less than the mean tumor volume for wild type (i.e., non-transduced) tumors by 22 days in the first experiment and by 35 days in the second experiment ($p<0.05$ in both). Interestingly, growth of D54MG-B7-2 tumors in unreconstituted mice was also mildly inhibited compared to wild type tumors (FIG. 3B). However, growth inhibition was much more marked in the reconstituted mice. These results suggests that, although a small portion of the growth inhibition seen for D54MG-B7-2 may be human lymphocyte-independent, the predominant effect is dependent on human lymphocytes.

Growth of GM-CSF-transduced D54MG in human lymphocyte reconstituted mice was moderately inhibited compared to untransduced and/or unreconstituted controls in two separate experiments. These results are summarized in FIGS. 4A and 4B.

For the results shown in FIG. 4, all mice received $2 \times 10^6$ tumor cells (either D54MG or D54MG-GM-CSF) subcutaneously on the right flank on Day 0. Mice were injected IP with $2 \times 10^7$ human PBL six days after tumor cell injection. Reconstitution was confirmed by detection of serum human Ig levels >100 μg/ml in ELISAs. In both experiments shown in FIGS. 4A and 4B, half the mice from both groups (D54MG and D54MG-GM-CSF) were left unreconstituted (hatched lines). In FIG. 4A, tumor volume (mm³) is plotted over time (days) for mice receiving untransduced D54MG cells (solid squares; "D54MG") and DM54MG cells transduced with pLSNGM1 (open triangles; "D54MG-GM-CSF"). In FIG. 4B, tumor volume (mm³) is plotted over time (days) for mice receiving untransduced D54MG cells (solid squares) and D54MG cells transduced with pLSNGM1 (open triangles). In FIG. 4, arrows are used to indicate the times at which the tumor cells and lymphocytes were injected.

Neither of the experiments shown in FIGS. 4A and 4B achieved statistical significance by ANOVA on their own. However, when the results from the two experiments were pooled, GM-CSF-transduced tumors in human PBL-reconstituted mice were significantly smaller than wild type by 55 days ($p<0.001$). No inhibition of D54MG-GM-CSF tumor growth was observed in unreconstituted mice.

These results demonstrate that transduction of D54MG tumor cells with recombinant retroviral vectors encoding either B7-2 or GM-CSF resulted in an inhibition of tumor growth in human PBL-reconstituted SCID/bg mice (FIGS. 3 and 4). This demonstrates that the expression of either the human B7-2 gene or the human GM-CSF gene in glioblastoma cells overcomes local immunosuppression and results in a significant antitumor response. As demonstrated in the example below, the expression of both human B7-2 and GM-CSF genes in glioblastoma cells induces a systemic immune response that inhibits tumor growth at distant sites.

EXAMPLE 5

Efficacy of Immunization of Hu-PBL-SCID/nod and Hu-PBL-SCID/bg Mice with Therapeutic Gene-modified D54MG Tumor Cells The ability to inhibit tumor growth in human PBL-reconstituted SCID mice by vaccination of the reconstituted mice prior to challenge with tumor cells was examined.

a) Vaccination/Challenge Experiments

In the first vaccination/challenge experiment, five to six week old female SCID/nod mice were reconstituted with $2 \times 10^7$ PBL from healthy donors via IP injection. Reconstitution was monitored by examination of sera (tail bleeds) for the presence of human Ig by ELISA. Five days after reconstitution, mice were vaccinated via IP injection of $1 \times 10^5$ irradiated (20,000 rad) D54MG cells (either wild type, GFP-transduced, or B7-2 and GM-CSF-transduced). Five days post-vaccination, all mice received SC injections of $1 \times 10^6$ unirradiated wild type D54MG cells on the right flank. Tumor growth was measured as described above.

The second vaccination experiment was performed similarly, but in this instance, SCID/bg mice (Taconic) were used. In addition, the order of injections was slightly different. These mice first received SC injections of $1 \times 10^6$ wild type D54MG cells on their right flanks. Ten days later, they were reconstituted with $2 \times 10^7$ human PBL. Ten days after reconstitution, the mice were vaccinated with $1 \times 10^5$ irradiated tumor cells (either wild type, GFP-transduced, or B7-2/GM-CSF-transduced).

b) Vaccination of Hu-PBL-SCID/Bg Mice with D54MG Cells Expressing Therapeutic Genes Induces a Systemic Immune Response SCID/nod and SCID/bg mice were reconstituted, vaccinated and challenged with wild type D54MG cells as described above. As shown in FIG. 5A, growth of wild type D54MG tumors in human PBL-reconstituted SCID/nod mice which had been vaccinated with irradiated B7-2/GM-CSF-transduced D54MG was markedly inhibited compared to mice vaccinated with wild type or GFP-transduced D54MG. In FIG. 5A, tumor volume (mm³) is plotted over time (days) for mice vaccinated with either D54 cells transduced with pLSN-BG9 (open squares; "D54MG-B7-2-GM-CSF"), D54MG cells transduced with pLSN-GFP (solid circles; D54MG-GFP") or untransduced D54MG cells (solid squares; "DM54MG"). In FIG. 5A, an arrow indicates the time at which the tumor cells were injected.

While the results shown in FIG. 5A demonstrate that the growth of wild type D54MG tumors was inhibited in Hu PBL-SCID/nod mice vaccinated with irradiated B7-2/GM-CSF-transduced D54MG cells. However, small sample sizes due to the exclusion of several unsuccessfully reconstituted mice (3/12) prevented this effect from reaching statistical significance. This problem was subsequently overcome by performing all remaining studies with reconstituted SCID/bg mice.

In a second vaccination experiment, wild type growth inhibition was seen in human PBL-reconstituted SCID/bg mice vaccinated with irradiated D54MG-B7-2/GM-CSF cells but not in mice vaccinated with either wild type D54MG or D54MG-GFP cells. In this second vaccination experiment all mice were successfully reconstituted with human PBLs as judged by ELISA (human Ig >100 μg/ml). The results are summarized in FIG. 5B. In FIG. 5B, tumor volume (mm³) is plotted over time (days) for mice vaccinated with either D54 cells transduced with pLSN-BG9 (open squares; "D54MG-B7-2-GM-CSF"), D54MG cells transduced with pLSN-GFP (solid circles; D54MG-GFP") or untransduced D54MG cells (solid squares; "DM54MG"). In FIG. 5B, arrows are used to indicate the times at which the tumor cells and lymphocytes were injected as well as the time at which the vaccination was given.

Unlike the first vaccination study (FIG. 5A), in the second vaccination study wild type D54MG cells were injected subcutaneously into the flank 20 days prior to vaccination. At the time of vaccination, tumors were palpable (1–2 mm$^3$) on all mice. After vaccination, tumor growth continued exponentially in mice vaccinated with wild type or GFP-transduced D54MG. However, in mice vaccinated with GM-CSF/B7-2 transduced D54MG, tumor size increased slightly after vaccination (peaking at a mean of 8 mm$^3$) and then regressed. Differences between the experimental and control groups achieved statistical significance by ANOVA ($p<0.001$) by day 42.

The above results demonstrate the inhibition of wild type tumor challenge growth in mice vaccinated with irradiated tumor cells transduced with retroviral vectors containing the B7-2 and GM-CSF genes and demonstrates that expression of these genes by glioblastoma cells induces a systemic immune response that inhibits tumor growth at distant sites.

It should also be noted that the present model, while an allogeneic system, has more similarities to autologous systems than may be immediately apparent. Unlike the classical immune-mediated rejection seen in allogeneic organ transplantation, this system is free of graft-origin "passenger lymphocytes." These lymphocytes are important in initiating allogeneic organ rejection responses by presenting antigen to host lymphocytes in the context of allogeneic Class II major histocompatibility complex (MHC) [Larsen et al. (1990) Annals of Surgery 212:308; Chandler and Passaro (1993) Archives of Surgery 128:279; Moller (1995) Transplantation Proc. 27:24]. The D54MG cell line expresses only Class I MHC and not Class II MHC in vitro. Although allogeneic Class I MHC molecules are expressed by the D54MG cells in this model, the absence of graft-origin Class II MHC-positive cells in the tumor renders this model more like an autologous system.

The use of the hu-PBL-SCID mouse model and a human glioblastoma tumor cell line has demonstrated the therapeutic utility and feasibility of in vivo immunogene therapy using GM-CSF or B7-2 genes (alone or in combination). The hu-PBL-SCID model provides a simple and powerful method to analyze human lymphocyte responses to human tumors in vivo. Early cancer immunotherapy studies using hu-PBL-SCID mice were limited by the influence of residual murine NK lymphocyte activity [Reddy et al. (1987) Cancer Res. 47:2456; Hill et al. (991) FASEB J. 5:A965; Mueller et al. (1991) Cancer Res. 51:2193; Zhai et al. (1992) Cancer Immunol. Immunother. 35:237]. This problem has been overcome by the use of the SCID/bg and the SCID/nod mouse strains that are deficient in NK cells [Croy and Chapeau (1990) J. Reprod. Fert. 88:231; MacDougal et al. (1990) Cell. Immunol. 130:106; Prochazka et al. (1992) Proc. Natl. Acad. Sci. USA 89:3290; Mosier et al. (1993) J. Exp. Med. 177:191; Malkovska et al. (1994) Clin. Exp. Immunol. 96:158].

In conclusion, the retroviral gene therapy vectors provided herein demonstrated efficient bi-cistronic gene transfer (B7-2 and GM-CSF) to human glioblastoma cells in vitro. In an in vivo allogeneic human tumor/lymphocyte system, glioblastoma cells that express these genes result in lymphocyte-mediated responses that inhibit tumor growth locally and at distant sites. These results demonstrate the feasibility of immunogene therapy for glioblastoma multiforme using B7-2 and GM-CSF genes.

EXAMPLE 6

Transduction and Expression of the B7-2 Gene in Established Tumor Cell Lines

To determine whether most of the human tumor cells are susceptible to retroviral transduction, and whether the T-cell costimulator gene B7-2 can be expressed in different tumors, a series of different types of human tumors were transduced with the B7-2 vector. Conditions for transduction were as described in Ex. 2. Twenty-four hrs after transduction, the cells were cultured in media containing different concentrations of G418. Results of this study are shown in Table 2.

TABLE 2

Transduction Of Tumor Cell Lines With pLSNB70

| Cell Type | Medium | Transduction Rate* /μg/ml (G418) |
|---|---|---|
| HeLa cervical epithelial carcinoma | DMEM | +++/500–1000 |
| SW480 colon adenocarcinoma | DMEM or L15 | +++++/750–1000 |
| HT-29 colon adenocarcinoma | McCoy's | +++++/500 |
| U87 MG/Glioblastoma-Astrocytoma | MEM + NaPy + NEa.a. or DMEM | +++++/1000 |
| SK-N-MC neuroblastoma | MEM ++ NaPy + NEa.a | +++/600 |
| SK-N-SH / neuroblastoma | <MEM + NaPy + NEa.a. | ++ |
| A-431 epidermoid carcinoma | DMEM | ++/250 |
| RD embryonal rhabdomyosarcoma | MEM | +++/250 |
| HepG2 hepatoma | DMEM | +++++/750–1000 |
| Huh7 hepatoma | DMEM | ++/500–750 |
| PC3 prostate tumor | F12/DMEM | –/250 no survivors |
| DU145 prostate tumor | MEM | ++++/600 |
| A375 melanoma | DMEM | ++++/1000 |
| SK-Mel-1 melanoma | MEM (suspension cells) | /300 |

*1+: <10 scc; 2+: >30 scc; 3+: >50 scc; 4+: >80 scc; 5+: >100 scc; and scc: single cell clone. MEM (Minimal Esstential Medium); NaPy (sodium pyruvate); NE a.a. (non-essential amino acids).

The results shown in Table 2 demonstrate that most of the established human tumor cells were efficiently transduced by the pLSNB70 virus. Some of the tumor cells are more resistant to G418 than others. The transduction rate was determined by counting the number of G418-resistant cell colonies. Expression of the B7-2 gene was demonstrated by immunohistochemical staining using an anti-B7-2 monoclonal antibody. Except for the few cell lines that were sensitive to low levels of G418 (e.g., PC3), most of the tumor cell lines tested were efficiently transduced with the B7-2 gene, and selected by G418 within two weeks.

EXAMPLE 7

Transduction and Expression of B7-2 in Primary Tumor Cells

Retroviral transduction of established cell lines is generally more efficient than transduction of primary tumor cells. For in vivo or ex vivo gene transduction, however, the target cells are fresh (i.e., primary) tissues or tumors. It is thus important to demonstrate B7-2 transduction in freshly isolated primary tumor cells. To this end, several tumor specimens from surgery or biopsy were propagated in culture for less than 5 passages and transduced with the pLSNB70 virus as described in Ex. 2. After transduction, the cultures were selected with G418. The results are summarized in Table 3.

TABLE 3

Retroviral Transduction Of Primary Tumor Cultures

| Cell type | Medium | Transduction/ Rate*/µg/ml |
|---|---|---|
| E81 (p11) | F12/DME | ++/250 |
| E82 (p3) | F12/DME | ++++/250 |
| E81 (p11) | F12/DME | +/250 |
| Hepatoma (PC) | RPMI; F12/DME | −/500 |
| Melanoma (DD) | RPMI | ++/250 |
| Melanoma (DJ) | RPMI | ++/250 |
| Adenocarcinoma (BP) | RPMI | +++/250 |
| Adenocarcinoma (LJ) | RPMI | +++/250 |

*(1+: <10 scc; 2+: >30 scc; 3+: >50 scc; 4+: >80 scc; 5+: >100 scc; scc, single cell clone).

As shown in Table 3, primary tumor cultures were found to be sensitive to low concentrations of G418 (approximately 250 µg/ml G418). Nevertheless, most of the transduced cells were selected within 10 days. The results shown in Table 3 illustrate the successful transduction of three primary gliomas, two melanomas and two adenocarcinomas with pLSNB70. B7-2 expression was also confirmed by immunohistochemical staining using a mouse anti-B7-2 antibody as the primary antibody and a FITC-labeled goat anti-mouse antibody as the secondary antibody. The majority of the selected cells (i.e, the transduced tumor cells that survived growth in the presence of G418) showed positive surface staining for B7-2.

EXAMPLE 8

Retroviral Transduction of GM-CSF in Established and Primary Tumor Cells

In animal studies, a high level of GM-CSF expression has been shown to be related to its therapeutic efficacy [Jaffee et al. (1993) Cancer Res. 53:2221 and Dranoff et al. (1993) Proc. Natl. Acad. Sci. USA 90:3539]. Two different retroviral vectors were constructed that contained the human GM-CSF cDNA to examine the level of GM-CSF expressed in transduced tumor cells. The first vector pLSN, which contains the wild type MoMLV LTR, was described above in Ex. 1 as was the construction of pLSNGM1. The second vector, pLGCTSN (ATCC 97803; Robinson et al., supra), contains a modified LTR in which the MoMLV U3 region is replaced by the CMV-IE enhancer/promoter and the HIV TATA and TAR elements which leads to an increased level of expression in human cells; in addition, pLGCTSN contains an extended packaging signal and a 3' splice acceptor sequence from MoMLV. The human GM-CSF cDNA was inserted into pLGCTSN to create pLGCTSN-GM1 as follows. The GM-CSF gene was released from pBS-GM-CSF (Ex. 1) by digestion with HindIII and BamHI and this fragment was inserted into HindIII- and BamHI-digested pLGCTSN to generate pLGCTSN-GM1.

A human melanoma cell line (SK-MEL-1; ATCC HTB 67) and the primary adenocarcinoma (LJ) culture ["AD 1 (LJ)"] were transduced with retroviruses derived from either pLSNGM1, pLGCTSN-GM, pLSNBG9 or pLSNB70, and selected with G418. The expression of GM-CSF was determined by ELISA using culture supernatants collected from the G418-selected cultures. Table 4 summarizes the amount of GM-CSF (ng/$10^6$ cells/24 hr) present in the culture supernatants.

TABLE 4

ELISA Of GM-CSF Expression In Established And Fresh Tumor Cell Cultures

| Vector | SK-MEL-1 | AD1(LJ) |
|---|---|---|
| Control (pLSNB70) | 0.1 | 0.03 |
| pLSNGM1 | 9 | 4 |
| pLGCTSN-GM | 9 | 8 |
| pLSNBG9 | 9 | 0.65 |

The virus derived from pLSNB70 (encodes B7-2) was used as a negative control for the expression of GM-CSF in the transduced cells; pLSNB70-transduced melanoma cells expressed GM-CSF at <0.1 ng/ml/$10^6$ cells in 24 h which was close to the background level of the ELISA. The pLSNGM1- and the pLGCTSN-GM-transduced cells expressed 9 ng/ml/$10^6$ cells of GM-CSF in 24 hr. This study used an established human melanoma cell line (SK-MEL-1) and the level of GM-CSF expression was determined 3 months after cells were selected by G418.

A similar study was performed using a primary human adenocarcinoma culture AD1 (LJ). The primary culture was prepared as follows. The tumor tissue was surgically removed, placed in HBSS on ice immediately after surgery and transferred to a biosafety hood. Ten milliliters of HBSS was placed in a sterile petri dish and the tumor tissue was added. Using forceps and a scalpel, normal tissue surrounding the tumor was removed and the tumor was transferred to a second petri dish containing 5–10 ml HBSS and the tumor was minced. Ten ml of a suspension containing the minced tumor was transferred to a 15 ml tube and the cells were collected by centrifugation at 100× g for 8 min. at room temp. The cells were resuspended in 2 ml of DMEM containing 20% FCS. The resuspended cells (2–3 ml) were transferred to a 50 ml tube and the following enzymes were added: 1 mg/ml collagenase type V, 10 µg/ml hyaluronidase type V, 300 U/ml DNase type IV and 10 µg/ml gentamycin sulfate. The cells suspension was then incubated at 37° C. with shaking for 60 min. The cells were then plated in tissue culture flasks containing DMEM containing 10% FCS, 10 µg/ml gentamycin sulfate, penicillin/streptomycin/glutamine solution (Gibco/BRL) and 1.25 µg/ml amphotericin (growth medium) and grown overnight in an incubator containing 5% $CO_2$ at 37° C. On the second day, non-adherent cells were removed by washing the flasks with 3 ml growth medium. The medium was changed every 3–7 days depending upon the growth rate of the cells. The cells were transduced with the pLSNB70 virus and grown in the presence of G418 as described above.

As shown in Table 4, the transduced and selected primary human tumor cells [AD 1(LJ)] produced GM-CSF in the range of 1–8 ng/ml/$10^6$ cells/24 hr (GM-CSF expression was determined 2–3 weeks after the cells were selected using G418). Thus, the unmodified retroviral vector pLSN is capable of producing high levels of GM-CSF in primary human tumor cells. The level of GM-CSF expression may be cell-type dependent, and further modification of the vector (e.g., use of cell-type- or tissue-specific enhancers and/or promoters) may further increase the level of expression in specific tumor cells.

EXAMPLE 9

Bi-cistronic Expression of B7-2 and GM-CSF in Established and Primary Tumor Cells To express both the B7-2 and GM-CSF therapeutic genes simultaneously in tumor cells, the bi-cistronic retroviral vector pLSNBG9 (Ex. 1) was employed. The plasmid DNA was transfected into PA317 cells and virus was harvested and used for transduction as described in Ex. 1. Both the established melanoma cell line SK-MEL-1 and the primary adenocarcinoma cell culture AD 1 (LJ) were transduced and selected by G418. After selection (typically 2 weeks after applying G418), the expression of GM-CSF and B7-2 in these two cell types was determined by ELISA (Table 4) and flow cytometry, respectively. Table 4 shows that the level of GM-CSF expression for the bi-cistronic vector was similar to the mono-cistronic vector pLSN-GM in SK-MEL-1 cells but was ten times less than the mono-cistronic vector in the primary AD1 (LJ) culture. The FACS analysis indicated that the mono-cistronic (pLSNB70) and bi-cistronic (pLSNBG9) vectors expressed B7-2 in both cell types. These results demonstrate that both B7-2 and GM-CSF can be expressed simultaneously following transduction of established and primary tumor cultures with virus derived from the bi-cistronic pLSNBG9 vector.

EXAMPLE 10

Construction of Expression Vectors for the High Level Expression of Therapeutic Genes The promoter strength of the retroviral vector determines the expression level of the transduced gene in eukaryotic cells. To increase the level of gene expression, we have modified the MLV vector and generated a series of vectors with enhanced promoter strength (Robinson et al., supra). To further improve the promoter strength, the strength of several promoters was examined in the human tumor cell line, HeLa (ATCC CCL 2), using a reporter CAT assay. Plasmids in which the CAT gene was placed under the transcriptional control of either the CMV-IE promoter/enhancer, the EF1α promoter/enhancer with or without intron 1, the MCT promoter (the modified MoMLV LTR present in pLGCTSN), and the HIV LTR (a number of these CAT constructs are described in Robinson et al, supra). The plasmids were transfected into HeLa cells and 48 hr later cell lysates were prepared and assayed for CAT activity as described (Robinson et al., supra). Constructs containing plasmids comprising the HIV-1 TAR element (i.e., the HIV LTR and the pMCT promoters) were also co-transfected along with a tat expression construct. The results are summarized in Table 5. In Table 5, the promoter activity is expressed relative to the activity of the CMV-IE promoter. In Table 5, the following abbreviations are used: EF1α+intron (the 1.442 kb EF1α enhancer/promoter element comprising intron 1); EF1α-intron (a 475 bp fragment containing the EF1α enhancer/promoter corresponding to map units 125 to 600 of the human EF1α gene) HIV+Tat (the pHIV-1/LTR-cat construct co-transfected with the tat expression construct); MCT pMCT-cat); and MCT+Tat (pMCT-cat co-transfected with the tat expression construct).

TABLE 5

| Promoter | Relative Activity |
|---|---|
| CMV-IE | 1.0 |
| EF1α + Intron | 2.16 |
| EF1α + Intron | 0.02 |
| HIV + Tat | 0.13 |
| MCT | 0.32 |
| MCT + Tat | 1.2 |

The results shown in Table 5 indicate that the human EF1α promoter plus its intron has the strongest activity compared with all other promoters tested. Thus, the EF1α promoter may be used to drive the expression of therapeutic genes in tumor cells. Retroviral and plasmid constructs in which the EF1α+intron promoter/enhancer is used to drive the expression of therapeutic genes is described below.

a) Construction of a Plasmid Expression Vector Containing The EF1α Enhancer/Promoter The human EF1α enhancer/promoter is abundantly transcribed in a very broad range of cell types including L929, HeLa, CHU-2 and COS cells [Uetsuki, T. et al., J. Biol. Chem., 264:5791 (1989) and Mizushima, S. and Nagata, S., Nuc. Acids. Res., 18:5322 (1990)]. A 1.442 kb fragment containing the human EF1α enhancer/promoter and a splice donor and acceptor from the human EF1α gene was isolated from human genomic DNA as follows. The 1.442 kb fragment corresponds to map units 125 to 1567 in the human elongation factor 1a gene (SEQ ID NO:14).

Genomic DNA was isolated from the MOU cell line (GM 08605, NIGMS Human Genetic Mutant Cell Repository, Camden, N.J.) using standard techniques [Sambrook, J. et al., Molecular Cloning: A Laboratory Manual, 2nd. ed., Cold Spring Harbor Laboratory Press, (1989) pp. 9.16–9.23]. Two synthetic oligonucleotide primers were used to prime the polymerase chain reaction (PCR) for the isolation of the 1.442 kb fragment containing the human EF1α enhancer/promoter. U.S. Pat. Nos. 4,683,195, 4,683,202 and 4,965,188 cover PCR methodology and are incorporated by reference.

The 5' primer, designated HEF1αL5, contains the following sequence: 5'-AAGCTTTGGAGCTAAGCCAGCAAT-3' (SEQ ID NO:15). The HEF1αL5 primer generates a HindII site at the 5' end of the 1.442 kb fragment. The 3' primer, designated HEF1αL3B, contains the following sequence: 5'-TCTAGAGTTTTCACGA CACCTGA-3' (SEQ ID NO: 16). The HEF1L3B primer generates a Xba I site at the 3' end of the 1.442 kb fragment. PCR conditions were as reported in Saiki, R. K. et al., Science 239:487 (1988). Briefly, 10 µg MOU genomic DNA and 1 µM final concentration of each primer were used in a 400 µl PCR reaction. Reaction conditions were 94° C. for 1 minute, 60° C. for 1 minute, 72° C. for 1.5 minutes, 30 cycles. Taq DNA polymerase was obtained from Perkin-Elmer Cetus; the reaction buffer used was that recommended by the manufacturer. The PCR reaction products were electrophoresed on a low melting agarose the 1.442 kb fragment was gel purified and digested with HindII and XbaI. The HindII/MaI fragment was then inserted into pSSD5 (described below) to generate pHEF1αBSD5. pSSD5 was constructed by digestion of the plasmid pLI [Okayama, H. and Berg, P., Mol. Cell. Biol., 3:280 (1983)] with PstI and EcoRI. Synthetic oligonucleotides (Operon) were ligated onto the PstI and EcoRI ends of pLI to generate the polylinker of pSSD5 (the SD5 polylinker). The sequences of the oligonucleotide pair used to create the polylinker are: SD5A5'-TCTAGAGCGGCCGCGGAGGCCGAATTCG-3' (SEQ ID NO:17) and SD5B5'-GATCCGAATTCGGCC TCCGCGGCCGCTCTAGATGCA-3' (SEQ ID NO:18). The ligation of this oligonucleotide pair into pLI destroyed the PstI site. Following the addition of the polylinker, the plasmid was digested with HindIII and partially digested with BamHI. The 572 bp HindIII/BamHI fragment containing the SV40 enhancer/promoter, the 16S splice junction and the SD5 polylinker was isolated by electrophoresis of the digestion products on a low melting temperature agarose gel (SeaPlaque, FMC BioProducts, Rockland, Me.). The 572 bp fragment was cut out of the gel and the agarose was removed by digestion with β-Agarase I (New England Biolabs)

followed by isopropanol precipitation according to the manufacturer's directions.

The 572 bp fragment was inserted into the plasmid pcDV1 [Okayama and Berg, supra] as follows: pcDV1 was digested with HindIII and BamHI and the 2.57 kb fragment containing the SV40 poly A sequences and the pBR322 backbone was ligated to the 572 bp fragment containing the SV40 enhancer/promoter, 16S splice junction and polylinker. The resulting plasmid was named pSSD.

The 671 bp BamHI/PstI fragment containing the SV40 poly A sequences (SV40 map units 2533 to 3204) was removed from SV40 DNA and cloned into pUC19 digested with BamHI and PstI. The resulting plasmid was then digested with BclI (corresponds to SV40 map unit 2770). The ends were treated with the Klenow enzyme and dNTPs to create blunt ends. Unphosphorylated PvuII linkers (New England Biolabs) were ligated to the blunted ends and the plasmid was circularized to create pUCSSD. The SV40 poly A sequences can be removed from pUCSSD as a BamHI/PvuII fragment.

pSSD5 was constructed by ligating together the following three fragments: 1) the 1873 bp SspI/PvuII fragment from pUC19; this provides the plasmid backbone; 2) the 796 bp fragment containing the SV40 enhancer/promoter and 16S splice junction and the polylinker from pSSD; this fragment was obtained by digestion of pSSD with SspI and partial digestion with BamHI followed by isolation on low melting agarose and recovery as described above; and 3) the 245 bp BamHI/PvuII fragment from pUCSSD (this fragment contains the SV40 poly A sequences). The three fragments were mixed together and ligated using T4 DNA ligase to create pSSD5. The polylinker of pSSD5 contains the following restriction sites: XbaI, NotI, SfiI, SacII and EcoRI.

b) Construction of pHEF-B70

A plasmid, pHEF-B70, in which the EF1α enhancer/promoter is used to drive the expression of the human B7-2 gene was constructed as follows. The B7-2 gene was removed from pLCTSNB70 (described below) by digestion with BamHI and the isolated B7-2 fragment was ligated into BamHI-digested pHEF1αBSD5 to generate pHEF-B70. pLCTSNB70 was constructed by ligating the B7-2 gene released from pT7T318U-B7-2 (Ex. 1) by BamHI digestion into BamHI-digested pLCTSN (ATCC No. 97802; Robinson et al., supra).

c) Construction of pHEF-IL-12

In the plasmid pHEF-IL-12, the IL-12A and IL-12B genes are under the transcriptional control of the EF1α enhancer/promoter.

i) Cloning of the Human IL-12 cDNA

RNA was isolated from activated NC37 B cells (ATCC CCL 214) and the IL-12A and IL-12B cDNAs were isolated by RT-PCR as described in Ex. 1. The following primers were employed for the amplification of the IL-12A cDNA: 5'-GAA GATCTGCGGCCGCCACCATGTGGCCCCC TGGGTCAGC-3' (SEQ ID NO:19; optimized initiation sequence underlined) and 5'-CCTCTCGAGTTAGGAAGC ATTCAGATAGC-3' (SEQ ID NO:20). The PCR product was cloned directly into EcoRV-digested pBluescript KS(-) to generate pKS-IL-12A. The IL-12A coding region is provided in SEQ ID NO:21.

The following primers were employed for the amplification of the IL-12B cDNA: 5'-AAAGAGCTCCACCATG TGTCACCAGCAGTTGGTC-3' (SEQ ID NO:22; optimized initiation sequence underlined) and 5'-AAGGATCCTAACTGCAGG GCACAGATGC-3' (SEQ ID NO:23). The PCR product was cloned directly into EcoRV-digested pBluescript KS(-) to generate pKS-IL-12B; the IL-12B coding region is provided in SEQ ID NO:24. Proper construction of both IL-12 constructs was verified by restriction enzyme digestion.

ii) Construction of pLSN-IL-12 pLSN-12 is a retroviral vector containing a IL-12A-IRES-IL-12B bi-cistron. To construct pLSN-IL-12, the following four fragments were gel purified: the IL-12A gene released from pKS-IL-12A by digestion with ClaI and PspAI; the IL-12B gene released from pKS-IL-12B by digestion with NotI and XhoI; the EMCV IRES was released from pGEM-IRES8 by digestion with XhoI and ClaI; and a pLSN vector backbone containing a PspAI site generated by removing the HIV vpr gene from pLSNvpr (described below) by digestion with MluI and PspAI. These four fragments were combined and ligated with NotI- and MluI-digested pLSNvpr to generate pLSN-IL-12.

pLSNvpr was constructed by digestion of pBS-vpr with NotI and XhoI and the vpr gene fragment was ligated with NotI- and XhoI-digested pLSN. The vpr gene was PCR amplified from pNL4-3 [Adachi et al. (1986) J. Virol. 59:284] and inserted into pBluescript KS(-) to generate pBS-vpr.

iii) Construction of pHEF-IL-12

To construct pHEF-IL-12, the following three fragments were isolated: the IL-12A gene was released from pKS-12A by digestion with ClaI and PspAI; the IL-12B gene released from pKS-IL-12B by digestion with NotI and XhoI; the EMCV IRES was released from pGEM-IRES8 by digestion with XhoI and ClaI. These fragments were cloned into NotI- and PspAI-digested pHEFvpr. pHEFvpr was constructed by ligation of a 360 bp BamHI fragment isolated from pLSNvpr with pHEF1αBSD5 that had been digested with BamHI and treated with alkaline phosphatase. d) Construction Of pHEF-IL-12-GM-CSF pHEF-IL-12-GM-CSF contains a IL-12A-EMCV IRES-IL-12B- poliovirus IRES-GM-CSF tri-cistron under the transcriptional control of the EF1α enhancer/promoter. To construct pHEF-IL-12-GM-CSF, the following four fragments were gel purified: a 2373 bp NdeI-PspAI fragment containing the IL-12B-EMCV IRES-IL-12A cistron isolated from pHEF-IL12; a 1320 bp NdeI-SphI fragment containing the EFla intron isolated from pHEF-IL-12; a 735 bp PspAI-XhoI fragment containing the poliovirus IRES from pKS-P2 (an equivalent DNA fragment is generated by PCR amplification of the IRES located within the first ~730 bp of the poliovirus genome [LaMonica et al. (1986) J. Virol. 57:515] using primers that will generate PspAI and XhoI sites).

e) Construction of pHEF-GM-CSF pHEF-GM-CSF was derived from pHEF-IL-12-GM-CSF by complete digestion with SmaI and partial digestion with HincII. The resulting approximately 4409 bp fragment was gel purified and self-ligated to produce pHEF-GM-CSF.

f) Construction of pHEF-BG

A plasmid, pHEF-BG, in which the 1.442 kb EF1α enhancer/promoter is used to drive the expression of both the human B7-2 and GM-CSF cDNAs (a bi-cistronic construct) is constructed as follows. The B7-2-IRES-GM-CSF bi-cistronic fragment was removed from pLSN-BG9 (Ex. 1) by digestion with NotI and BamHI and the gel purified fragment was inserted into NotI- and BamHI-digested pHEF1αBSD5 to generate pHEF-BG.

g) Construction of the pLSN-IL-12-GM-CSF Retroviral Vector pLSN-IL-12-GM-CSF provides a retroviral vector in which the MoMLV LTR is used to drive the expression of both the human IL-12 gene and GM-CSF cDNAs. pLSN-IL-12-GM-CSF was constructed by ligation of the following four fragments into BamHI-digested pLSN-GFP: the 1489 bp MoMLV vector fragment derived from SacII-XbaI-digested pLSN-GFP; the 1680 bp L-12B-IRES containing fragment from XhaI-NotI-digested pHEF-IL-12; the 760 bp IL-12A containing fragment from NotI-PspAI digested pHEF-IL-12; and the 1252 bp GM-CSF containing fragment from PspAI-BamHI digested pHEF-IL-12-GM-CSF.

h) Construction of the pLCTSN-pA-BG-EF Retroviral Vector pLCTSN-pA-BG-EF contains a cistron comprising the EF1α enhancer/promoter, B7-2 and GM-CSF cDNAs and SV40 polyadenylation signal inserted in an inverted orientation (relative to transcription from the 5' LTR). This vector was constructed by ligation of the following three fragments with HindIII and SalI digested pLCTSN vector: EF1α enhancer/promoter from SalI-NotI digested pHEF, B7-2/IRES/GM-CSF cistron from SalI-NotI digested pLCTSN-BG, and SV40 polyA signal from BglII-HindIII digested pSP72SVpA.

pLCTSN-BG was constructed by gel-purifying the following three DNA fragments: the B7-2 cDNA from pLSNB70 cut with NotI-XhoI, the EMCV IRES from pGEM-IRES8 cut with XhoI-HindIII (HindIII partial), and the GM-CSF cDNA from PCR amplified and HindIII-BamHI digested DNA (Ex. 1). The purified fragment were then ligated with NotI-BamHI digested pLCTSN to create pLCTSN-BG.

i) Construction of the pLCT-pA-BG-EF Retroviral Vector pLCT-pA-BG-EF contains a cistron comprising the EF1α enhancer/promoter, B7-2 and GM-CSF cDNAs and SV40 polyadenylation signal inserted in an inverted orientation (relative to transcription from the 5' LTR) but lacks the the neo gene found in pLCTSN-pA-BG-EF vector. pLCT-pA-BG-EF was constructed by ligation of the following three fragments with HindIII-SalI digested pLCTSN: EF1α enhancer/promoter from SalI-NotI digested pHEF, the B7-2/IRES/GM-CSF cistron from NotI-BamHI digested pLCTSN-BG, and the SV40 polyA signal from NotI-HindIII digested pSP72SVpA.

pSP72SVpA was made by PCR amplification of the SV40 polyA signal from pBlueBac-His B (Invitrogen) with primers containing HindIII and EcoRI sites and cloned into HindIII-EcoRI digested pSP72 (Promega).

The plasmids described above are introduced into tumor cells, including freshly explanted tumor cells as well as tumor cells in a patient, using injection of naked plasmid DNA, liposome mediated gene transfer or through the use of a gene gun (biolistics). The retroviral vectors described above are used to generate recombinant virus which is used to transduce the encoded IMGs into tumor cells (primary and established) in culture as described in Exs. 1 and 2.

j) Demonstration of Biologically Active GM-CSF from the GM-CSF Cistron

To demonstrate that the GM-CSF cDNA sequences isolated by PCR amplification and used to generate mono- and multi-cistronic constructs are capable of expressing active GM-CSF, the following GM-CSF bioactivity assay was performed using the GM-CSF-dependent Mo7e cell line [Genetics Institute, Cambridge, Mass.; Avanzi et al. (1990) Cellular Phyisol. 145:458].

Mo7e cells were maintained in DMEM supplemented with 10% FBS, 2 mM L-glutamine, 100 U/ml penicillin-streptomycin, and 100 U/ml GM-CSF at 37° C., 10% $CO_2$. When the cells were at exponential growth phase (viability >90%), they were washed twice with DMEM, and cultured for 48 hours in the absence of GM-CSF. After two days of GM-CSF starvation, the Mo7e cells, with around 20% viability, were washed once with DMEM and seeded into V-bottomed 96-well plates at $1\times10^4$ cells/well in a total volume of 200 µl with serial dilutions of a standard GM-CSF solution of known concentration or supernatant harvested from HeLa cells transfected with either pHEF-GM-CSF or pHEF-IL-12-GM-CSF plasmid DNA (a 1:2000 dilution of the culture supernatant was employed). After two days of culturing at 37° C., 10% $CO_2$, to each well, 20 µl of MTT (3-[4,5-dimethylthiazol-2-yl]-2,5-diphenyltetrazolium bromide) (5 mg/ml in PBS) was added and the plates were incubated for another 6 hours. The purple crystals were then collected at the bottom the well by brief centrifugation and the supernatant was aspirated. The pellets were dissolved in 100 µl of acidified isopropanol. The optical density at 570 nm ($OD_{570}$) of each well was obtained using a microplate reader. A standard carve was constructed by plotting the known GM-CSF concentrations against the $OD_{570}$ reading. GM-CSF concentration in the harvested supernatant was obtained by comparing its OD with the standard curve. The results are summarized in Table 7.

TABLE 7

Determination Of GM-CSF Concentration In Cell Culture Supernatants Of Transfected HeLa Cells

| Samples | GM-CSF Bioactivity (U/ml) | GM-CSF Protein Content (pg/ml) | $OD_{570}$ |
|---|---|---|---|
| Standard 1 | 0 | 0 | 0.2 |
| Standard 2 | 0.01 | 1 | 0.203 |
| Standard 3 | 0.05 | 5 | 0.233 |
| Standard 4 | 0.2 | 20 | 0.343 |
| Standard 5 | 0.5 | 50 | 0.60 |
| Standard 6 | 1 | 100 | 0.65 |
| pHEF-GM-CSF (1:2000) | 0.29 | 29 | 0.365 |
| pHEF-IL-12-GM-CSF (1:2000) | 0.03 | 3 | 0.235 |

The results shown in Table 7 demonstrate that the PCR amplified GM-CSF sequences encode biologically active GM-CSF. In addition these results demonstrate that placing the GM-CSF cistron downstream of another cistron (i.e., pHEF-IL-12-GM-CSF) reduces the amount of GM-CSF expressed (relative to a mono-cistronic expression vector). While the level of GM-CSF is reduced when G-CSF is the second or downstream cistron, the amount of GM-CSF produced in multi-cistronic GM-CSF construct is sufficient to provoke a biological response as demonstrated by the ability of tumor cells transduced with a bi-cistronic retrovirus (i.e., pLSNBG9) to induce systemic immunity against unmodified tumor cells (Ex. 5).

EXAMPLE 11

Human Tumor and PBL Engraftment in SCID/Beige Mice

An in vivo hu-PBL-SCID mouse/human tumor model was established to study the combined effects of B7-2 and GM-CSF expression in human tumor cells. C.B-17 scid/scid mice [Boussiotis et al. (1993) Proc. Natl. Acad. Sci. USA 90:11059] lack both T- and B-cell function but do maintain normal myeloid cell, natural killer (NK) cell, macrophage and dendritic cell functions [Shpitz et al. (1994) J. Immunol. Meth. 169:1]. To also avoid the NK activity of the SCID mouse, a new SCID mouse strain, SCID/bg, which has the NK cell function deleted was employed (C.B-17-scid-beige Inbred, Taconic).

To investigate the ability of SCID/bg mice to support the growth of human tumor cells, several established human tumor cell lines and 5 primary tumors were transplanted into the SCID/bg mice and the mice were monitored for tumor growth for up to 5 months. Primary tumors were treated as follows. Tumor samples were obtained in the operating room at the time of resection under sterile conditions. One to three grams of tumor were harvested for immediate processing. Fresh tumor biopsies were dissected to remove necrotic debris and connective tissue and were minced into 1–2 mm pieces. The pieces were then treated with the following enzymatic solutions in HBSS to provide cell suspensions:

- for glioblastomas: 0.025% collagenase, 0.04% DNase and 0.05% Pronase with shaking for 30 min at 37° C. and a further 30 min at 4° C. DMEM/F12 was used as the basis of the growth medium for primary glioblastoma cultures;
- for hepatomas: 1 mg/ml collagenase type IV, 300 U/ml DNase type IV and 10 μg/ml gentamycin sulfate at 37° C. with shaking for 30 min. RMPI 1640 or DMEM/F12 was used as the basis of the growth medium for primary hepatoma cultures;
- for colon adenocarcinomas: tumors were processed by physical dissociation (cutting) or by enzymatic treatment using 1 mg/ml collagenase type V, 10 μg/ml hyaluronidase type V, 300 U/ml DNase type IV and 10 μg/ml gentamycin sulfate. The cells suspension was then incubated at 37° C. with shaking for 60 min. DMEM was used as the basis of the growth medium for primary adenocarcinoma cultures.
- for melanomas: tumor cells were treated using the enzyme solution described above for adenocarcinomas. RPMI 1640 was used as the basis of the growth medium for primary melanoma cultures.

The resulting cell suspensions were then filtered through a fine mesh and layered onto a Ficoll-hypaque density gradient medium (Sigma) and centrifuged at 400× g for 30 min at room temp. The cells at the interface were removed and washed twice with HBSS (centrifuged at 100× g for 10 min) and counted. The cells were then seeded into the appropriate medium [e.g., RPMI 1640, DMEM, DMEM/F12 (all available from Sigma), etc. containing 10% FCS and antibiotics if desired] for culturing, resuspended into freezing medium for storage or used directly for injection into mice or for gene transfection applications.

Three to four million primary tumor cells and 2 to 6 million cells from established tumor cell lines were injected SC per flank of SCID/bg mice (both flanks were injected if a large enough cell sample was available). The mice were monitored for the presence of palpable tumors. The results are summarized in Table 8.

TABLE 8

Establishment Of Solid Human Tumors In SCID/bg Mice

| Tumor Inoculation | No. Of Cells Injected | No. Of Mice | Palpable Tumor Established (Days Post-Inoculation) | Success Rate (%) |
|---|---|---|---|---|
| Cell Lines | | | | |
| Melanoma | | | | |
| A375 | 2–5 × $10^6$ | 30 | 5–8 | 100 |
| SK-MEL-1 | 4 × $10^6$ | 12 | 20–30 | 100 |
| Hepatoma | 3 × $10^6$ | 5 | 10–15 | 100 |
| HepG2 | | | | |
| Breast Cancer | | | | |
| MDA468 | 2–5 × $10^6$ | 35 | 5–7 | 100 |
| MCF7 | 4–6 × $10^6$ | 7 | 8–14 | 100 |
| Glioblastoma | 2 × $10^6$ | 5 | 5–6 | 100 |
| D54MG | | | | |
| Primary Tumors | | | | |
| Melanoma | | | | |
| Mel DD | 4 × $10^6$ | 8 | 30–40 | 100 |
| Mel DJ | 3 × $10^6$ | 4 | 30–40 | 100 |
| Mel TM | 3 × $10^6$ | 5 | 30–40 | 100 |

The results shown in Table 8 demonstrate that the SCID/bg mice can support growth of the established human tumor lines very efficiently and they support the growth of primary tumor cells, albeit with a lower efficiency relative to the use of established tumor cell lines.

T-cell mediated allograft rejection has been demonstrated in SCID mice (scid/scid) engrafted with human PBLs [Malkovska et al. (1994) Clin. Exp. Immunol. 96:158] or human splenocytes [Alegre et al. (1994) J. Immunol. 153:2738]. However, the SCID/bg mouse strain has not previously been used in hu-PBL reconstitution studies. To determine whether the SCID/bg mouse could be reconstituted with human PBLs to provide an animal model for in vivo cancer gene therapy, SICD/bg mice were reconstituted with human PBLs by injecting 2×$10^7$ freshly isolated human PBLs into the peritoneal cavity. After 4–8 weeks, the PBL-injected mice were sacrificed and cells harvested from the peritoneal cavity, spleen, and peripheral blood were analyzed by FACS using antibodies against mouse or human cell markers. Isotype-matched mouse Igs were used for control staining. The results are summarized in Table 9. The following antibodies were used in these experiments: human markers: anti-CD45 (anti-HLe-1, Becton Dickinson), anti-CD3 (Leu-4, Becton Dickinson), anti-CD4 (Becton Dickinson), anti-CD8 (Becton Dickinson) and mouse marker: anti-mouse-H-2$K^d$ (Pharmingen).

TABLE 9

| | % Human CD45 |
|---|---|
| Spleen | 1–59% |
| PBL | 0.1–17% |
| Peritoneal Cavity | 5–69% |

The results shown in Table 9 demonstrate that SCID/bg mice were efficiently reconstituted with human lymphocytes, with CD45+ human cells constituting up to ~60% of splenocytes, up to 17% of PBLs and up to 70% of cells obtained by peritoneal lavage in the reconstituted mice.

The percentage of different human lymphocyte subsets in the CD45+ population present in the reconstituted SCIDIbg mice was examined by FACS as follows. SCID/bg mice were reconstituted with PBLs isolated from three healthy human donors as described in Ex. 3. After 4–8 weeks, the PBL-injected mice were sacrificed and lymphoid organs, PBLs and peritoneal exudates were harvested and were analyzed by FACS. The percentage of T lymphocyte subsets was also determined within the CD45+ population in the peripheral blood of human donors A and B. The following markers were examined: CD45RO (anti-CD45RO, Becton Dickinson), CD45RA (anti-CD45RA, Becton Dickinson), HLA-DR (MG2600, Caltag), CD4 and CD8. The results are summarized in Table 10. In Table 10, the following abbreviations are used: RA+ (CD45RA positive); RO+ (CD45RO positive); RO+DR+ (CD45RO and HLA-DR positive).

TABLE 10

Percentage Of T Lymphocyte Subsets In The CD45+ Population In Hu-PBL-SCID/bg Mice

| Donor/Mouse | CD4+ | CD8+ | CD4+8+ | RO+ | RA+ | RO+DR+ |
|---|---|---|---|---|---|---|
| Donor A | 53 | 23 | 1.5 | 58 | 37 | 9.9 |
| SCID/bg-A | 72 | 42 | 17 | 99 | 1 | 67 |
| Donor B | 63 | 25 | 1.6 | 58 | 37 | 9.4 |
| SCID/bg-B | 41 | 48 | 12 | 92 | 8 | 67 |
| SCID/bg-C | 51 | 44 | 21 | 76 | 24 | 35 |

The results shown in Table 10 demonstrate that the peripheral blood of the Hu-PBL-SCID/bg mice contain high numbers of immature or progenitor T cells (i.e., CD4+8+ cells and CD45RA+ cells). These results are in contrast to the results obtained by reconstitution of C.B-17scid/scid mice (Hu-PBL-SCID). In human PBL-reconstituted C.B-17 scid/scid mice most human lymphocytes exhibit activated cell phenotypes (HLA-DR+ and CD25+ or CD69+) soon after reconstitution, and almost all (>99%) human T cells exhibit mature memory phenotypes (CD45RO+) in a state of reversible anergy [Rizza et al. (1996), supra; Tarry-Lehmann and Saxon, supra; Tarry-Lehmann et al., supra]. Therefore, the lack of sufficient numbers of immature naive T cells after reconstitution renders the Hu-PBL-SCID model unsuitable for the evaluation of anti-tumor immunity. In contrast, the Hu-PBL-SCID/bg mice show evident levels of CD45RA+ and CD4+8+ cells 4–6 weeks after reconstitution. Thus, the Hu-PBL-SCID/bg mice of the present invention provide a suitable model for the evaluation of anti-tumor immunity.

EXAMPLE 12

Autologous Hu-PBL-SCID/bg/Human Tumor Model

To provide an autologous Hu-PBL-SCID/bg/human tumor model, primary human tumor cells are prepared and injected SC into the flanks of SCID/bg mice as described in Ex. 11. The primary tumor cells are first transduced with vectors encoding one or more therapeutic proteins (e.g., B7-2, GM-CSF, IL-12A, IL-12B, etc.) and mice are injected with the transduced tumor cells (after selection) as well as non-transduced tumor cells. Once palpable tumors are established (1–2 months), the mice are reconstituted with autologous PBLs (i.e., PBLs isolated from the same patient that provided the tumor cells). For each tumor, a minimum of 10 SCID/bg mice are injected with tumor cells and the rate of establishment of palpable tumors is determined. Tumors that grow with a success rate of >40% in the injected mice will receive autologous PBLs and 1 week later will receive IMG-transduced tumor cells. The tumor size (mm$^3$) is measured every 3–4 days and the mice are monitored for survival. These mice are used to determine which combinations of therapeutic or immune-modulating genes (IMGs) result in the regression of tumor size and prolonged mouse survival.

Mice from each group are sacrificed at various intervals and spleen cells and draining lymph node cells are assayed for immune reactivity (i.e., anti-tumor cellular immunity) (e.g., $^{51}$Cr release assays, proliferation and cytokine production) to determine whether any of the assays of immune reactivity correlate with observed tumor rejection.

Proliferation Assays and in Vitro Priming

Splenocytes and lymph node cells isolated from the reconstituted mice are co-cultured with lethally irradiated tumor cells transduced with IMGs for various lengths of time (minimum of 5 days) and assayed for proliferation by pulsing the cultures with $^3$H-thymidine, e.g., on day 4 of culture and determining $^3$H-thymidine incorporation into cellular DNA 18–24 hr later.

Responding lymphocytes may be restimulated repeatedly (weekly) with untransduced or transduced tumor cells to increase the frequency of T cell precursors specific to the tumor. The tumor-responsive immune cells are then transferred into mice carrying the parental tumor to determine if in vitro priming generates cells which can cause tumor regression.

Cytokine Production

Interferon γ (IFNγ), tumor necrosis factor a (TNFα), and IL-2 are cytokines associated with cell-mediated immune responses that direct the expansion and activation of NK cells and lymphokine activated killer (LAK) cells and the expansion of CD8+ CTL. Such effector cells are likely to have particular relevance to the elimination of tumors since animals lacking these effector cell types do not efficiently eliminate tumors or metastases [Whiteside et al. (1994) Clin. Immunother. 1:56].

Lymphocytes isolated from the PBL and tumor reconstituted mice are co-cultured with autologous untransduced or mock-transduced and IMG expressing tumor cells are assayed for the production of cytokines associated with cell-mediated immunity. Secretion of IFNγ, TNFα and IL-2 into the culture supernatants at various times during co-culture are assayed by sandwich ELISA [Sad et al. (1995) Immunity 2:271].

In Vitro CTL Assay

Viable cells are harvested and enumerated from co-cultures of lymphocytes with autologous tumor cells (mock transduced or expressing IMGs) after 5 days of culture or after multiple weekly stimulations (as described above). Untransduced autologous tumor cells are labelled with $^{51}$NaChromate and standard 5 hour $^{51}$Cr-release assays are performed. Lysis of autologous and allogenic tumor targets are compared to the original stimulating cells. Lysis of tumor cells matching those used as the original stimulus, but not of other tumor cells, indicates the lysis is likely antigen specific. Proof of antigen specific lysis is made by the ability to block lysis using antibodies to class I MHC molecules and the ability to eliminate the effector cell responsible for lysis through the use of anti-CD8 and complement. non-MHC restricted lysis may indicate the induction of LAK cells.

In Vitro NK/LAK Assay

Some tumor cells escape immune T cell recognition and elimination in vivo by down-regulating the expression of MHC molecules, particularly class I MHC proteins [Rivoltini et al. (1995) Cancer Res. 55:3149]. However, unlike CD8+ CTL, fresh NK cells and IL-2 expanded NK cells (LAK) do not require MHC molecules for their recognition and lysis of target cells [Lanier and Phillips (1988) ISI Atlas of Science, pp. 15–29]. NK/LAK cells may therefore serve to eliminate cells expressing altered or reduced levels of class I molecules that normally escape CD8+ T cell surveillance.

Five hour $^{51}$Cr release assays are used to determine which primary (or established) tumors are NK sensitive. Co-culture of autologous PBLs or immune cells isolated from PBL and tumor reconstituted SCID/bg mice are conducted using mock transduced or IMG expressing tumors to determine whether this results in augmented NK/LAK (non MHC) restricted cytolytic activity that includes the stimulating tumor target if initially observed, or the induction of substantial NK/LAK activity when none was present (against the tumor target) in the initial assay.

EXAMPLE 13

Delivery of Immune-modulating Genes to Human Tumors

Immune-modulating genes may be delivered to human tumor cells in vivo and ex vivo by a variety of means.

a) Retroviral Transduction

Retroviral vectors encoding immune-modulating proteins may be used to introduce IMGs into established or primary tumor cells as described in Exs. 2, 6 and 7. The transfer of IMGs using retroviruses may be made more efficient by increasing the titer of the virus encoding the IMG(s) and increasing the transduction efficiency. To increase the virus titer, single cell clones from the producer PA317 cells are be selected by growth in the presence of G418 (or selective medium suitable for the selectable marker carried on the retroviral construct) and clones producing the highest titers of virus are be expanded. To increase the titer of the producer cell line further, the PA317 cells can be reinfected with ecotropic virus [e.g., virus produced in GPE-86 packaging cells] and the best producer cell clones can be selected. To improve the transduction efficiency, retrovirus are used in combination with liposomes or poly-L-ornithine or polylysine to enhance virus uptake.

Another way to improve gene transfer efficiency using retroviruses is to increase the targeting efficiency. Many tumor cells including glioblastomas and melanomas express excess levels of the transferrin receptor. Transferrin has been used to increase the transduction efficiency of adenovirus in combination with polylysine [Lozier et al. (1994) Human Gene Ther. 5:313]. Several recent reports demonstrated that replacing the SU (surface) domain of the env gene of a retrovirus can increase receptor-mediated transduction efficiency [Kasahara et al. (1994) Science 266:1373; Cosset et al. (1995) J. Virol. 69:6314; Dong et al. (1992) J. Virol. 66:7374; and Chu and Domburg (1995) J. Virol. 69:2659]. The human transferrin gene is 2097 bp long (coding region provided in SEQ ID NO:25). Insertion of such a long sequence into the SU domain of the env gene of MLV vector may not produce a stable Env product. However, earlier studies have suggested that the modified Env fusion protein requires the native Env for stable assembly and efficient entry. Thus, the transferrin-env fusion gene is co-transfected with the native env gene to produce retrovirus particle bearing a mixture of wild type and recombinant Env. The gene transfer efficiency of the new vector is examined by transducing glioblastomas or melanomas expressing high levels of transferrin receptor.

b) Recombinant Adenoviral Vectors

Recombinant adenoviruses can accommodate relatively large segments of foreign DNA (~7 kb), and have the advantage of a broad host cell range and high titer virus production [Graham and Prevec (1991) Meth. Mol. Biol. 7:109–128]. Adenoviruses have been used in vivo in rats to efficiently deliver genes to the liver and the pancreatic islets [reviewed in Becker et al. (1994) In *Protein Expression in Animal Cells*, Roth et al. eds.] and to the central nervous system [Davidson et al (1993) Nature Genet. 3:219]. Rat livers have also been efficiently transduced ex vivo and then re-implanted [Shaked et al. (1994) Transplantation 57:1508].

The replication defective recombinant adenoviruses are employed; these viruses contain a deletion of the key immediate early genes Ela and Elb (Graham and Prevec, supra). To generate and propagate recombinant viruses, a packaging cell line such as 293 cells which supply the E1a and E2a proteins in trans is employed. Recombinant adenoviruses are created by making use of intracellular recombination between a much larger plasmid encoding most of the viral genome and a small plasmid containing the gene of interest (e.g., a cytokine) bracketed by regions of homology with the viral integration site. Recombinant adenoviruses expressing mouse IL-4 and IL-10, both under the control of a CMV immediate early enhancer promoter, have been constructed. Recombinant adenoviruses expressing human B7-2 and GM-CSF as well as a second virus expressing both the IL-12A and IL-12B subunits are constructed. The DNA constructs are cloned as bi-cistronic units with IRES as described in Ex. 1.

Standard methods are used to construct the recombinant adenoviruses (Graham and Prevec, supra and Becker et al., supra). Briefly, each plasmid is co-transfected together with pJM 17 (Microbix Systems, Toronto) into sub-confluent monolayers of 293 cells (ATCC CRL 1573) using calcium phosphate precipitation and a glycerol shock. Initial recombinant viral stocks are titered on monolayers of 293 cells, and isolated single plaques are obtained and tested for cytokine expression using an ELISA. Viral stocks are amplified and titered on 293 cells, and stored in aliquots at −70° C.; if necessary, stocks are concentrated by centrifugation on density gradients. To infect tumor cells with recombinant adenoviruses, freshly isolated tumor cells are mixed with adenoviral stocks in a minimal volume. Titers of stocks are typically $10^5$-$10^8$/ml. Medium is replaced after several hours and the cells are followed for expression of the recombinant adenoviral-encoded IMGs and/or reporter genes.

A potential drawback of using a adenoviral delivery system is that the transduced cells may retain or express small quantities of adenoviral antigens on their surface [Yang et al (1994) Nature Genet. 7:362]. "Second generation" adenoviral vectors which contain deletions in the E2a gene are available and are associated with less inflammation in the recipient and a longer period of expression of the gene of interest [Yang et al., supra and Engelhardt et al. (1994) Proc. Natl. Acad. Sci. USA 91:6196]. If necessary, IMGs are inserted into second generation adenoviral vectors. However, since the transduced tumor cells are lethally irradiated before injection into the recipient and since other manipulations are undertaken to induce the tumor cells to secrete immune-stimulating cytokines and to express surface signalling molecules, the expression of small quantities of adenoviral proteins (when first generation vectors are employed) may provide a desirable adjuvant effect. Furthermore, the recipient is subsequently boosted with retrovirally transduced tumor cells (which express the cytokines and tumor antigens, but not the adenoviral antigens). The recipient is monitored for tumor-specific immune responses at a secondary distant site where non-transduced tumor is implanted; the generation of such a response indicates that the desired tumor-specific immunity has been achieved.

c) Targeted Cationic Liposomes

Cationic liposomes have proven to be a safe and effective means for inducing the transient expression of DNA in target cells [Ledley (1995) Human Gene Ther. 6:1129; Felgner (1990) Adv. Drug Delivery Rev. 5:167; Felgner et al. (1987) Proc. Natl. Acad. Sci. USA 84:7413; and Smith et al. (1993) Biochim. Biophys. Acta 1154:327]. Clinical trails are underway using cationic liposomes to introduce the CFTR gene into the lungs of cystic fibrosis patients [Caplen et al. (1994) Gene Ther. 1:139 and Alton et al. (1993) Nature Genet. 5:135] or to introduce, by direct intra-tumor injection, the T cell costimulator B7-1 into malignant melanoma lesions in order to induce a cell-mediated immune response [Nabel et al. (1993) Proc. Natl. Acad. Sci. USA 90:11307].

Cationic liposomes (e.g., DOTAP/DOPE) and ligand-targeted cationic liposomes are employed for the delivery of IMGs to tumor cells. Ligand-targeted liposomes are made by covalently attaching ligands or antibodies to the surface of the cationic liposome. When glioblastoma cells are to be targeted, transferrin is used as the ligand as glioblastoma cells express high levels of the transferrin receptor on their surface. When melanoma cells are to be targeted, internalizing receptors, monoclonal antibodies directed against melanoma-specific surface antigens (e.g., mAb HMSA5) are employed as the ligand.

Plasmid DNA encoding IMGs (e.g., B7-2, GM-CSF and IL12) is formed into a complex with preformed cationic liposomes using standard methodology or alternatively the DNA is encapsulated into the liposome interior. The DNA-containing liposomes are then used to transfer the DNA to tumor cells in vivo by direct intra-tumor injection or in vitro (using freshly explanted tumor cells) followed by return of the transduced cells to the recipient (e.g., a patient).

d) Gene Transfer Using Biolistics

Biolistics (microballistics) is a method of delivery DNA into cells by projection of DNA-coated particles into cells or tissues. DNA is coated onto the surface of tiny (1~3 µm diameter) gold or tungsten microparticles and these particles are accelerated to high velocity and are impacted onto the target cells. The particles burst through the cell membrane and lodge within the target cell. The cell membrane quickly reseals and the passenger DNA elutes off of the particle and is expressed. The biolistic method has been used to transfect mammalian cells [Williams et al. (1991) Proc. Natl. Acad. Sci. USA 88:2726; Tang et al. (1992) Nature 356:152; Sanford et al. (1993) Methods Enzymol. 217:483].

A hand-held biolistic apparatus (BioRad) is used to transfer DNA into tumor cells or isolatedtumorfragments. This device uses compressedhelium to drive a disc-shaped macroprojectile which carries on its surface microparticles of gold (1–5 µm) of gold which have been coated with purified plasmid DNA (coprecipitated with spermine) (Williams et al., supra). This apparatus has been used to successfully transfect primary tissues.

Plasmid DNA encoding the IMGs is coated onto the surface of gold microparticles according to the manufacturer's instructions (BioRad) and the biolistic apparatus is used to transfer the DNA into freshly explanted tumor cells or directly into exposed tumors (e.g. metastatic nodules on the surface of the liver, melanoma lesions on the skin).

It is clear from the above that the present invention provides effective means to increase the immunogenicity of human tumor cells as well as humanized animal models predictive of human anti-tumor responses.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

I claim:

1. An expression vector comprising a polynucleotide sequence encoding a B7-2 protein and at least one additional immune modulating protein.

2. The expression vector according to claim 1, wherein said at least one additional immune modulating protein is a cytokine protein.

3. The expression vector according to claim 2, wherein said cytokine protein is selected from the group consisting of interleukin 2, interleukin 4, interleukin 6, interleukin 7, interleukin 12, granulocyte-macrophage colony stimulating factor, granulocyte colony stimulated factor, interferon-gamma, and tumor necrosis factor-alpha.

4. The expression vector according to claim 2, wherein said cytokine protein is granulocyte-macrophage colony stimulating factor.

5. The expression vector according to claim 1, wherein said expression vector is a viral vector.

6. The expression vector according to claim 5, wherein said viral vector is a retroviral vector.

7. The expression vector according to claim 5, wherein said viral vector is an adenoviral vector.

8. The expression vector according to claim 1, wherein said expression vector is encapsulated by, or complexed with, a liposome.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 6145 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO: 1:

```
GAATTCATAC CAGATCACCG AAAACTGTCC TCCAAATGTG TCCCCCTCAC ACTCCCAAAT      60

TCGCGGGCTT CTGCCTCTTA GACCACTCTA CCCTATTCCC CACACTCACC GGAGCCAAAG     120

CCGCGGCCCT TCCGTTTCTT TGCTTTTGAA AGACCCCACC CGTAGGTGGC AAGCTAGCTT     180

AAGTAACGCC ACTTTGCAAG GCATGGAAAA ATACATAACT GAGAATAGAA AAGTTCAGAT     240

CAAGGTCAGG AACAAAGAAA CAGCTGAATA CCAAACAGGA TATCTGTGGT AAGCGGTTCC     300
```

-continued

```
TGCCCCGGCT CAGGGCCAAG AACAGATGAG ACAGCTGAGT GATGGGCCAA ACAGGATATC   360
TGTGGTAAGC AGTTCCTGCC CCGGCTCGGG GCCAAGAACA GATGGTCCCC AGATGCGGTC   420
CAGCCCTCAG CAGTTTCTAG TGAATCATCA GATGTTTCCA GGGTGCCCCA AGGACCTGAA   480
AATGACCCTG TACCTTATTT GAACTAACCA ATCAGTTCGC TTCTCGCTTC TGTTCGCGCG   540
CTTCCGCTCT CCGAGCTCAA TAAAAGAGCC CACAACCCCT CACTCGGCGC GCCAGTCTTC   600
CGATAGACTG CGTCGCCCGG GTACCCGTAT TCCCAATAAA GCCTCTTGCT GTTTGCATCC   660
GAATCGTGGT CTCGCTGTTC CTTGGGAGGG TCTCCTCTGA GTGATTGACT ACCCACGACG   720
GGGGTCTTTC ATTTGGGGGC TCGTCCGGGA TTTGGAGACC CCTGCCCAGG GACCACCGAC   780
CCACCACCGG GAGGTAAGCT GGCCAGCAAC TTATCTGTGT CTGTCCGATT GTCTAGTGTC   840
TATGTTTGAT GTTATGCGCC TGCGTCTGTA CTAGTTAGCT AACTAGCTCT GTATCTGGCG   900
GACCCGTGGT GGAACTGACG AGTTCTGAAC ACCCGGCCGC AACCCTGGGA GACGTCCCAG   960
GGACTTTGGG GGCCGTTTTT GTGGCCCGAC CTGAGGAAGG GAGTCGATGT GGAATCCGAC  1020
CCCGTCAGGA TATGTGGTTC TGGTAGGAGA CGAGAACCTA AAACAGTTCC CGCCTCCGTC  1080
TGAATTTTTG CTTTCGGTTT GGAACCGAAG CCGCGCGTCT TGTCTGCTGC AGCGCTGCAG  1140
CATCGTTCTG TGTTGTCTCT GTCTGACTGT GTTTCTGTAT TTGTCTGAAA ATTAGGGCCA  1200
GACTGTTACC ACTCCCTTAA GTTTGACCTT AGGTCACTGG AAAGATGTCG AGCGGATCGC  1260
TCACAACCAG TCGGTAGATG TCAAGAAGAG ACGTTGGGTT ACCTTCTGCT CTGCAGAATG  1320
GCCAACCTTT AACGTCGGAT GGCCGCGAGA CGGCACCTTT AACCGAGACC TCATCACCCA  1380
GGTTAAGATC AAGGTCTTTT CACCTGGCCC GCATGGACAC CCAGACCAGG TCCCCTACAT  1440
CGTGACCTGG GAAGCCTTGG CTTTTGACCC CCCTCCCTGG GTCAAGCCCT TTGTACACCC  1500
TAAGCCTCCG CCTCCTCTTC CTCCATCCGC CCGTCTCTC CCCCTTGAAC CTCCTCGTTC  1560
GACCCCGCCT CGATCCTCCC TTTATCCAGC CCTCACTCCT TCTCTAGGCG CCGGAATTCC  1620
GATCTGATCA AGAGACAGGA TGAGGATCGT TTCGCATGAT TGAACAAGAT GGATTGCACG  1680
CAGGTTCTCC GGCCGCTTGG GTGGAGAGGC TATTCGGCTA TGACTGGGCA ACAGACAA    1740
TCGGCTGCTC TGATGCCGCC GTGTTCCGGC TGTCAGCGCA GGGGCGCCCG GTTCTTTTTG  1800
TCAAGACCGA CCTGTCCGGT GCCCTGAATG AACTGCAGGA CGAGGCAGCG CGGCTATCGT  1860
GGCTGGCCAC GACGGGCGTT CCTTGCGCAG CTGTGCTCGA CGTTGTCACT GAAGCGGGAA  1920
GGGACTGGCT GCTATTGGGC GAAGTGCCGG GGCAGGATCT CCTGTCATCT CACCTTGCTC  1980
CTGCCGAGAA AGTATCCATC ATGGCTGATG CAATGCGGCG GCTGCATACG CTTGATCCGG  2040
CTACCTGCCC ATTCGACCAC CAAGCGAAAC ATCGCATCGA GCGAGCACGT ACTCGGATGG  2100
AAGCCGGTCT TGTCGATCAG GATGATCTGG ACGAAGAGCA TCAGGGGCTC GCGCCAGCCG  2160
AACTGTTCGC CAGGCTCAAG GCGCGCATGC CCGACGGCGA GGATCTCGTC GTGACCCATG  2220
GCGATGCCTG CTTGCCGAAT ATCATGGTGG AAAATGGCCG CTTTTCTGGA TTCATCGACT  2280
GTGGCCGGCT GGGTGTGGCG GACCGCTATC AGGACATAGC GTTGGCTACC CGTGATATTG  2340
CTGAAGAGCT TGGCGGCGAA TGGGCTGACC GCTTCCTCGT GCTTTACGGT ATCGCCGCTC  2400
CCGATTCGCA GCGCATCGCC TTCTATCGCC TTCTTGACGA GTTCTTCTGA GCGGACTCT   2460
GGGGTTCGAA ATGACCGACC AAGCGACGCC CAACCTGCCA TCACGAGATT TCGATTCCAC  2520
CGCCGCCTTC TATGAAAGGT TGGGCTTCGG AATCGTTTTC CGGACGCCG GCTGGATGAT   2580
CCTCCAGCGC GGGGATCTCA TGCTGGAGTT CTTCGCCCAC CCCGGGCTCG ATCCCCTCGC  2640
```

```
GAGTTGGTTC AGCTGCTGCC TGAGGCTGGA CGACCTCGCG GAGTTCTACC GGCAGTGCAA    2700

ATCCGTCGGC ATCCAGGAAA CCAGCAGCGG CTATCCGCGC ATCCATGCCC CCGAACTGCA    2760

GGAGTGGGGA GGCACGATGG CCGCTTTGGT CGACCCGGAC GGGACGCTCC TGCGCCTGAT    2820

ACAGAACGAA TTGCTTGCAG GCATCTCATG AGTGTGTCTT CCCGTTTTCC GCCTGAGGTC    2880

ACTGCGTGGA TGGAGCGCTG GCGCCTGCTG CGCGACGGCG AGCTGCTCAC CACCCACTCG    2940

AGGGCGTGCA GCGCTGCAGA GGCCGAGTGC AGAACTGCTC CAAAGGGACC TCAAGGCTTT    3000

CCGAGGGACA CTAGGCTGAC TCCATCGAGC CAGTGTAGAG ATAAGCTTAT CGATTAGTCC    3060

AATTTGTTAA AGACAGGATA TCAGTGGTCC AGGCTCTAGT TTTGACTCAA CAATATCACC    3120

AGCTGAAGCC TATAGAGTAC GAGCCATAGA TAAAATAAAA GATTTTATTT AGTCTCCAGA    3180

AAAAGGGGGG AATGAAAGAC CCCACCTGTA GGTTTGGCAA GCTAGCTTAA GTAACGCCAT    3240

TTTGCAAGGC ATGGAAAAAT ACATAACTGA GAATAGAGAA GTTCAGATCA AGGTCAGGAA    3300

CAGATGGAAC AGCTGAATAT GGGCCAAACA GGATATCTGT GGTAAGCAGT TCCTGCCCCG    3360

GCTCAGGGCC AAGAACAGAT GGAACAGCTG AATATGGGCC AAACAGGATA TCTGTGGTAA    3420

GCAGTTCCTG CCCCGGCTCA GGGCCAAGAA CAGATGGTCC CCAGATGCGG TCCAGCCCTC    3480

AGCAGTTTCT AGAGAACCAT CAGATGTTTC CAGGGTGCCC CAAGGACCTG AAATGACCCT    3540

GTGCCTTATT TGAACTAACC AATCAGTTCG CTTCTCGCTT CTGTTCGCGC GCTTCTGCTC    3600

CCCGAGCTCA ATAAAAGAGC CCACAACCCC TCACTCGGGG CGCCAGTCCT CCGATTGACT    3660

GAGTCGCCCG GGTACCCGTG TATCCAATAA ACCCTCTTGC AGTTGCATCC GACTTGTGGT    3720

CTCGCTGTTC CTTGGGAGGG TCTCCTCTGA GTGATTGACT ACCCGTCAGC GGGGGTCTTT    3780

CATTTGGGGG CTCGTCCGGG ATCGGAGAC CCCTGCCCAG GGACCACCGA CCCACCACCG    3840

GGAGGTAAGC TGGCTGCCTC GCGCGTTTCG GTGATGACGG TGAAAACCTC TGACACATGC    3900

AGCTCCCGGA GACGGTCACA GCTTGTCTGT AAGCGGATGC CGGGAGCAGA CAAGCCCGTC    3960

AGGGCGCGTC AGCGGGTGTT GGCGGGTGTC GGGGCGCAGC CATGACCCAG TCACGTAGCG    4020

ATAGCGGAGT GTATACTGGC TTAACTATGC GGCATCAGAG CAGATTGTAC TGAGAGTGCA    4080

CCATATGCGG TGTGAAATAC CGCACAGATG CGTAAGGAGA AAATACCGCA TCAGGCGCTC    4140

TTCCGCTTCC TCGCTCACTG ACTCGCTGCG CTCGGTCGTT CGGCTGCGGC GAGCGGTATC    4200

AGCTCACTCA AAGGCGGTAA TACGGTTATC CACAGAATCA GGGGATAACG CAGGAAAGAA    4260

CATGTGAGCA AAAGGCCAGC AAAAGGCCAG GAACCGTAAA AAGGCCGCGT TGCTGGCGTT    4320

TTTCCATAGG CTCCGCCCCC CTGACGAGCA TCACAAAAAT CGACGCTCAA GTCAGAGGTG    4380

GCGAAACCCG ACAGGACTAT AAAGATACCA GGCGTTTCCC CCTGGAAGCT CCCTCGTGCG    4440

CTCTCCTGTT CCGACCCTGC CGCTTACCGG ATACCTGTCC GCCTTTCTCC CTTCGGGAAG    4500

CGTGGCGCTT TCTCATAGCT CACGCTGTAG GTATCTCAGT TCGGTGTAGG TCGTTCGCTC    4560

CAAGCTGGGC TGTGTGCACG AACCCCCCGT TCAGCCCGAC CGCTGCGCCT TATCCGGTAA    4620

CTATCGTCTT GAGTCCAACC CGGTAAGACA CGACTTATCG CCACTGGCAG CAGCCACTGG    4680

TAACAGGATT AGCAGAGCGA GGTATGTAGG CGGTGCTACA GAGTTCTTGA AGTGGTGGCC    4740

TAACTACGGC TACACTAGAA GGACAGTATT TGGTATCTGC GCTCTGCTGA AGCCAGTTAC    4800

CTTCGGAAAA AGAGTTGGTA GCTCTTGATC CGGCAAACAA ACCACCGCTG GTAGCGGTGG    4860

TTTTTTTGTT TGCAAGCAGC AGATTACGCG CAGAAAAAAA GGATCTCAAG AAGATCCTTT    4920

GATCTTTTCT ACGGGGTCTG ACGCTCAGTG GAACGAAAAC TCACGTTAAG GGATTTTGGT    4980

CATGAGATTA TCAAAAGGA TCTTCACCTA GATCCTTTTA AATTAAAAAT GAAGTTTTAA    5040
```

-continued

```
ATCAATCTAA AGTATATATG AGTAAACTTG GTCTGACAGT TACCAATGCT TAATCAGTGA      5100

GGCACCTATC TCAGCGATCT GTCTATTTCG TTCATCCATA GTTGCCTGAC TCCCCGTCGT      5160

GTAGATAACT ACGATACGGG AGGGCTTACC ATCTGGCCCC AGTGCTGCAA TGATACCGCG      5220

AGACCCACGC TCACCGGCTC CAGATTTATC AGCAATAAAC CAGCCAGCCG GAAGGGCCGA      5280

GCGCAGAAGT GGTCCTGCAA CTTTATCCGC CTCCATCCAG TCTATTAATT GTTGCCGGGA      5340

AGCTAGAGTA AGTAGTTCGC CAGTTAATAG TTTGCGCAAC GTTGTTGCCA TTGCTGCAGG      5400

CATCGTGGTG TCACGCTCGT CGTTTGGTAT GGCTTCATTC AGCTCCGGTT CCCAACGATC      5460

AAGGCGAGTT ACATGATCCC CCATGTTGTG CAAAAAAGCG GTTAGCTCCT TCGGTCCTCC      5520

GATCGTTGTC AGAAGTAAGT TGGCCGCAGT GTTATCACTC ATGGTTATGG CAGCACTGCA      5580

TAATTCTCTT ACTGTCATGC CATCCGTAAG ATGCTTTTCT GTGACTGGTG AGTACTCAAC      5640

CAAGTCATTC TGAGAATAGT GTATGCGGCG ACCGAGTTGC TCTTGCCCGG CGTCAACACG      5700

GGATAATACC GCGCCACATA GCAGAACTTT AAAAGTGCTC ATCATTGGAA AACGTTCTTC      5760

GGGGCGAAAA CTCTCAAGGA TCTTACCGCT GTTGAGATCC AGTTCGATGT AACCCACTCG      5820

TGCACCCAAC TGATCTTCAG CATCTTTTAC TTTCACCAGC GTTTCTGGGT GAGCAAAAAC      5880

AGGAAGGCAA AATGCCGCAA AAAAGGGAAT AAGGGCGACA CGGAAATGTT GAATACTCAT      5940

ACTCTTCCTT TTTCAATATT ATTGAAGCAT TTATCAGGGT TATTGTCTCA TGAGCGGATA      6000

CATATTTGAA TGTATTTAGA AAAATAAACA AATAGGGGTT CCGCGCACAT TTCCCCGAAA      6060

AGTGCCACCT GACGTCTAAG AAACCATTAT TATCATGACA TTAACCTATA AAAATAGGCG      6120

TATCACGAGG CCCTTTCGTC TTCAA                                           6145

(2) INFORMATION FOR SEQ ID NO: 2:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 2:

GATCTAAGCT TGCGGCCGCA GATCTCGAGC CATGGATCCT AGGCCTGATC ACGCGTCGAC      60

TCGCGAT                                                               67

(2) INFORMATION FOR SEQ ID NO: 3:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 3:

CGATCGCGAG TCGACGCGTG ATCAGGCCTA GGATCCATGG CTCGAGATCT GCGGCCGCAA      60

GCTTA                                                                 65

(2) INFORMATION FOR SEQ ID NO: 4:

(i) SEQUENCE CHARACTERISTICS:
```

(A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 4:

AAGCTTGATC ACCACCATGA TTGAACAAGA TGG                                    33

(2) INFORMATION FOR SEQ ID NO: 5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 5:

CCGGATCCGT CGACCCCAGA GTCCCGCTCA GAAG                                   34

(2) INFORMATION FOR SEQ ID NO: 6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 6:

CCCGGGAAGC TTCCACCATG TGGCTGCAGA GCCTG                                  35

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 7:

AATGGATCCT ATCACTCCTG GACTGGCTC                                         29

(2) INFORMATION FOR SEQ ID NO: 8:

(i) SEQUENCE CHARACTERISTICS:
        (A) LENGTH: 435 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 8:

ATGTGGCTGC AGAGCCTGCT GCTCTTGGGC ACTGTGGCCT GCAGCATCTC TGCACCCGCC       60

CGCTCGCCCA GCCCCAGCAC GCAGCCCTGG GAGCATGTGA ATGCCATCCA GGAGGCCCGG      120

CGTCTCCTGA ACCTGAGTAG AGACACTGCT GCTGAGATGA ATGAAACAGT AGAAGTCATC      180

```
TCAGAAATGT TTGACCTCCA GGAGCCGACC TGCCTACAGA CCCGCCTGGA GCTGTACAAG        240

CAGGGCCTGC GGGGCAGCCT CACCAAGCTC AAGGGCCCCT TGACCATGAT GGCCAGCCAC        300

TACAAGCAGC ACTGCCCTCC AACCCCGGAA ACTTCCTGTG CAACCCAGAT TATCACCTTT        360

GAAAGTTTCA AAGAGAACCT GAAGGACTTT CTGCTTGTCA TCCCCTTTGA CTGCTGGGAG        420

CCAGTCCAGG AGTGA                                                        435
```

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 9:

```
TGTGGATCCA CCATGGGACT GAGTAACATT                                         30
```

(2) INFORMATION FOR SEQ ID NO: 10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 10:

```
TTTGGATCCT TAAAAACATG TATCACTTTT GTCGC                                   35
```

(2) INFORMATION FOR SEQ ID NO: 11:

(i) SEQUENCE CHARACTERISTICS:
        (A) LENGTH: 972 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 11:

```
ATGGGACTGA GTAACATTCT CTTTGTGATG GCCTTCCTGC TCTCTGGTGC TGCTCCTCTG         60

AAGATTCAAG CTTATTTCAA TGAGACTGCA GACCTGCCAT GCCAATTTGC AAACTCTCAA        120

AACCAAAGCC TGAGTGAGCT AGTAGTATTT TGGCAGGACC AGGAAAACTT GGTTCTGAAT        180

GAGGTATACT TAGGCAAAGA GAAATTTGAC AGTGTTCATT CCAAGTATAT GGGCCGCACA        240

AGTTTTGATT CGGACAGTTG GACCCTGAGA CTTCACAATC TTCAGATCAA GGACAAGGGC        300

TTGTATCAAT GTATCATCCA TCACAAAAAG CCCACAGGAA TGATTCGCAT CCACCAGATG        360

AATTCTGAAC TGTCAGTGCT TGCTAACTTC AGTCAACCTG AAATAGTACC AATTTCTAAT        420

ATAACAGAAA ATGTGTACAT AAATTTGACC TGCTCATCTA TACACGGTTA CCCAGAACCT        480

AAGAAGATGA GTGTTTTGCT AAGAACCAAG AATTCAACTA TCGAGTATGA TGGTATTATG        540

CAGAAATCTC AAGATAATGT CACAGAACTG TACGACGTTT CCATCAGCTT GTCTGTTTCA        600

TTCCCTGATG TTACGAGCAA TATGACCATC TTCTGTATTC TGGAAACTGA CAAGACGCGG        660
```

```
CTTTTATCTT CACCTTTCTC TATAGAGCTT GAGGACCCTC AGCCTCCCCC AGACCACATT      720

CCTTGGATTA CAGCTGTACT TCCAACAGTT ATTATATGTG TGATGGTTTT CTGTCTAATT      780

CTATGGAAAT GGAAGAAGAA GAAGCGGCCT CGCAACTCTT ATAAATGTGG AACCAACACA      840

ATGGAGAGGG AAGAGAGTGA ACAGACCAAG AAAAGAGAAA AAATCCATAT ACCTGAAAGA      900

TCTGATGAAG CCCAGCGTGT TTTTAAAAGT TCGAAGACAT CTTCATGCGA CAAAAGTGAT      960

ACATGTTTTT AA                                                         972

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 12:

AAAAGCTTGG ATCCACCATG AGTAAAGGA                                        29

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 13:

AATCTAGATT ACTATTTGTA TAGTTCATCC                                       30

(2) INFORMATION FOR SEQ ID NO: 14:

(i) SEQUENCE CHARACTERISTICS:
        (A) LENGTH: 1451 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

AAGCTTTGGA GCTAAGCCAG CAATGGTAGA GGGAAGATTC TGCACGTCCC TTCCAGGCGG       60

CCTCCCCGTC ACCACCCCCC CCAACCCGCC CCGACCGGAG CTGAGAGTAA TTCATACAAA      120

AGGACTCGCC CCTGCCTTGG GGAATCCCAG GGACCGTCGT TAAACTCCCA CTAACGTAGA      180

ACCCAGAGAT CGCTGCGTTC CCGCCCCCTC ACCCGCCCGC TCTCGTCATC ACTGAGGTGG      240

AGAAGAGCCA TGCGTGAGGC TCCGGTGCCC GTCAGTGGGC AGAGCGCACA TCGCCCACAG      300

TCCCCGAGAA GTTGGGGGGA GGGGTCGGCA ATTGAACCGG TGCCTAGAGA AGGTGGCGCG      360

GGGTAAACTG GGAAAGTGAT GTCGTGTACT GGCTCCGCCT TTTTCCCGAG GGTGGGGGAG      420

AACCCGTATA TAAGTGCAGT AGTCGCCGTG AACGTTCTTT TTCGCAACGG GTTTGCCGCC      480

AGAACACAGG TAAGTGCCGT GTGTGGTTCC CGCGGGCCTG GCCTCTTTAC GGGTTATGGC      540

CCTTGCGTGC CTTGAATTAC TTCCACGCCC CTGGCTGCAG TACGTGATTC TTGATCCCGA      600

GCTTCGGGTT GGAAGTGGGT GGGAGAGTTC GAGGCCTTGC GCTTAAGGAG CCCCTTCGCC      660
```

```
TCGTGCTTGA GTTGAGGCCT GGCCTGGGCG CTGGGGCCCC CGCGTGCGAA TCTGGTGGCA      720

CCTTCGCGCC TGTCTCGCTG CTTTCGATAA GTCTCTAGCC ATTTAAAATT TTTGATGACC      780

TGCTGCGACG CTTTTTTTCT GGCAAGATAG TCTTGTAAAT GCGGGCCAAG ATCTGCACAC      840

TGGTATTTCG GTTTTTGGGG CCGCGGGCGG CGACGGGGCC CGTGCGTCCC AGCGCACATG      900

TTCGGCGAGG CGGGGCCTGC GAGCGCGGCC ACCGAGAATC GGACGGGGGT AGTCTCAAGC      960

TGGCCGGCCT GCTCTGGTGC CTGGCCTCGC GCCGCCGTGT ATCGCCCCGC CCTGGGCGGC     1020

AAGGCTGGCC CGGTCGGCAC CAGTTGCGTG AGCGGAAAGA TGGCCGCTTC CCGGCCCTGC     1080

TGCAGGGAGC TCAAAATGGA GGACGCGGCG CTCGGGAGAG CGGGCGGGTG AGTCACCCAC     1140

ACAAAGGAAA AGGGCCTTTC CGTCCTCAGC CGTCGCTTCA TGTGACTCCA CGGAGTACCG     1200

GGCGCCGTCC AGGCACCTCG ATTAGTTCTC GAGCTTTTGG AGTACGTCGT CTTTAGGTTG     1260

GGGGAGGGG TTTTATGCGA TGGAGTTTCC CCACACTGAG TGGGTGGAGA CTGAAGTTAG     1320

GCCAGCTTGG CACTTGATGT AATTCTCCTT GGAATTTGCC CTTTTTGAGT TTGGATCTTG     1380

GTTCATTCTC AAGCCTCAGA CAGTGGTTCA AGTTTTTTTT CTTCCATTTC AGGTGTCGTG     1440

AAAACTCTAG A                                                         1451
```

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 15:

```
AAGCTTTGGA GCTAAGCCAG CAAT                                             24
```

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 16:

```
TCTAGAGTTT TCACGACACC TGA                                              23
```

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 17:

```
TCTAGAGCGG CCGCGGAGGC CGAATTCG                                         28
```

(2) INFORMATION FOR SEQ ID NO: 18:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA"

(xi) SEQUENCE DESCRIPTION: SEQ ID NO: 18:

GATCCGAATT CGGCCTCCGC GGCCGCTCTA GATGCA                36

(2) INFORMATION FOR SEQ ID NO: 19:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO: 19:

GAAGATCTGC GGCCGCCACC ATGTGGCCCC CTGGGTCAGC            40

(2) INFORMATION FOR SEQ ID NO: 20:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO: 20:

CCTCTCGAGT TAGGAAGCAT TCAGATAGC                        29

(2) INFORMATION FOR SEQ ID NO: 21:

(i) SEQUENCE CHARACTERISTICS:
       (A) LENGTH: 762 base pairs
       (B) TYPE: nucleic acid
       (C) STRANDEDNESS: double
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO: 21:

ATGTGGCCCC CTGGGTCAGC CTCCCAGCCA CCGCCCTCAC CTGCCGCGGC CACAGGTCTG    60

CATCCAGCGG CTCGCCCTGT GTCCCTGCAG TGCCGGCTCA GCATGTGTCC AGCGCGCAGC   120

CTCCTCCTTG TCGCTACCCT GGTCCTCCTG GACCACCTCA GTTTGGCCAG AAACCTCCCC   180

GTGGCCACTC CAGACCCAGG AATGTTCCCA TGCCTTCACC ACTCCCAAAA CCTGCTGAGG   240

GCCGTCAGCA ACATGCTCCA GAAGGCCAGA CAAACTCTAG AATTTTACCC TTGCACTTCT   300

GAAGAGATTG ATCATGAAGA TATCACAAAA GATAAAACCA GCACAGTGGA GGCCTGTTTA   360

CCATTGGAAT TAACCAAGAA TGAGAGTTGC CTAAATTCCA GAGAGACCTC TTTCATAACT   420

AATGGGAGTT GCCTGGCCTC CAGAAAGACC TCTTTTATGA TGGCCCTGTG CCTTAGTAGT   480

ATTTATGAAG ACTTGAAGAT GTACCAGGTG GAGTTCAAGA CCATGAATGC AAAGCTTCTG   540

ATGGATCCTA AGAGGCAGAT CTTTCTAGAT CAAAACATGC TGGCAGTTAT TGATGAGCTG   600

| ATGCAGGCCC TGAATTTCAA CAGTGAGACT GTGCCACAAA AATCCTCCCT TGAAGAACCG | 660 |
| GATTTTTATA AAACTAAAAT CAAGCTCTGC ATACTTCTTC ATGCTTTCAG AATTCGGGCA | 720 |
| GTGACTATTG ATAGAGTGAT GAGCTATCTG AATGCTTCCT AA | 762 |

(2) INFORMATION FOR SEQ ID NO: 22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 22:

| AAAGAGCTCC ACCATGTGTC ACCAGCAGTT GGTC | 34 |

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 23:

| AAGGATCCTA ACTGCAGGGC ACAGATGC | 28 |

(2) INFORMATION FOR SEQ ID NO: 24:

(i) SEQUENCE CHARACTERISTICS:
        (A) LENGTH: 987 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 24:

| ATGTGTCACC AGCAGTTGGT CATCTCTTGG TTTTCCCTGG TTTTTCTGGC ATCTCCCCTC | 60 |
| GTGGCCATAT GGGAACTGAA GAAAGATGTT TATGTCGTAG AATTGGATTG GTATCCGGAT | 120 |
| GCCCCTGGAG AAATGGTGGT CCTCACCTGT GACACCCCTG AAGAAGATGG TATCACCTGG | 180 |
| ACCTTGGACC AGAGCAGTGA GGTCTTAGGC TCTGGCAAAA CCCTGACCAT CCAAGTCAAA | 240 |
| GAGTTTGGAG ATGCTGGCCA GTACACCTGT CACAAAGGAG GCGAGGTTCT AAGCCATTCG | 300 |
| CTCCTGCTGC TTCACAAAAA GGAAGATGGA ATTTGGTCCA CTGATATTTT AAAGGACCAG | 360 |
| AAAGAACCCA AAAATAAGAC CTTTCTAAGA TGCGAGGCCA AGAATTATTC TGGACGTTTC | 420 |
| ACCTGCTGGT GGCTGACGAC AATCAGTACT GATTTGACAT TCAGTGTCAA AGCAGCAGA | 480 |
| GGCTCTTCTG ACCCCCAAGG GGTGACGTGC GGAGCTGCTA CACTCTCTGC AGAGAGAGTC | 540 |
| AGAGGGACA ACAAGGAGTA TGAGTACTCA GTGGAGTGCC AGGAGGACAG TGCCTGCCCA | 600 |
| GCTGCTGAGG AGAGTCTGCC CATTGAGGTC ATGGTGGATG CCGTTCACAA GCTCAAGTAT | 660 |
| GAAAACTACA CCAGCAGCTT CTTCATCAGG GACATCATCA AACCTGACCC ACCCAACAAC | 720 |
| TTGCAGCTGA AGCCATTAAA GAATTCTCGG CAGGTGGAGG TCAGCTGGGA GTACCCTGAC | 780 |
| ACCTGGAGTA CTCCACATTC CTACTTCTCC CTGACATTCT GCGTTCAGGT CCAGGGCAAG | 840 |

```
AGCAAGAGAG AAAAGAAAGA TAGAGTCTTC ACCGACAAGA CCTCAGCCAC GGTCATCTGC      900

CGCAAAAATG CCAGCATTAG CGTGCGGGCC CAGGACCGCT ACTATAGCTC ATCTTGGAGC      960

GAATGGGCAT CTGTGCCCTG CAGTTAG                                         987

(2) INFORMATION FOR SEQ ID NO: 25:

(i) SEQUENCE CHARACTERISTICS:
        (A) LENGTH: 2097 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 25:

ATGAGGCTCG CCGTGGGAGC CCTGCTGGTC TGCGCCGTCC TGGGGCTGTG TCTGGCTGTC       60

CCTGATAAAA CTGTGAGATG GTGTGCAGTG TCGGAGCATG AGGCCACTAA GTGCCAGAGT      120

TTCCGCGACC ATATGAAAAG CGTCATTCCA TCCGATGGTC CCAGTGTTGC TTGTGTGAAG      180

AAAGCCTCCT ACCTTGATTG CATCAGGGCC ATTGCGGCAA ACGAAGCGGA TGCTGTGACA      240

CTGGATGCAG GTTTGGTGTA TGATGCTTAC TTGGCTCCCA ATAACCTGAA GCCTGTGGTG      300

GCAGAGTTCT ATGGGTCAAA AGAGGATCCA CAGACTTTCT ATTATGCTGT TGCTGTGGTG      360

AAGAAGGATA GTGGCTTCCA GATGAACCAG CTTCGAGGCA AGAAGTCCTG CCACACGGGT      420

CTAGGCAGGT CCGCTGGGTG AACATCCCC ATAGGCTTAC TTTACTGTGA CTTACCTGAG      480

CCACGTAAAC CTCTTGAGAA AGCAGTGGCC AATTTCTTCT CGGGCAGCTG TGCCCCTTGT      540

GCGGATGGGA CGGACTTCCC CCAGCTGTGT CAACTGTGTC CAGGGTGTGG CTGCTCCACC      600

CTTAACCAAT ACTTCGGCTA CTCGGGAGCC TTCAAGTGTC TGAAGGATGG TGCTGGGGAT      660

GTGGCCTTTG TCAAGCACTC GACTATATTT GAGAACTTGG CAAACAAGGC TGACAGGGAC      720

CAGTATGAGC TGCTTTGCCT AGACAACACC CGGAAGCCGG TAGATGAATA CAAGGACTGC      780

CACTTGGCCC AGGTCCCTTC TCATACCGTC GTGGCCCGAA GTATGGGCGG CAAGGAGGAC      840

TTGATCTGGG AGCTTCTCAA CCAGGCCCAG GAACATTTTG GCAAAGACAA ATCAAAAGAA      900

TTCCAACTAT TCAGCTCTCC TCATGGGAAG GACCTGCTGT TTAAGGACTC TGCCCACGGG      960

TTTTTAAAAG TCCCCCCAAG GATGGATGCC AAGATGTACC TGGGCTATGA GTATGTCACT     1020

GCCATCCGGA ATCTACGGGA AGGCACATGC CCAGAAGCCC AACAGATGA ATGCAAGCCT     1080

GTGAAGTGGT GTGCGCTGAG CCACCACGAG AGGCTCAAGT GTGATGAGTG GAGTGTTAAC     1140

AGTGTAGGGA AAATAGAGTG TGTATCAGCA GAGACCACCG AAGACTGCAT CGCCAAGATC     1200

ATGAATGGAG AAGCTGATGC CATGAGCTTG GATGGAGGGT TTGTCTACAT AGCGGGCAAG     1260

TGTGGTCTGG TGCCTGTCTT GGCAGAAAAC TACAATAAGA GCGATAATTG TGAGGATACA     1320

CCAGAGGCAG GGTATTTTGC TGTAGCAGTG GTGAAGAAAT CAGCTTCTGA CCTCACCTGG     1380

GACAATCTGA AGGCAAGAA GTCCTGCCAT ACGGCAGTTG CAGAACCGC TGGCTGGAAC     1440

ATCCCCATGG GCCTGCTCTA CAATAAGATC AACCACTGCA GATTTGATGA ATTTTTCAGT     1500

GAAGGTTGTG CCCCTGGGTC TAAGAAAGAC TCCAGTCTCT GTAAGCTGTG TATGGGCTCA     1560

GGCCTAAACC TGTGTGAACC CAACAACAAA GAGGGATACT ACGGCTACAC AGGCGCTTTC     1620

AGGTGTCTGG TTGAGAAGGG AGATGTGGCC TTTGTGAAAC ACCAGACTGT CCCACAGAAC     1680

ACTGGGGGAA AAAACCCTGA TCCATGGGCT AAGAATCTGA ATGAAAAGA CTATGAGTTG     1740
```

-continued

| | | | | | |
|---|---|---|---|---|---|
| CTGTGCCTTG | ATGGTACCAG | GAAACCTGTG | GAGGAGTATG | CGAACTGCCA | CCTGGCCAGA | 1800 |
| GCCCCGAATC | ACGCTGTGGT | CACACGGAAA | GATAAGGAAG | CTTGCGTCCA | CAAGATATTA | 1860 |
| CGTCAACAGC | AGCACCTATT | TGGAAGCAAC | GTAACTGACT | GCTCGGGCAA | CTTTTGTTTG | 1920 |
| TTCCGGTCGG | AAACCAAGGA | CCTTCTGTTC | AGAGATGACA | CAGTATGTTT | GGCCAAACTT | 1980 |
| CATGACAGAA | ACACATATGA | AAAATACTTA | GGAGAAGAAT | ATGTCAAGGC | TGTTGGTAAC | 2040 |
| CTGAGAAAAT | GCTCCACCTC | ATCACTCCTG | GAAGCCTGCA | CTTTCCGTAG | ACCTTAA | 2097 |